(12) United States Patent
Donald

(10) Patent No.: US 8,722,367 B2
(45) Date of Patent: *May 13, 2014

(54) DETECTING PAX2 FOR THE DIAGNOSIS OF BREAST CANCER

(75) Inventor: Carlton D. Donald, Atlanta, GA (US)

(73) Assignee: Phigenix, Inc., Atlanta, GA (US)

( * ) Notice: Subject to any disclaimer, the term of this patent is extended or adjusted under 35 U.S.C. 154(b) by 15 days.

This patent is subject to a terminal disclaimer.

(21) Appl. No.: 13/606,917

(22) Filed: Sep. 7, 2012

(65) Prior Publication Data

US 2013/0023424 A1  Jan. 24, 2013

Related U.S. Application Data

(63) Continuation of application No. 12/546,292, filed on Aug. 24, 2009, now abandoned, which is a continuation-in-part of application No. 12/440,193, filed as application No. PCT/US2008/051168 on Jan. 16, 2008, now Pat. No. 8,088,603.

(60) Provisional application No. 60/885,142, filed on Jan. 16, 2007.

(51) Int. Cl.
*C12P 19/34* (2006.01)
*C12Q 1/68* (2006.01)

(52) U.S. Cl.
USPC .......................................... 435/91.2; 435/6.1

(58) Field of Classification Search
USPC .................................................. 435/91.2, 6.1
See application file for complete search history.

(56) References Cited

U.S. PATENT DOCUMENTS

| | | | |
|---|---|---|---|
| 4,816,567 A | 3/1989 | Cabilly et al. | |
| 2001/0031882 A1 | 10/2001 | Serhan | |
| 2003/0198970 A1 | 10/2003 | Roberts | |
| 2004/0037842 A1 | 2/2004 | Meagher et al. | |
| 2004/0142389 A1 | 7/2004 | O'Mahony et al. | |
| 2005/0287127 A1 | 12/2005 | Li et al. | |
| 2006/0019256 A1 | 1/2006 | Clarke et al. | |
| 2006/0211008 A1 | 9/2006 | Mongroo et al. | |
| 2007/0010469 A1 | 1/2007 | Chan et al. | |
| 2007/0166728 A1 | 7/2007 | Abramson | |
| 2011/0183866 A1* | 7/2011 | Clarke et al. .............. | 506/9 |

FOREIGN PATENT DOCUMENTS

| | | |
|---|---|---|
| WO | 00/49175 | 8/2000 |
| WO | 2004/108899 | 12/2004 |
| WO | 2006/002433 | 1/2006 |

OTHER PUBLICATIONS

Xiang et al., "AMP-activated protein kinase activators can inhibit the growth of prostate cancer cells by multiple mechanisms," Biochemical and Biophysical Research Communications, 2004, pp. 161-167, vol. 321.

Wallen et al., "Dependence of BSAP Repressor and Activator Functions on BSAP Concentration," Science, 1998, vol. 279.
Vogelstein et al., "The multistep nature of Cancer," Trends in Genetics, Apr. 1993, pp. 138-141, vol. 9—No. 4.
Uemura et al., "Angiotensin II Receptor Blocker: Possibility of Antitumor Agent for Prostate Cancer," Mini-Reviews in Medicinal Chemistry, 2006, pp. 835-844, vol. 6.
Uemura et al., "Renin-Angiotensin system is an Important factor in Hormone Refractory Prostate Cancer," The Prostate, 2006 pp. 822-830, vol. 66.
Tepper et al., "Profiling of Gene Expression Changes Caused by p53 Gain-of-Function Mutant Alleles in Prostate Cancer Cells," The Prostate, 2005, pp. 375-389, vol. 65.
Stuart et al. "Mammalian Pax genes," Annual Review of Genetics, 1994, pp. 219-236, vol. 28.
Stuart et al., "PAX and HOX in Neoplasia," Advances in Genetics, 1995, pp. 255-274, vol. 33.
Stambolic, "Negative Regulation of PKB/Akt-Dependent Cell Survival by the Tumor Suppressor PTEN," Cell, 1998, pp. 29-39, vol. 95.
Seiden et al., "Detection of Circulating Tumor Cells in Men with localized Prostate Cancer," Journal of Clinical Oncology, 1994, pp. 2634-2639, vol. 12—No. 12.
Sherman et al., "Albumin and amino acids upregulate the expression of human beta-defensin 1," Molecular Immunology, 2006, pp. 1617-1623.
Schmidt et al., "Detection of Circulating Prostate Cells during Radical Prostatectomy by Standardized PSMA RT-PCR: Association with Positive Lymph Nodes and High Malignant Grade," Anticancer Research, 2003, pp. 3991-4000, vol. 23.
Sanyanusin et al., "Genomic Structure of the Human PAX2 Gene," Genomics, Jul. 1, 1996, pp. 258, vol. 35.
Saitoh et al., "Adenosine induces apoptosis in the human gastric cancer cells via an intrinsic pathway relevant to activation of AMP-activated protein kinase," Biochemical Pharmacology, 2004, pp. 2005-2011, vol. 67.
Robson et al., "A Panorama of PAX genes in cancer and development," Nature Reviews Cancer, Jan. 2006, pp. 52-62, vol. 6.
Rieger et al., "Human blader carcinoma cell lines as indicators of oncogenic change relevant to urothelial neoplastic progression," British Journal of Cancers, 1995, pp. 683-690, vol. 72.
Papo et al., "Vision and Reflections: Host defence peptides as new weapons in cancer treatment," Cellular and Molecular Life Sciences, 2005, pp. 784-790, vol. 62.
Pantel et al., "Micrometastasis Detection and Treatment with Monoclonal Antibodies," Current Topics in Microbiology and Immunology, 1996, pp. 1-18, vol. 213—Part 3.

(Continued)

*Primary Examiner* — Cynthia B Wilder
(74) *Attorney, Agent, or Firm* — Ping Wang; Andrews Kurth, LLP

(57) ABSTRACT

A method for monitoring breast conditions in a subject is disclosed. The method comprises determining a Paired Box 2 gene-to-beta defensin-1 gene (PAX2-to-DEFB1) expression ratio (the "Donald Predictive Factor" or "DPF") in cells obtained from the breast of the subject, wherein the PAX2-to-DEFB1 expression ratio is correlated with breast conditions. Also disclosed is a kit for monitoring breast conditions and determining drug resistance.

19 Claims, 37 Drawing Sheets

(56) References Cited

OTHER PUBLICATIONS

Noguchi et al., "Detection of Breast Cancer Micrometastases in Axillary Lymph Nodes by Means of Reverse Transcriptase-Polymerase Chain Reaction," American Journal of Pathology, 1996, pp. 249-256, vol. 148—No. 2.
Nelson et al., "The Role of Inflammation in the Pathogenesis of Prostate Cancer," The Journal of Urology, Nov. 2004, pp. S6-S12, vol. 172—Issue 5.
Meisse et al., "Sustained activation of AMP-activated protein kinase induces c-Jun N-terminal kinase activation and apoptosis in liver cells," FEBS Letters, 2002, pp. 38-42, vol. 526.
McNamara et al., "Ocular Surface Epithelia Express mRNA for Human Beta Defensin-2," Experimental Eye Research, 1999, pp. 483-490, vol. 69.
Maulbecker et al., "The oncogenic potential of PAX genes," The EMBO Journal, 1993, pp. 2361-2367, vol. 12—No. 6.
Matsumura et al., "Detection of α-Fetoprotein mRNA, an Indicator of Hematogenous Spreading Hepatocellular Carcinoma, in the Circulation: A Possible Predictor of Metastatic Hepatocellular Carcinoma," Hepatology, 1994, pp. 1418-1425, vol. 20—No. 6.
McCray et al, "Human Epithelia Express a β-defensin," American Journal of Respiratory Cell and Molecular Biology, 1997, pp. 343-349, vol. 16.
Mansouri et al., "Pax genes and their roles in cell differentiation and development," Current Opinion in Cell Biology, 1996, pp. 851-857, vol. 8.
Li et al., "AMPK-β1 submit is a p53-independent stress responsive protein that inhibits tumor cell growth upon forced expression," Carcinogenesis, 2003, pp. 827-834, vol. 24—No. 5.
Lehrer et al., "Endogenous Vertebrate Antibiotics. Defensins, Protegrins, and Other Cysteine-Rich Antimicrobial Peptides," Annals of the New York Academy of Sciences, Oct. 25, 1996, pp. 228-239, vol. 797.
Lang et al., "PAX genes: Role in development, pathophysiology, and cancer," Biochemical Pharmacology, Jan. 1, 2007, pp. 1-14, vol. 73—No. 1.
Kasahara et al., "Detection of genetic alterations in advances prostate cancer by comparative genomic hybridization," Cancer Genetics and Cytogenetics, 2002, pp. 59-63, vol. 137.
Jurevic et al., "Single-Nucleotide Polymorphisms and Haplotype Analysis in β-Defensin Genes in Different Ethnic Populations," Genetic Testing, 2002, pp. 261-269, vol. 6—No. 4.
Jung et al., "5-Aminoimidazole-4-carboxamide-ribonucleoside enhances oxidative stress-induced apoptosis through activation of nuclear factor-KB in mouse Neuro 2a neuroblastoma cells," Neuroscience Letters, 2004, pp. 197-200, vol. 354.
Jotsuka et al., "Persistent evidence of circulating tumor cells detected by means of RT-PCR for CEA mRNA predicts early relapse: A prospective study in node-negative breast cancer," Apr. 13, 2004, pp. 19-26, vol. 135—No. 4.
Jia et al. "Discovery of new human β-defensins using a genomics-based approach," Gene, 2001, pp. 211-218, vol. 263.
Johnson et al., "The molecular detection of circulating tumour cells," British Journal of Cancer, 1995, pp. 268-276, vol. 72.
Hildebrandt et al., "Reverse transcriptase-polymerase chain reaction (RT-PCR)-controlled immunomagnetic purging of breast cancer cells using the magnetic cell separation (MACS) system: A sensitive method for monitoring purging efficiency," Experimental Hematology, 1997, pp. 57-65, vol. 25.
Harder et al., "Mapping of the gene Encoding Human β-Defensi-2 (DEFB2) to Chromosome region 8p. 22-p. 23.1," Genomics, 1997, pp. 472-475, vol. 46.
Harder et al., "A peptide antibiotic from human skin," Nature, Jun. 26, 1997, pp. 861, vol. 387—No. 6636.
Guseva et al., "Death Receptor-Induced Cell Death in Prostate Cancer," Journal of Cellular Biochemistry, 2004, pp. 70-99, vol. 91.
Gleason et al., "Classification of Prostatic Carcinomas," Cancer Chemotherapy Reports, Mar. 1966, pp. 125-128, vol. 50—No. 3.
Gilbey et al., "The detection of circulating breast cancer cells in blood," Journal of Clinical Pathology, 2004, pp. 903-911, vol. 57.
Gibson et al., "Inhibition of PAX2 expression results in alternate cell death pathways in prostate cancer cells differing in p53 status," Cancer Letters, 2007, pp. 251-261, vol. 248.
Goldman et al., "Human β-Defensin-1 Is a Salt-Sensitive Antibiotic in lung That Is Inactivated in Cystic Fibrosis," Cell, 1997, pp. 553-560, vol. 88.
Ghossein et al., "Detection of Circulating Tumor Cells in Patients With Localized and Metastatic Prostatic Carcinoma: Clinical Implications," Journal of Clinical Oncology, 1995, pp. 1195-1200, vol. 13—No. 5.
Gerhard et al., "Specific Detection of Carcinoembryonic Antigen-Expressing Tumor Cells in Bone Marrow Aspirates by polymerase Chain Reaction," Journal of Clinical Oncology, 1994, pp. 725-729, vol. 12—No. 5.
Ganz et al., "Antimicrobial Peptides of Phagocytes and Epithelia," Seminars in Hematology, 1997, pp. 343-354, vol. 34—No. 4.
Gann et al., "A Prosepective Evaluation of Plasma Prostate-Specific Antigen for Detection of Prostatic Cancer," JAMA, Jan. 25, 1995, pp. 289-294, vol. 273—No. 4.
Dunn et al., "Cancer immunoediting: from immuno-surveillance to tumor escape," Nature Immunology, Nov. 2002, pp. 991-998, vol. 3—No. 11.
Dehbi et al., "The paired-box transcription factor, PAX2, positively modulates expression of the Wilms' tumor suppressor gene (WT1)," Oncogene, 1996, pp. 447-453, vol. 13.
Dearnaley et al., "Increased Detection of Mammary Carcinoma Cells in Marrow Smears Using Antisera to Epithelial Membrane Antigen," British Journal of Cancer, Jul. 1981, pp. 85-90, vol. 44—No. 1.
Khoubehi et al., "Expression of the developmental and oncogenic PAX2 gene in human prostate cancer," Journal of Urology, 2001, pp. 2115-2120, vol. 165.
Krisanaprakornkit et al., "Expression of the peptide antibiotic human beta-defensin 1 in cultured gingival epithelial cells and gingival tissue," Infection and Immunity, Sep. 1998, pp. 4222-4228, vol. 66—No. 9.
Lin et al., "Differentially expressed genes in activin-induced apoptotic LKCaP cells," Biochemical and Biophysical Research Communications, 1999, pp. 187-192, vol. 257—No. 1.
Linzmeier et al., "A 450-kb contig of defensin genes on human chromosome 8p23," Gene, 1999, pp. 205-211, VOl. 233—No. 1-2.
Liu et al. "Identifying DNA-binding sites and analyzing DNA-binding domains using a yeast selection system," Methods: A companion to Methods in Enzymology, 1993, pp. 125-137, vol. 5.
Discenza et al., "WT1 is a modifier of the Pax2 mutant phenotype: cooperation and interaction between WT1 and Pax2," Oncogene, 2003, pp. 8145-8155, vol. 22—No. 50.
Macoska et al., "Evolution of 8p loss in transformed human prostate epithelial cells," Cancer Genetics and Cytogenetics, 2004, pp. 36-43, vol. 154—No. 1.
Mansouri et al. "Pax genes and their roles in cell differentiation and development," Current Opinion in Cell Biology, 1996, pp. 851-857, vol. 8.
Margue et al., "Transcriptional modulation of the anti-apoptotic protein BCL-XL by the paired box transcription factors PAX3 and PAX3/FKHR," Oncogene, 2000, pp. 2921-2929, vol. 19—No. 25.
Mathews et al., "Production of beta-defensin antimicrobial peptides by the oral mucosa and salivary glands," Infection and Immunity, Jun. 1999, 99. 2740-2745, vol. 67—No. 6.
Mazal et al., "Expression of aquaporins and PAX-2 compared to CD10 and cytokeratin 7 in renal neoplasms: a tissue microarray study," Modern Pathology, 2005, pp. 535-540, vol. 18—No. 4.
Mazzucchelli et al., "Molecular mechanisms in prostate cancer. A review," Analytical and Quantitative Cytology and Histology, 2004, pp. 127-133, vol. 26—No. 3.
McConnell et al., "Differential regulation of the human Wilms tumor suppressor gene (WT1) promoter by two isoforms of PAX2," Oncogene, 1997, pp. 2689-2700, vol. 14—No. 22.
McNeel et al., "Immune-based therapies for prostate cancer," Immunology Letters, 2005, pp. 3-9, vol. 96.

(56) References Cited

OTHER PUBLICATIONS

Michalak et al. "Death squads enlisted by the tumor suppressor p53," Biochemical and Biophysical Research Communications, 2005, pp. 786-798, vol. 331—No. 3.

Muratovska et al. "Paired-Box genes are frequently expressed in cancer and often required for cancer cell survival," Oncogene, 2003, pp. 7989-7997, vol. 22—No. 39.

Murer et al., "Expression of nuclear transcription factor PAX2 in renal biopsies of juvenile nephronophthisis," Nephron, 2002, pp. 588-593, vol. 91—No. 4.

Nakamura, "Isolation of p53-target genes and their functional analysis," Cancer Science, 2004, pp. 7-11, vol. 95—No. 1.

Nigro et al., "B. Human p53 and CDC2Hs genes combine to inhibit the proliferation of Saccharomyces cerevisiae," Molecular and Cellular Biology, 1992, pp. 1357-1365, vol. 12.

Nishimura et al., "Effect of defensin peptides on eukaryotic cells: primary epithelial cells, fibroblasts and squamous cell carcinoma cell lines," Journal of Dermatological Science, 2004, pp. 87, vol. 36—No. 2.

O'Hara et al., "Multigene reverse transcription-PCR profiling of circulating tumor cells in hormone-refractory prostate cancer," Clinical Chemistry, 2004, pp. 826-835, vol. 50.

Ogata et al., "Genetic evidence for a novel gene(s) involved in urogenital development on 10q26," Kidney International, 2000, pp. 2281-2290, vol. 58—No. 6.

O'Neil et al., "Expression and regulation of the human beta-defensins hBD-1 and hBD-2 in intestinal epithelium," The Journal of Immunology, Dec. 15, 1999, pp. 6718-6724, vol. 163—No. 12.

Orlando, "Mapping chromosomal proteins in vivo by formaldehyde-crosslinked-chromatin immunoprecipitation," Trends in Biochemical Sciences, 2000, pp. 99-104, vol. 25.

Ostrom et al., "Reduced PAX2 gene dosage increases apoptosis and slows the progression of renal cystic disease," Developmental Biology, 2000, pp. 250-258, vol. 219—No. 2.

Palapattu et al., "Prostate carcinogenesis andinilammation: emerging insights," Carcinogenesis, 2005, pp. 1170-1181, vol. 26.

Perfettini et al., "Fatal liaisons of p53 with Bax and Bak," Nature Cell Biology, 2004, pp. 386-388, vol. 6—No. 5.

Perfettini et al., "Mitochondrial fusion and fission in the control of apoptosis," Trends in Cell Biology, 2005, pp. 179-183, vol. 15—No. 4.

Wells et al., "Characterizing transcription factor binding sites using formaldehyde crosslinking and immunoprecipitation," Methods, 2002, pp. 48-56, vol. 26.

Wilson et al., "Identification of the DNA binding site for NGFI-B by genetic selection in yeast," Science, 1991, pp. 1296-1300, vol. 252.

Prasad et al., "Homozygous and frequent deletion of proximal 8p sequences in human prostate cancers: identification of a potential tumor suppressor gene site," Genes, Chromosomes, and Cancer, 1998, pp. 255-262, vol. 23.

Raj et al., "Utilization of polymerase chain reaction technology in the detection of solid tumors," Cancer, 1998, pp. 1419-1442, vol. 82.

Shariat et al., "Early postoperative peripheral blood reverse transcription PCR assay for prostate-specific antigen is associated with prostate cancer progression in patients undergoing radical prostatectomy," Cancer Research, 2003, pp. 5874-5878, vol. 63.

Sikorski et al., "A system of shuttle vectors and yeast host strains designed for efficient manipulation of DNA in Saccharomyces cerevisiae," Genetics, 1989, pp. 19-27, vol. 122.

Soeth et al., "Comparative analysis of bone marrow and venous blood isolates from gastrointestinal cancer patients for the detection of disseminated tumor cells using reverse transcription PCR," Cancer Research, 1997, pp. 3106-3110, vol. 57.

Strasser, "The role of BH3-only proteins in the immune system," Nature Reviews Immunology, 2005, pp. 189-200, vol. 5—No. 3.

Stuart et al., "Loss of p53 function through PAX-mediated transcriptional repression," EMBO Journal, 1995, pp. 5638-5645, vol. 14—No. 22.

Tagge et al., "Paired box gene expression in Wilms' tumor," Journal of Pediatric Surgery, 1994, pp. 134-141, vol. 29—No. 2.

Takeuchi et al., "Differential effects of phthalate esters on transcriptional activities via human estrogen receptors alpha and beta, and androgen receptor," Toxicology, 2005, pp. 223-233, vol. 210—No. 2-3.

Teixeira et al., "Genomic analysis of prostate carcinoma specimens obtained via ultrasound-guided needle biopsy may be of use in preoperative decision-making," Cancer, 2004, pp. 1786-1793, vol. 101—No. 8.

Tien et al., "Altered immunity accompanies disease progression in a mouse model of prostate dysplasia," Cancer Research, 2005, pp. 2947-2955, vol. 65.

Tokino et al., "The role of p53-target genes in human cancer," Critical Reviews in Oncology/Hematology, 2000, pp. 1-6, vol. 33—No. 1.

Torres et al., "PAX-2 controls multiple steps of urogenital development," Development, 1995, pp. 4057-4065, vol. 121.

Valore et al., "Human beta-defensin-1: an antimicrobial peptide of urogenital tissues," Journal of Clinical Investigation, Apr. 15, 1998 pp. 1633-1642, vol. 101—No. 8.

Vecchione et al., "FEZ1/LZTS1 is down-regulated in high-grade bladder cancer, and its restoration suppresses tumorigenicity in transitional cell carcinoma cells," American Journal of Pathology, 2002, pp. 1345-1352, vol. 160—No. 4.

Wallin et al., "Dependence of BSAP repressor and activator functions on BSAP concentration," Science, 1998, pp. 1961-1964, vol. 279.

Wang et al., "Identification and characterization of circulating prostate carcinoma cells," Cancer, 2000, pp. 2787-2795, vol. 88.

Wang et al., "Analysis of loss of heterozygosity on chromosome 8 in human prostate carcinoma and high grade prostatic intraepithelial neoplasia," Zhonghua Nan 10 Ke Xue, 2004, pp. 26-28, 31, vol. 10—No. 1.

Donald et al., "Cancer-Specific Loss of beta-Defensin 1 in Renal and Prostatic carcinomas", Laboratory Investigation, 2003, pp. 501-505, vol. 83.

International Search Report and Written Opinion of the the International Searching Authority issued in International Patent Application No. PCT/US2009/054913 mailed Sep. 17, 2010.

Xu et al., "Crystal Structure of a Paired Domain-DNA Complex O at 2,5 A Resolution Reveals Structural Basis for Pax Developmental Mutations," Cell, Feb. 24, 1995, 639-650, vol. 80.

Yang et al., "Multiple Roles of Antimicrobial Defensins, Cathelicidins, and Eosinophil-Derived Neurotoxin in Host Defense," Annual Review of Immunology, 2004, pp. 181-215, vol. 22—No. 1.

Ylikoski, et al., "Simultaneous quantification of prostate-specific antigen and human glandular kallikrein 2 mRNA in bloodsamples from patients with prostate cancer and benign disease," Clinical Chemistry, 2002, pp. 1265-1271, vol. 48.

Yuan et al., "Pax-2 interacts with RB and reverses its repression on the promoter of Rig-1, a Robo member," Biochemical and Biophysical Research Communications, 2002, pp. 1019-1025, vol. 296—No. 4.

Zucht et al., "Human beta-defensin-1: A urinary peptide present in variant molecular forms and 30 its putative functional implication," European Journal of Medical Research, Jul. 20, 1998, pp. 315-323, vol. 3—No. 7.

Lowe et al., "A computer program for selection of oligonucleotide primers for polymerase chain reactions," Nucleic Acids Research, Dec. 18, 1989, pp. 1757, vol. 18—No. 7.

Buck et al., "Design strategies and performance of custom DNA sequencing primers," BioTechniques, Sep. 1999, pp. 528-536, vol. 27.

European Search Report issued in European Patent Application No. 08727729.9 dated Apr. 1, 2011.

International Search Report and Written Opinion of the International Searching Authority issued in International Patnet Application No. PCT/US2010/024740 mailed Oct. 27, 2010.

Bose et al., "PAX2 oncogene negatively regulates the expression of the host defense peptide human beta defensin-1 prostate cancer," Molecular Immunology, 2009, pp. 1140-1148, vol. 46.

Hurtado et al., "Regulation of ERBB2 by oestrogen receptor-PAX2 determines response to tamoxifen," Nature, Dec. 4, 2008, pp. 663-666, vol. 456.

(56) References Cited

OTHER PUBLICATIONS

Morrison et al., "Chimeric human antibody molecules: mouse antigen-binding domains with human constant region domains," Proceedings of the National Academy of Science, 1984, pp. 6851-6855, vol. 81.

Dunsche et al., "Expression profile of human defensins and antimicrobial proteins in oral tissues," Journal of Oral Pathology and Medicine, 2001, pp. 154-158, vol. 30.

Bensch et al., "hBD-1: a novel beta-defensin from human plasma," Federation of European Biochemical Societies, 1995, pp. 331-335, vol. 368.

Jatoi et al., "Breast Cancer Screening," The American Journal of Surgery, 1999, pp. 518-524, vol. 177.

Marcus et al., "Hereditary Breast Cancer," Cancer, 1996, pp. 697-709, vol. 77.

Miki et al., "A strong candidate for the breast and ovarian cancer susceptibility gene BRCA1," Science, 1994, pp. 66-71, vol. 266.

Katz et al., "Gene activity during the early phase of androgen-stimulated rat prostate regrowth," Cancer Research, 1989, pp. 5889-5894, vol. 49.

Casey "The BRCA1 and BRCA2 breast cancer genes," Current Opinion in Oncology, 1997, pp. 88-93, vol. 9.

The International Preliminary Report on Patentability issued in International Patent Application No. PCT/US2008/51168 dated Oct. 23, 2009.

Carroll et al., "p53 Oncogene Mutations in Three Human Prostate Cancer Cell Lines," The Prostate, 1993, pp. 123-134, vol. 23.

Bokhoven et al., "Molecular Characterization of Human Prostate Carcinoma Cell Lines," The Prostate, 2003, pp. 205-222, vol. 57.

Benson et al., "The staging and grading of prostatic cancer," The Prostate, 1989, pp. 261-272.

Ady et al., "Detection of HER-2/neu-positive circulating epithelial cells in prostate cancer patients," British Journal of Cancer, 2004, pp. 443-448, vol. 90.

Bals et al., "Mouse beta-defensin 1 is a salt-sensitive antimicrobial15 peptide present in epithelia of the lung and urogenital tract," Infection and Immunity, Mar. 1998, pp. 1225-1232 vol. 66—No. 3.

Bockmuhl et al., "Association of 8p23 deletions with poor survival in head and neck cancer," Otolaryngology Head Neck Surgery, 2001, pp. 451-455, vol. 124—No. 4.

Boyd et al., "Coexamination of site-specific transcription factor binding and promoter activity in living cells," Molecular and Cellular Biology, 1999, pp. 8393-8399, vol. 19.

Braida et al., "A singlenucleotide polymorphism in the human beta-defensin 1 gene is associated with 35 HIV-1 infection in Italian children," Aids, 2004, pp. 1598-1600, vol. 18.

Buttiglieri et al., "Role of PAX2 in apoptosis resistance and proinvasive phenotype of Kaposi's sarcoma cells," Journal of Biological Chemistry, 2004, pp. 4136-4143, vol. 279—No. 6.

Catalano et al., "Altered expression of androgen-receptor isoforms in human colon-cancer tissues," International Journal of Cancer, 2000, pp. 325-330; vol. 86—No. 3.

Chaib et al., "Haploinsufficiency and reduced expression of genes localized to the 8p chromosomal region in human prostate tumors," Genes, Chromosomes, and Cancer, 2003, pp. 306-313, vol. 37—No. 3.

Coultas et al., "The role of the Bcl-2 protein family in cancer," Seminars in Cancer Biology, 2003, pp. 115-123, vol. 13—No. 2.

Davies et al., "Development of an siRNA-based method for repressing specific genes in renal organ culture and its use to show that the Wt1 tumour suppressor is required for nephron differentiation," Human Molecular Genetics, Jan. 15, 2004, pp. 235-246, vol. 13—No. 2.

Dorfler et al., "C-terminal activating and inhibitory domains determine the transactivation potential of BSAP (PAX-5), PAX-2 and PAX-8," EMBO Journal, 1996, pp. 1971-1982, vol. 15—No. 8.

Dressler et al., "Pax2, a new murine paired-box-containing gene and its expression in the developing excretory system," Development, Aug. 1990, pp. 787-795, vol. 109—No. 4.

Dressler et al., "PAX2 in development and renal disease," International Journal of Developmental Biology, 1999, pp. 463-468, vol. 43—No. 5.

Dressler et al., "Pax-2, kidney development, and oncogenesis," Medical and Pediatric Oncology, 1996, pp. 440-444, vol. 27—No. 5.

Eccles et al., "PAX genes in development and disease: the role of PAX2 in urogenital tract development," International Journal of Developmental Biology, 2002, pp. 535-544, vol. 46—No. 4.

Eccles et al., "Expression of the PAX2 gene in human fetal kidney and Wilms' tumor," Cell Growth and Differentiation, 1992, pp. 279-289, vol. 3—No. 5.

Ganz, "Defensins and host defense" Science, 1999, pp. 420-421, vol. 286.

Ganz, "Immunology: Versatile Defensins," Science, 2002, pp. 977-979, vol. 298.

Ganz, "Defensins: antimicrobial peptides of vertebrates," C R Biol, 2004, pp. 539-549, vol. 327.

Fong et al., "Dendritic Cell-Based Xenoantigen Vaccination for Prostate Cancer Immunotherapy," The Journal of Immunology, 2001, pp. 7150-7156, vol. 167—No. 12.

Fonsato et al., "Expression of Pax2 in human renal tumor-derived endothelial cells sustains apoptosis resistance and angiogenesis," American Journal of Pathology, Feb. 2006, pp. 706-713, vol. 168—No. 2.

Frornont et al., "Allelic losses in localized prostate cancer: association with prognostic factors," The Journal of Urology, Oct. 2003, pp. 1394-1397, vol. 170—No. 4 Part 1.

Fuji et al., "Detection of disseminated urothelial cancer cells in peripheral venous blood by a cytokeratin 20-specific nested reverse transcriptase-polymerase chain reaction," Japanese Journal of Cancer Research, 1999, pp. 753-757, vol. 90.

Ghossein et al., "Molecular detection of micro metastases and circulating tumor cells in solid tumors," Clinical Cancer Research, 1999, pp. 1950-1960, vol. 5.

Gnarra et al., "Expression of Pax-2 in human renal cell carcinoma and growth inhibition by antisense oligonucleotides," Cancer Research, 1995, pp. 4092-4098, vol. 55—No. 18.

Gropp et al., "Epithelial defensins impair adenoviral infection: implication for adenovirus-mediated gene therapy," Hum Gene Therapy, 1999, pp. 957-964, vol. 10—No. 6.

Gunther et al., "Specific targets in tumor tissue for the delivery of 40 therapeutic genes," Current Medicinal Chemistry—Anti-Cancer Agents, 2005, pp. 157-171, vol. 5—No. 2.

Harder et al. "Isolation and characterization of human beta-defensin-3, a novel human inducible peptide antibiotic," The Journal of Biological Chemistry, Feb. 23, 2001, pp. 5707-5713, vol. 276—No. 8.

Havik et al., "A novel paired domain DNA recognition motifcan mediate PAX2 repression of gene transcription," Biochemical and Biophysical Research Communications, 1999, pp. 532-541, vol. 266—No. 2.

Hoon et al., "Detection of metastatic breast cancer by b-hCG polymerase chain reaction," International Journal of Cancer, Oct. 21, 1996, pp. 369-374, vol. 69—No. 5.

Hueber et al., "PAX2 inactivation enhances cisplatin-induced apoptosis in renal carcinoma cells," Kidney International, Apr. 2006, 1139-1145, vol. 69—No. 7.

Hugel et al., "Loss of heterozygosity (LOH), malignancy grade and clonality in microdissected prostate cancer," British Journal of Cancer, 1999, pp. 551-557, vol. 79, No. 3-4.

Ino et al., "Angiotensin II type 1 receptor expression in ovarian cancer and its correlation with tumor angiogenesis and patient survival," British Journal of Cancer, 2006, pp. 552-560, vol. 94—No. 4.

Jackers et al., "Ets-dependent regulation of target gene expression during megakaryopoiesis," Dec. 10, 2004, pp. 52183-52190, vol. 279—No. 50.

Jemal et al., "Cancer statistics," CA: A Cancer Journal for Clinicians, 2006, pp. 106-130, vol. 56.

Jemal et al., "Cancer statistics," CA: A Cancer Journal for Clinicians, 2004, pp. 8-29, vol. 54—No. 1.

(56) References Cited

OTHER PUBLICATIONS

Jia et al., "A novel murine beta -defensin expressed in tongue, esophagus, and trachea," Journal of Biological Chemistry, Oct. 27, 2000, pp. 33314-33320, vol. 275—No. 4.

Juin et al., "c-Myc functionally cooperates with Bax to induce apoptosis," Molecular and Cellular Biology, Sep. 2002, pp. 6158-6169, vol. 22—No. 17.

Kefas et al., "AMP-activated protein kinase can induce apoptosis of insulin-producing MIN6 cells through stimulation of c-Jun-N-terminal kinase," Journal of Molecular Endocrinology, 2003, pp. 151-161, vol. 30.

Kelloff et al., "Progress in chemoprevention drug development: the promise of molecular biomarkers for prevention of intraepithelial neoplasia and cancer-a plan to move forward," Clinical Cancer Research, Jun. 15, 2006, pp. 3661-3697, vol. 12—No. 12.

Isaacs et al., "Wild-type p53 suppresses growth of human prostate cancer cells containing mutant p53 alleles," Cancer Research, 1991, pp. 4716-4720, vol. 51.

\* cited by examiner

SEQUENCE LISTING

<160> NUMBER OF SEQ ID NOS: 71

<210> SEQ ID NO 1
<211> LENGTH: 5
<212> TYPE: DNA
<213> ORGANISM: Homo sapiens

<400> SEQUENCE: 1 ccttg								5

<210> SEQ ID NO 2
<211> LENGTH: 5
<212> TYPE: DNA
<213> ORGANISM: Homo sapiens

<400> SEQUENCE: 2 gttcc								5

<210> SEQ ID NO 3
<211> LENGTH: 21
<212> TYPE: RNA
<213> ORGANISM: Homo sapiens

<400> SEQUENCE: 3
auagacucga cuugacuucu u							21

<210> SEQ ID NO 4
<211> LENGTH: 21
<212> TYPE: RNA
<213> ORGANISM: Homo sapiens

<400> SEQUENCE: 4
aucuucauca cguuccucu u							21

<210> SEQ ID NO 5
<211> LENGTH: 21
<212> TYPE: RNA
<213> ORGANISM: Homo sapiens

<400> SEQUENCE: 5
guauucagca aucuuguccu u							21

<210> SEQ ID NO 6
<211> LENGTH: 21
<212> TYPE: RNA
<213> ORGANISM: Homo sapiens

<400> SEQUENCE: 6
gauuugaugu gcucugaugu u							21

<210> SEQ ID NO 7
<211> LENGTH: 20
<212> TYPE: DNA
<213> ORGANISM: Homo sapiens

<400> SEQUENCE: 7
acccgactat gttcgcctgg							20

<210> SEQ ID NO 8
<211> LENGTH: 21
<212> TYPE: DNA
<213> ORGANISM: Homo sapiens

```
<400> SEQUENCE: 8
aagctctgga tcgagtcttt g                                              21

<210> SEQ ID NO 9
<211> LENGTH: 20
<212> TYPE: DNA
<213> ORGANISM: Homo sapiens

<400> SEQUENCE: 9
atgtgtcagg cacacagacg                                                20

<210> SEQ ID NO 10
<211> LENGTH: 21
<212> TYPE: RNA
<213> ORGANISM: Homo sapiens

<400> SEQUENCE: 10
gucgagucua ucugcauccu u                                              21

<210> SEQ ID NO 11
<211> LENGTH: 21
<212> TYPE: RNA
<213> ORGANISM: Homo sapiens

<400> SEQUENCE: 11
ggaugcagau agacucgacu u                                              21

<210> SEQ ID NO 12
<211> LENGTH: 75
<212> TYPE: DNA
<213> ORGANISM: Homo sapiens
<220> FEATURE:
<221> NAME/KEY: misc_feature
<222> LOCATION: (1)..(35)
<223> OTHER INFORMATION: n is a, c, g, or t
<220> FEATURE:
<221> NAME/KEY: misc_feature
<222> LOCATION: (41)..(75)
<223> OTHER INFORMATION: n is a, c, g, or t

<400> SEQUENCE: 12
nnnnnnnnnn nnnnnnnnnn nnnnnnnnnn nnnnnccttg nnnnnnnnnn nnnnnnnnnn    60
nnnnnnnnnn nnnnn                                                     75

<210> SEQ ID NO 13
<211> LENGTH: 20
<212> TYPE: DNA
<213> ORGANISM: Homo sapiens

<400> SEQUENCE: 13
ctcccttcag ttccgtcgac                                                20

<210> SEQ ID NO 14
<211> LENGTH: 20
<212> TYPE: DNA
<213> ORGANISM: Homo sapiens

<400> SEQUENCE: 14
ctcccttcac cttggtcgac                                                20

<210> SEQ ID NO 15
<211> LENGTH: 40
<212> TYPE: DNA
<213> ORGANISM: Homo sapiens
```

```
<400> SEQUENCE: 15
actgtggcac ctcccttcag ttccgtcgac gaggttgtgc                              40

<210> SEQ ID NO 16
<211> LENGTH: 40
<212> TYPE: DNA
<213> ORGANISM: Homo sapiens

<400> SEQUENCE: 16
actgtggcac ctcccttcac cttggtcgac gaggttgtgc                              40

<210> SEQ ID NO 17
<211> LENGTH: 5
<212> TYPE: DNA
<213> ORGANISM: Homo sapiens

<400> SEQUENCE: 17 ctctg                                                                     5

<210> SEQ ID NO 18
<211> LENGTH: 20
<212> TYPE: DNA
<213> ORGANISM: Homo sapiens

<400> SEQUENCE: 18
ctcccttcac tctggtcgac                                                    20

<210> SEQ ID NO 19
<211> LENGTH: 40
<212> TYPE: DNA
<213> ORGANISM: Homo sapiens

<400> SEQUENCE: 19
actgtggcac ctcccttcac tctggtcgac gaggttgtgc                              40

<210> SEQ ID NO 20
<211> LENGTH: 20
<212> TYPE: DNA
<213> ORGANISM: Homo sapiens

<400> SEQUENCE: 20
agaagttcac ccttgactgt                                                    20

<210> SEQ ID NO 21
<211> LENGTH: 20
<212> TYPE: DNA
<213> ORGANISM: Homo sapiens

<400> SEQUENCE: 21
agaagttcac gttccactgt                                                    20

<210> SEQ ID NO 22
<211> LENGTH: 20
<212> TYPE: DNA
<213> ORGANISM: Homo sapiens

<400> SEQUENCE: 22
agaagttcac gctctactgt                                                    20

<210> SEQ ID NO 23
<211> LENGTH: 39
<212> TYPE: DNA
<213> ORGANISM: Homo sapiens
```

```
<400> SEQUENCE: 23
ttagcgatta gaagttcacc cttgactgtg gcacctccc                              39

<210> SEQ ID NO 24
<211> LENGTH: 40
<212> TYPE: DNA
<213> ORGANISM: Homo sapiens

<400> SEQUENCE: 24
gttagcgatt agaagttcac gttccactgt ggcacctccc                             40

<210> SEQ ID NO 25
<211> LENGTH: 40
<212> TYPE: DNA
<213> ORGANISM: Homo sapiens

<400> SEQUENCE: 25
gttagcgatt agaagttcac gctctactgt ggcacctccc                             40

<210> SEQ ID NO 26
<211> LENGTH: 20
<212> TYPE: DNA
<213> ORGANISM: Homo sapiens

<400> SEQUENCE: 26
actgcccatt gcccaaacac                                                   20

<210> SEQ ID NO 27
<211> LENGTH: 21
<212> TYPE: DNA
<213> ORGANISM: Homo sapiens

<400> SEQUENCE: 27
aaaatcttgc cagctttccc c                                                 21

<210> SEQ ID NO 28
<211> LENGTH: 23
<212> TYPE: DNA
<213> ORGANISM: Homo sapiens

<400> SEQUENCE: 28
gtcggttacg gagcggaccg gag                                               23

<210> SEQ ID NO 29
<211> LENGTH: 24
<212> TYPE: DNA
<213> ORGANISM: Homo sapiens

<400> SEQUENCE: 29
taacatatag acaaacgcac accg                                              24

<210> SEQ ID NO 30
<211> LENGTH: 23
<212> TYPE: DNA
<213> ORGANISM: Homo sapiens

<400> SEQUENCE: 30
gcgcttgtgt cgccattgta ttc                                               23

<210> SEQ ID NO 31
<211> LENGTH: 24
<212> TYPE: DNA
<213> ORGANISM: Homo sapiens
```

```
<400> SEQUENCE: 31
gtcacaccac agaagtaagg ttcc                                            24

<210> SEQ ID NO 32
<211> LENGTH: 23
<212> TYPE: DNA
<213> ORGANISM: Homo sapiens

<400> SEQUENCE: 32
gtcggttacg gagcggaccg gag                                             23

<210> SEQ ID NO 33
<211> LENGTH: 25
<212> TYPE: DNA
<213> ORGANISM: Homo sapiens

<400> SEQUENCE: 33
cacagagcat tggcgatctc gatgc                                           25

<210> SEQ ID NO 34
<211> LENGTH: 18
<212> TYPE: DNA
<213> ORGANISM: Homo sapiens

<400> SEQUENCE: 34
cctggcaccc agcacaat                                                   18

<210> SEQ ID NO 35
<211> LENGTH: 32
<212> TYPE: DNA
<213> ORGANISM: Homo sapiens

<400> SEQUENCE: 35
gttgcctgcc agtcgccatg agaacttcct ac                                   32

<210> SEQ ID NO 36
<211> LENGTH: 20
<212> TYPE: DNA
<213> ORGANISM: Homo sapiens

<400> SEQUENCE: 36
gccgatccac acggagtact                                                 20

<210> SEQ ID NO 37
<211> LENGTH: 32
<212> TYPE: DNA
<213> ORGANISM: Homo sapiens

<400> SEQUENCE: 37
tggccttccc tctgtaacag gtgccttgaa tt                                   32

<210> SEQ ID NO 38
<211> LENGTH: 21
<212> TYPE: RNA
<213> ORGANISM: Homo sapiens

<400> SEQUENCE: 38
gaagucaagu cgagucuauu u                                               21

<210> SEQ ID NO 39
<211> LENGTH: 21
<212> TYPE: RNA
<213> ORGANISM: Homo sapiens
```

```
<400> SEQUENCE: 39
gaggaaacgu gaugaagauu u                                              21

<210> SEQ ID NO 40
<211> LENGTH: 21
<212> TYPE: RNA
<213> ORGANISM: Homo sapiens

<400> SEQUENCE: 40
ggacaagauu gcugaauacu u                                              21

<210> SEQ ID NO 41
<211> LENGTH: 21
<212> TYPE: RNA
<213> ORGANISM: Homo sapiens

<400> SEQUENCE: 41
caucagagca caucaaaucu u                                              21

<210> SEQ ID NO 42
<211> LENGTH: 24
<212> TYPE: DNA
<213> ORGANISM: Homo sapiens

<400> SEQUENCE: 42
ccacccatgg caaattccat ggca                                           24

<210> SEQ ID NO 43
<211> LENGTH: 23
<212> TYPE: DNA
<213> ORGANISM: Homo sapiens

<400> SEQUENCE: 43
ctcaggccta tgcaaaaaga gga                                            23

<210> SEQ ID NO 44
<211> LENGTH: 23
<212> TYPE: DNA
<213> ORGANISM: Homo sapiens

<400> SEQUENCE: 44
aacctacgca cctacgtgag gag                                            23

<210> SEQ ID NO 45
<211> LENGTH: 20
<212> TYPE: DNA
<213> ORGANISM: Homo sapiens

<400> SEQUENCE: 45
gacacctgag ctgaccttgg                                                20

<210> SEQ ID NO 46
<211> LENGTH: 24
<212> TYPE: DNA
<213> ORGANISM: Homo sapiens

<400> SEQUENCE: 46
tctagacggc aggtcaggtc aacc                                           24

<210> SEQ ID NO 47
<211> LENGTH: 20
<212> TYPE: DNA
<213> ORGANISM: Homo sapiens
```

```
<400> SEQUENCE: 47
gccctccctc caaaggagac                                                    20

<210> SEQ ID NO 48
<211> LENGTH: 22
<212> TYPE: DNA
<213> ORGANISM: Homo sapiens

<400> SEQUENCE: 48
cgttcagtcc atcccatttc tg                                                 22

<210> SEQ ID NO 49
<211> LENGTH: 20
<212> TYPE: DNA
<213> ORGANISM: Homo sapiens

<400> SEQUENCE: 49
gaggaagtcc agtgtccagc                                                    20

<210> SEQ ID NO 50
<211> LENGTH: 19
<212> TYPE: DNA
<213> ORGANISM: Homo sapiens

<400> SEQUENCE: 50
tcagcagtgg agggcaatg                                                     19

<210> SEQ ID NO 51
<211> LENGTH: 23
<212> TYPE: DNA
<213> ORGANISM: Homo sapiens

<400> SEQUENCE: 51
cctctgtaac aggtgccttg aat                                                23

<210> SEQ ID NO 52
<211> LENGTH: 21
<212> TYPE: DNA
<213> ORGANISM: Homo sapiens

<400> SEQUENCE: 52
acagcaaacc tcctcacagc c                                                  21

<210> SEQ ID NO 53
<211> LENGTH: 20
<212> TYPE: DNA
<213> ORGANISM: Homo sapiens

<400> SEQUENCE: 53
tggagacgtg gcacctcttg                                                    20

<210> SEQ ID NO 54
<211> LENGTH: 24
<212> TYPE: DNA
<213> ORGANISM: Homo sapiens

<400> SEQUENCE: 54
tatgataccc gggagatcgt gatc                                               24

<210> SEQ ID NO 55
<211> LENGTH: 24
<212> TYPE: DNA
<213> ORGANISM: Homo sapiens
```

```
<400> SEQUENCE: 55
gtgcagatgc cggttcaggt actc                                              24

<210> SEQ ID NO 56
<211> LENGTH: 20
<212> TYPE: DNA
<213> ORGANISM: Homo sapiens

<400> SEQUENCE: 56
tcagccctgg actacctgca                                                   20

<210> SEQ ID NO 57
<211> LENGTH: 20
<212> TYPE: DNA
<213> ORGANISM: Homo sapiens

<400> SEQUENCE: 57
gaggtcccgg tacaccacgt                                                   20

<210> SEQ ID NO 58
<211> LENGTH: 135
<212> TYPE: PRT
<213> ORGANISM: Homo sapiens

<400> SEQUENCE: 58

Met Asp Met His Cys Lys Ala Asp Pro Phe Ser Ala Met His Arg His
1               5                   10                  15

Gly Gly Val Asn Gln Leu Gly Gly Val Phe Val Asn Gly Arg Pro Leu
            20                  25                  30

Pro Asp Val Val Arg Gln Arg Ile Val Glu Leu Ala His Gln Gly Val
        35                  40                  45

Arg Pro Cys Asp Ile Ser Arg Gln Leu Arg Val Ser His Gly Cys Val
    50                  55                  60

Ser Lys Ile Leu Gly Arg Tyr Tyr Glu Thr Gly Ser Ile Lys Pro Gly
65                  70                  75                  80

Val Ile Gly Gly Ser Lys Pro Lys Val Ala Thr Pro Lys Val Val Asp
                85                  90                  95

Lys Ile Ala Glu Tyr Lys Arg Gln Asn Pro Thr Met Phe Ala Trp Glu
            100                 105                 110

Ile Arg Asp Arg Leu Leu Ala Glu Gly Ile Cys Asp Asn Asp Thr Val
        115                 120                 125

Pro Ser Val Ser Ser Ile Asn
    130                 135

<210> SEQ ID NO 59
<211> LENGTH: 7331
<212> TYPE: DNA
<213> ORGANISM: Homo sapiens
<220> FEATURE:
<221> NAME/KEY: misc_feature
<222> LOCATION: (1)..(7331)
<223> OTHER INFORMATION: n= a, g, c, or t

<400> SEQUENCE: 59
ttcccccttt ccangagggc ctaatccgtt gcgcgcgcgc acgcggacac acacacac       60 acacacacac acacacacac acacacggcc cccatagcca ccgcaactct cagcagcagn    120
ncctagctcc tctgacccga ggccccaaga cggcgggcac aggaacccct gggacgtcct    180
ggctccaggc tggacgtagg cggaggtggc aggagtggaa aaaccaggc gggtcccacg     240 acgccccttt cctcgggtct ctccttgttt cagccagccg ctctcgcccc tggtcccctc    300
```

```
ttccctgcgt tagggtcctt tgtctccagc cacctcgcag cctgtccccg cctcggcggc    360
cctgcccttt gggcctccca gatctctctg gcgggtcccc ctgccttacc agctcccggc    420
tgtggcgcgc tcttcgcctg ctcctcacat ncacacagct gctgggagag aggaaggaa     480 aggcggncgc gccgcggatg gatccgagac ggtagatttg gtgccggctc gcaaactctg    540
ggaaacttaa ngccggttct tccgcccctc tncaactatg nccagcgcgg cccggtcgcg    600
cgcgctcacc ccgcggggac ccttccttt tcctgtattt cggctgcggc tgtttcgctt     660
cctctggtct cccagccttt ggagtggctt ccctggccct gcactccgtt cccttcggc     720 cgcccccggc tgtcgcctgc ccccaccctc cgcaggtccc acggtcgcgg cggcgatgac    780
tgtggaggta acgccgggga cgtcctgggt cagcctgcac cgtctccctc gaccacagcc    840
cgatgaggcc gcgggctccg ggccggctgc taagagagtt aatcattact tcgccagcga    900
cactcagcct cccccttccga ctctctcgcc cggcctaggg gaggagggga gggacagct    960 ggccaggtgg ggacttcggc ttcgcacaaa ccagcctctt caggcctccc agagacaggt   1020
ggtggcttct cagttccctc ggcaactctc taaggtcctc tttcttcccc tcctgtctct   1080
ccctccttcg agcctcctcc cagccaggcc tctccccacc gtctcctgtc cgctctggct   1140
ttgactgatt aactgcaggt cctgggagaa ccaactttct ttgtttggaa ccggaccgga   1200
cgggatttcc ttccctaggt ctccgccaat gggccagctc ctcccgacgg ttttggcgga   1260
ctggctgaag aggaccgcgc ctgaggccac aattaacccg gctgttggtg gtggtggttg   1320
gggggtgggc agtgaggaat ttaaccgatc ctctagcagc tgcgctggtg cagttgggag   1380
gggggtgcag gaagtgggaa tggaggagtg gcaggaggta tagacagagg gaagaacgat   1440
aaacctggac aggtgtggca tagccaatag aaggggaaac aaaataaaac aggaaggcgg   1500
cgcggggagg aatccccagt aacctttata ggattgaagt tgggtggaaa acgccacctc   1560
ctgccctacc ttagcactca gatccctcct ttacctcttt gtgaaagggt aagagttcag   1620
aaagctggcc atttactcca taatctacta gagaaatgtc tgggttttgca aaatgcctat   1680 tgattagctc catggagtag acaagacagg cgtaattatc cccattttac aggtgagaaa   1740
actgagtctc aaagaagcaa agggactgtg tatgtagtgg ctgtcacttt ttcctgtagg   1800
ctgtggggtg agtggcccct ttagctgtgc agaggtccat gggtatctag ggaggcggta   1860
caggctgtgt ccaggtctga gccagaagta ccagggcctc acggggctcc tagccctttt   1920
agcttgttct ctgttggaca ggaccttcac tcttactctc tagacctgct ggctgggttt   1980
ctcccagctt cgctattttt tcagttccct agtagagtgg cccatgggcg gtagccacct   2040
ggctggcccg tgccactaag aggcagcttt ggtggccaag tggcttgcat tgttgttgct   2100
cctcaaaggg cctgtgaagg gctgggcagg tcgcaaagac ctcttgtgag gggaaagcta   2160
gattaaaggg ggtaaggatc ctggaggata aaggccaagc acgtgcgcct ggactccaca   2220
ggaccaacag accgagcggg cggggccngc tgggagtcag gcccccgggg cttcacgcag   2280
ggagcccaaa tattgggaac aaaagcagga aaagaagagt gagagcagga gggagggagg   2340
gagcgaggaa gcagaaatta gggggtctta gatgaaaaaa aaaagaaagt agctttaggg   2400
ggaatgtgct gtggagtgtg aaattgcagc ccatggtgct ccatattgta ccagaagctc   2460
ttccaaaaaa aaaaaaaaa accatcctcc aacgtgacca gagggccagg caggggggaag   2520 ggcggggaga gaatgggaag gaggaggggg aaaggccggg caggagccgg tcaggccttt   2580
ctgcggaagg ggctgggggtg taagtttcgg ctccctggga tctgacagcc gagggtatgc   2640 gccctgggt gcgccgggac ccagagggcg agtgagcctc ggttggtcgg ctctggagtt    2700
```

```
cggttgtcag aagaactttt attttttcttt ttggtggtga cttctaaaag tgggaataat  2760
ccagaaatga agctcagctg cggagctgca gctctgttct ccctctctcc cctgcctttc  2820
tgcttctctt cccttcggac tactttctc cccttggttc taaatagctt tttccctct   2880
gaactttaat gcatttaatt tggtccgcgc tgtggggagc atttcctggg gagatgcatt  2940
taatttcgga atttctaatc ccctcccta gaccccggtc ctagctcccc tagccgctcc   3000
ccgggaagtg aaggaggaa ggcaggtccc ggccacgggg gaggggcgcg gctgggatgc    3060
tcccgcggcc ccctccgtct caccaaggct cagccgcctt cccaagctac tggaggccgg  3120
gcgcctgggc cccgggtcag ggccctgcan aagaagaga ggcaaccccc gctttctgcc    3180
ttttcttcgc ctgggcaaga aaacgctggg ccagggaact ggaaaccgga aaacaggaga  3240
aagggttnt ggaaggcanc gggagcgggt ggcagncggg gcancgggca ntggactagg    3300
tctacaccgg cacttcactt ttgcacaaca tgcccagaaa cgcatttgag agccctggag   3360
tcgcgcttgg cttggcttgg ggcgccggtg cgtgggtaca ctcgaggtcg gggtgcctat   3420
ccgccacccc gacacctaca cccagtgcag agcaggcgcg gcccagccag acaaccaggc   3480
cggcagtagc tcggcctgga gggcggaggc aaggttgggg gccgccaggc gcctgggcaa   3540
gcctggcagg gaagggagcc gagaaggcaa aggagccgag atccacaagg aagattnntt   3600
gggcagatca gatgcacaga ggcggctaat gaagcaaatc ccgagatggg tttcagagca   3660
actcccccaaa agtttatttt gcctttaaat ttccgcaggg aggcgggctc cttgtttgaa   3720
gtgtaaatgc ccctaggttg gggggtggaa gggccgcttt gaaaacacca gagagaaaag   3780
gttcatttag aggcggacgg gaaaagcaac caaccctgac aggtcggagc ccgggtagtg   3840
tttgggggttg ggtngttttc tttctttctc tttcttttcc cctttcctct tctttcttcc  3900
cttttgtgnn ttttnnttgt tttttttntn ttnttttnt ttaantggct ttcttgcttc   3960
cccccacccc tctactagac tctatagaag aaagagaaca gaaaaggggg agtcagagga   4020
gcggccagtg actggatgaa ggccagccct tcatcctgga gccccaggag aaggcagagc   4080
tttggagaaa aggggttcct aatctccagg gagcattact cttgactct ctagacccag    4140
gaatgggctg gacgctaatg gggaagcggc caggaacccg gcctggcgga agagtgagtg   4200
tccagctagt gcagtgctgg gaagacgatc ccaggagcag gggggactct caggggctac    4260
ctgggaatgg gactatcaga agggtcttta ctcctcanaa ggtgcatgtg aaggacaggt    4320
gtgtgaggac aacttccagc acacttggcg cattaagtcc ccttctctac aaaatggaaa   4380
atccttctcg cccaacatgt gaaaatgctt gttgtgggca cccacatttc atggtacttg   4440
taacatagga catgtctagc tggttctaga aaaatctgtg tctgtgtgga aggggggggg   4500
tttactcaca gctttcttcc ttcaatagtt cacacacccc gagacaaatt cctggatgac   4560
caacttggag agacctgggg caaaggttac tttagttctg agctcctcta aataaggacc   4620
ctttctcaac gttcctttca ccccagttct gggttaatta cttccagtta gtgcgtgttc   4680
gtggggttgt gaggcaaag caaacccggg agcgccatct gcaggcctca agaggaagag     4740
actgaccta gaggctaggc cctgcgtctt caacctctag cccaagggaa ccaacctgcc    4800
tagccaccca agggaagtgg ataggggct gggaggggca ggcggtgagg agtgttttcc    4860
tcccagactt taccccgcag gtggattaag cttattgggc tctggaggat acaggaggga   4920
gggcaaatgc cagggatccca gcggacccag gccccacagg agtgagaggc tcagaacctc   4980
gtcccgctga gcctggcctg agctcctcct gaggaataag ggcatcccaa aaacccgggt   5040
acaagacgcc cagtagtagt agttaggctg agtcaggcag gtgcatctct ccccatggta   5100
```

-continued

```
tctgccgccc aggctccggc cagagggagg ggagcgcgag tccgcggcgc ttccgcgggg    5160
cgcccggaac tgcagacggg ggctggagga atctcggatt cgggctgcaa gagcgctgcg    5220
caagcttcgc cgagccgccc tttcgcagac ccagggaagc ggggggaggg agcgaaggag    5280
ggagagagag ttaaaacatc agcttgaaag tgcccaagat gattttatta agaccgaggg    5340
gaaaattatt ttcatgaaag attctccccg gaatatttct tgtacttaac ccagttagga    5400
agacaaaggg cttctttctg cctggtgcgg tgcgagcgga ccccagcgag caagggagct    5460
agtgccaaag agaactgcgg aggctccggc aggagtgggg acgtcccgt ggttgcgcct    5520 cctgcgctcg ccccggatcc accgagctag cagcgggcgg cgctcagccg cgtccgcagc    5580
ctcctcttct ccccagccgg ggagagccag cctcgtctcc cacatcctct gccgccagcg    5640
acctgcagct ccgcactgtt tccctcccct gtaccccctt cccagtcacc cgagggttca    5700
gaaaccaagt cccccggctc tcccgccatc cgctgggtcc caccgaggca ggtgggtact    5760
cgccggaggt cttcagctcg attctgaacc aagcgttctg gactgccag acccggtggg    5820 caaggggact ggggaggccc tgcgcacagt cgcgtggaac gggaggggac aagacaaact    5880
gctggacact tttccgtgga atgagaagtg ggggtgcgt gggtgggaag gtacctccgg    5940
agggaaaggc caaagggaag gaccagaaag agaggaagga agagccggga aggaacggaa    6000
gggaactcag agccgagggt ggtggggttg gggctaggga tgcgcactgg gcccggggcc    6060
gcgcggccca gcgggcact ggccagtgga tggcagggct gggcgagtta gaactgagag    6120
cccggcttca cagcgcagcg cgctccgagg ccctctgtcg ttacctgaat attcattaga    6180
ctgaccgctc tttatcctta tctaacgttt atcttatcgg cgagtttcgt ttctcagtgt    6240
agttttaatc ccgggctccc attccccctc ccccggtccg ctccctccc tcctctttcc    6300 ttcgccggct gctccctccc tccctccctc ccattctccc ctcccctgcc ctccccttgc    6360
cggcaccgga gtgacaggct cggggccctc ctcgccgaag ctcggggctc cagcgctggc    6420
gaatcacaga gtggtggaat ctattgcctt tgtctgacaa gtcatccatc tcccggcgcg    6480 gggagggggga ggaggtctgg aggggggcttt gcagctttta gagagacaca caccgggagc    6540
cgaggctcca gtctccggcc gagtcttcta gcagccgcaa cccacctggg gccagcccag    6600
agctgccagc gccgctcggc tccctccctc cctcccggcc cttcggccgc ggcggcgtgc    6660
gcctgccttt tccgggggcg ggggcctggc ccgcgcgctc ccctcccgca ggcgccacct    6720
cggacatccc cgggattgct acttctctgc caacttcgcc aactcgccag cacttggaga    6780
ggcccggctc ccctcccggc gccctctgac cgccccccgcc ccgcgcgctc tccgaccacc    6840
gcctctcgga tgaacaggtt ccaggggagc tgagcgagtc gcctccccg cccagcttca    6900 gccctggctg cagctgcagc gcgagccatg cgcccccagt gcaccccggc ccggcccacc    6960
gccccggggc cattctgctg accgccagc cccgagcccc gacagtggca agttgcggct    7020
actgcggttg caagctccgg ccaacccgga ggagcccag cggggagcgc agtgttgcgc    7080 ccccgcccc cgcgcgcgcc gcagcagccg ggcgttcact catcctccct ccccaccgt    7140 ccctcccttt tctcctcaag tcctgaagtt gagtttgaga ggcgacacgg cggcggcggc    7200
cgcgctgctc ccgctcctct gcctccccat ggatatgcac tgcaaagcag ccccttctc    7260 cgcgatgcac cgtgagtacc cgcgcccggc tcctgtcccg gctcgggctc tccgtcccaa    7320
ccctgtccag t    7331
```

<210> SEQ ID NO 60
<211> LENGTH: 416

<212> TYPE: PRT
<213> ORGANISM: Homo sapiens

<400> SEQUENCE: 60

```
Met Asp Met His Cys Lys Ala Asp Pro Phe Ser Ala Met His Pro Gly
1               5                   10                  15
His Gly Gly Val Asn Gln Leu Gly Gly Val Phe Val Asn Gly Arg Pro
            20                  25                  30
Leu Pro Asp Val Val Arg Gln Arg Ile Val Glu Leu Ala His Gln Gly
        35                  40                  45
Val Arg Pro Cys Asp Ile Ser Arg Gln Leu Arg Val Ser His Gly Cys
50                  55                  60
Val Ser Lys Ile Leu Gly Arg Tyr Tyr Glu Thr Gly Ser Ile Lys Pro
65                  70                  75                  80
Gly Val Ile Gly Gly Ser Lys Pro Lys Val Ala Thr Pro Lys Val Val
                85                  90                  95
Asp Lys Ile Ala Glu Tyr Lys Arg Gln Asn Pro Thr Met Phe Ala Trp
            100                 105                 110
Glu Ile Arg Asp Arg Leu Leu Ala Glu Gly Ile Cys Asp Asn Asp Thr
        115                 120                 125
Val Pro Ser Val Ser Ser Ile Asn Arg Ile Ile Arg Thr Lys Val Gln
130                 135                 140
Gln Pro Phe His Pro Thr Pro Asp Gly Ala Gly Thr Gly Val Thr Ala
145                 150                 155                 160
Pro Gly His Thr Ile Val Pro Ser Thr Ala Ser Pro Pro Val Ser Ser
                165                 170                 175
Ala Ser Asn Asp Pro Val Gly Ser Tyr Ser Ile Asn Gly Ile Leu Gly
            180                 185                 190
Ile Pro Arg Ser Asn Gly Glu Lys Arg Lys Arg Asp Glu Val Glu Val
        195                 200                 205
Tyr Thr Asp Pro Ala His Ile Arg Gly Gly Gly Leu His Leu Val
210                 215                 220
Trp Thr Leu Arg Asp Val Ser Glu Gly Ser Val Pro Asn Gly Asp Ser
225                 230                 235                 240
Gln Ser Gly Val Asp Ser Leu Arg Lys His Leu Arg Ala Asp Thr Phe
                245                 250                 255
Thr Gln Gln Gln Leu Glu Ala Leu Asp Arg Val Phe Glu Arg Pro Ser
            260                 265                 270
Tyr Pro Asp Val Phe Gln Ala Ser Glu His Ile Lys Ser Glu Gln Gly
        275                 280                 285
Asn Glu Tyr Ser Leu Pro Ala Leu Thr Pro Gly Leu Asp Glu Val Lys
290                 295                 300
Ser Ser Leu Ser Ala Ser Thr Asn Pro Glu Leu Gly Ser Asn Val Ser
305                 310                 315                 320
Gly Thr Gln Thr Tyr Pro Val Val Thr Gly Arg Asp Met Ala Ser Thr
                325                 330                 335
Thr Leu Pro Gly Tyr Pro Pro His Val Pro Pro Thr Gly Gln Gly Ser
            340                 345                 350
Tyr Pro Thr Ser Thr Leu Ala Gly Met Val Pro Gly Ser Glu Phe Ser
        355                 360                 365
Gly Asn Pro Tyr Ser His Pro Gln Tyr Thr Ala Tyr Asn Glu Ala Trp
370                 375                 380
Arg Phe Ser Asn Pro Ala Leu Leu Ser Ser Pro Tyr Tyr Tyr Ser Ala
385                 390                 395                 400
```

Ala Pro Arg Ser Ala Pro Ala Ala Ala Ala Tyr Asp Arg His
        405                 410                 415

<210> SEQ ID NO 61
<211> LENGTH: 4276
<212> TYPE: DNA
<213> ORGANISM: Homo sapiens

<400> SEQUENCE: 61

| | | | | | |
|---|---|---|---|---|---|
| aggctccagt | ctccggccga | gtcttctcgc | agccgcaacc | cacctggggc | cagcccagag | 60 |
| ctgccagcgc | cgctcggctc | cctccctccc | tcccggccct | tcggccgcgg | cggcgtgcgc | 120 |
| ctgccttttc | cgggggcggg | ggcctggccc | gcgcgctccc | ctcccgcagg | cgccacctcg | 180 |
| gacatccccg | ggattgctac | ttctctgcca | acttcgccaa | ctcgccagca | cttggagagg | 240 |
| cccggctccc | ctcccggcgc | cctctgaccg | ccccgcccc | gcgcgctctc | cgaccaccgc | 300 |
| ctctcggatg | accaggttcc | aggggagctg | agcgagtcgc | ctcccccgcc | cagcttcagc | 360 |
| cctggctgca | gctgcagcgc | gagccatgcg | ccccagtgc | accccggccc | ggccaccgc | 420 |
| cccggggcca | ttctgctgac | cgcccagccc | cgagccccga | cagtggcaag | ttgcggctac | 480 |
| tgcagttgca | agctccggcc | aacccggagg | agccccagcg | gggagcgcag | tgttgcgccc | 540 |
| ccgcccccg | cgcgccccgc | agcagccggg | cgttcactca | tcctccctcc | cccaccgtcc | 600 |
| ctccctttc | tcctcaagtc | ctgaagttga | gtttgagagg | cgacacggcg | gcggcggccg | 660 |
| cgctgctccc | gctcctctgc | ctcccatgg | atatgcactg | caaagcagac | cccttctccg | 720 |
| cgatgcaccc | agggcacggg | ggtgtgaacc | agctcggggg | ggtgtttgtg | aacggccggc | 780 |
| ccctacccga | cgtggtgagg | cagcgcatcg | tggagctggc | ccaccagggt | gtgcggccct | 840 |
| gtgacatctc | ccggcagctg | cgggtcagcc | acggctgtgt | cagcaaaatc | ctgggcaggt | 900 |
| actacgagac | cggcagcatc | aagccgggtg | tgatcggtgg | ctccaagccc | aaagtggcga | 960 |
| cgcccaaagt | ggtggacaag | attgctgaat | acaaacgaca | gaacccgact | atgttcgcct | 1020 |
| gggagattcg | agaccggctc | ctggccgagg | gcatctgtga | caatgacaca | gtgcccagcg | 1080 |
| tctcttccat | caacagaatc | atccggacca | agttcagca | gcctttccac | ccaacgccgg | 1140 |
| atggggctgg | gacaggagtg | accgcccctg | gccacaccat | tgttcccagc | acggcctccc | 1200 |
| ctcctgtttc | cagcgcctcc | aatgacccag | tgggatccta | ctccatcaat | gggatcctgg | 1260 |
| ggattcctcg | ctccaatggt | gagaagagga | aacgtgatga | agttgaggta | tacactgatc | 1320 |
| ctgcccacat | tagaggaggt | ggaggtttgc | atctggtctg | gactttaaga | gatgtgtctg | 1380 |
| agggctcagt | ccccaatgga | gattcccaga | gtggtgtgga | cagtttgcgg | aagcacttgc | 1440 |
| gagctgacac | cttcacccag | cagcagctgg | aagctttgga | tcgggtcttt | gagcgtcctt | 1500 |
| cctaccctga | cgtcttccag | gcatcagagc | acatcaaatc | agaacagggg | aacgagtact | 1560 |
| ccctcccagc | cctgacccct | gggcttgatg | aagtcaagtc | gagtctatct | gcatccacca | 1620 |
| accctgagct | gggcagcaac | gtgtcaggca | cacagacata | cccagttgtg | actggtcgtg | 1680 |
| acatggcgag | caccactctg | cctggttacc | ccctcacgt | gccccccact | ggccagggaa | 1740 |
| gctaccccac | ctccaccctg | gcaggaatgg | tgcctgggag | cgagttctcc | ggcaacccgt | 1800 |
| acagccaccc | ccagtacacg | gcctacaacg | aggcttggag | attcagcaac | cccgccttac | 1860 |
| taagttcccc | ttattattat | agtgccgccc | ccggtccgc | cctgccgct | gctgccgctg | 1920 |
| cctatgaccg | ccactagtta | ccgcggggac | cacatcaagc | ttcaggccga | cagcttcggc | 1980 |
| ctccacatcg | tccccgtctg | accccacccc | ggagggaggg | aggaccgacg | cgacgcgatg | 2040 |
| cctcccggcc | accgccccag | cctcaccca | tcccacgacc | cccgcaaccc | ttcacatcac | 2100 |

```
cccctcgaa ggtcggacag gacgggtgga gccgtgggcg ggaccctcag gcccgggccc    2160
gccgccccca gcccgcctg ccgcccctcc ccgcctgcct ggactgcgcg gcgccgtgag    2220
ggggattcgg cccagctcgt cccggcctcc accaagccag ccccgaagcc cgccagccac   2280
cctgccggac tcgggcgcga cctgctggcg cgcgccggat gtttctgtga cacacaatca   2340
gcgcggaccg cagcgcggcc cagccccggg cacccgcctc ggacgctcgg gcgccaggag   2400
gcttcgctgg aggggctggg ccaaggagat taagaagaaa acgactttct gcaggaggaa   2460
gagcccgctg ccgaatccct gggaaaaatt cttttccccc agtgccagcc ggactgccct   2520
cgccttccgg gtgtgccctg tcccagaaga tggaatgggg gtgtgggggt ccggctctag   2580
gaacgggctt tggggggcgtc aggtctttcc aaggttggga cccaaggatc gggggggccca  2640 gcagcccgca ccgatcgagc cggactctcg gctcttcact gctcctcctg gcctgcctag   2700
ttccccaggg cccggcacct cctgctgcga gacccggctc tcagccctgc cttgcccta    2760 cctcagcgtc tcttccacct gctggcctcc cagtttcccc tcctgccagt ccttcgcctg   2820
tcccttgacg ccctgcatcc tcctccctga ctcgcagccc catcggacgc tctcccggga   2880
ccgccgcagg accagtttcc atagactgcg gactggggtc ttcctccagc agttacttga   2940
tgccccctcc cccgacacag actctcaatc tgccggtggt aagaaccggt tctgagctgg   3000
cgtctgagct gctgcgggt ggaagtgggg ggctgcccac tccactcctc ccatcccctc    3060
ccagcctcct cctccggcag gaactgaaca gaaccacaaa aagtctacat ttatttaata   3120
tgatggtctt tgcaaaaagg aacaaaacaa cacaaaagcc caccaggctg ctgctttgtg   3180
gaaagacggt gtgtgtcgtg tgaaggcgaa accggtgta cataacccct ccccctccgc    3240
cccgccccgc ccggccccgt agagtccctg tcgcccgccg ccctgcctg tagatacgcc    3300 ccgctgtctg tgctgtgaga gtcgccgctc gctgggggg aaggggggga cacagctaca    3360
cgcccattaa agcacagcac gtcctggggg aggggggcat tttttatgtt acaaaaaaaa   3420
attacgaaag aaaagaaatc tctatgcaaa atgacgaaca tggtcctgtg gactcctctg   3480
gcctgttttg ttggctcttt ctctgtaatt ccgtgttttc gcttttcct ccctgccct    3540 ctctccctct gccctctct cctctccgct tctctccccc tctgtctctg tctctctccg    3600
tctctgtcgc tcttgtctgt ctgtctctgc tctttcctcg gcctctctcc ccagacctgg   3660
cccggccgcc ctgtctccgc aggctagatc cgaggtggca gctccagccc ccgggctcgc   3720 ccctcgcgg gcgtgccccg cgcgcccgg gcggccgaag gccgggccgc ccgtcccgc     3780 cccgtagttg ctctttcggt agtggcgatg cgccctgcat gtctcctcac ccgtggatcg   3840
tgacgactcg aaataacaga aacaaagtca ataaagtgaa aataaataaa aatccttgaa   3900
caaatccgaa aaggcttgga gtcctcgccc agatctctct cccctgcgag ccctttttat   3960
ttgagaagga aaaagagaaa agagaatcgt ttaagggaac ccggcgccca gcaggctcc    4020 agtgcccga acggggcggc gagggcggcg agggcgccga ggtccggccc atcccagtcc    4080 tgtgggctg gccgggcaga gaccccggac ccaggcccag gcctaacctg ctaaatgtcc    4140
ccggacggtt ctggtctcct cggccacttt cagtgcgtcg gttcgttttg attcttttc    4200 ttttgtgcac ataagaaata aataataata ataaataaag aataaaattt tgtatgtcaa   4260
aaaaaaaaaa aaaaaa                                                   4276

<210> SEQ ID NO 62
<211> LENGTH: 393
<212> TYPE: PRT
<213> ORGANISM: Homo sapiens
```

<400> SEQUENCE: 62

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ile Asn Arg Ile Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
        355                 360                 365

Leu Ser Ser Pro Tyr Tyr Tyr Ser Ala Ala Pro Arg Ser Ala Pro Ala
370                 375                 380

Ala Ala Ala Ala Ala Tyr Asp Arg His
385                 390
```

<210> SEQ ID NO 63

<211> LENGTH: 4207
<212> TYPE: DNA
<213> ORGANISM: Homo sapiens

<400> SEQUENCE: 63

| | |
|---|---|
| aggctccagt ctccggccga gtcttctcgc agccgcaacc cacctggggc cagcccagag | 60 |
| ctgccagcgc cgctcggctc cctccctccc tcccggccct tcggccgcgg cggcgtgcgc | 120 |
| ctgccttttc cggggcggg ggcctggccc gcgcgctccc ctcccgcagg cgccacctcg | 180 |
| gacatccccg ggattgctac ttctctgcca acttcgccaa ctcgccagca cttggagagg | 240 |
| cccggctccc ctcccggcgc cctctgaccg ccccgcccc gcgcgctctc cgaccaccgc | 300 |
| ctctcggatg accaggttcc aggggagctg agcgagtcgc ctcccccgcc cagcttcagc | 360 |
| cctggctgca gctgcagcgc gagccatgcg ccccagtgc accccggccc ggcccaccgc | 420 |
| cccggggcca ttctgctgac cgcccagccc cgagccccga cagtggcaag ttgcggctac | 480 |
| tgcagttgca agctccggcc aaccggagg agccccagcg gggagcgcag tgttgcgccc | 540 |
| cccgccccg cgcgcccgc agcagccggg cgttcactca tcctccctcc cccaccgtcc | 600 |
| ctccctttc tcctcaagtc ctgaagttga gtttgagagg cgacacgcg gcggcggccg | 660 |
| cgctgctccc gctcctctgc ctccccatgg atatgcactg caaagcagac cccttctccg | 720 |
| cgatgcaccc agggcacggg ggtgtgaacc agctcggggg ggtgtttgtg aacggccggc | 780 |
| ccctacccga cgtggtgagg cagcgcatcg tggagctggc ccaccagggt gtgcggccct | 840 |
| gtgacatctc ccggcagctg cgggtcagcc acggctgtgt cagcaaaatc ctgggcaggt | 900 |
| actacgagac cggcagcatc aagccgggtg tgatcggtgg ctccaagccc aaagtggcga | 960 |
| cgcccaaagt ggtggacaag attgctgaat acaaacgaca gaacccgact atgttcgcct | 1020 |
| gggagattcg agaccggctc ctggccgagg gcatctgtga caatgacaca gtgcccagcg | 1080 |
| tctcttccat caacagaatc atccggacca aagttcagca gcctttccac ccaacgccgg | 1140 |
| atggggctgg acaggagtg accgcccctg gccacaccat tgttcccagc acggcctccc | 1200 |
| ctcctgtttc cagcgcctcc aatgacccag tgggatccta ctccatcaat gggatcctgg | 1260 |
| ggattcctcg ctccaatggt gagaagagga acgtgatga agatgtgtct gagggctcag | 1320 |
| tccccaatgg agattcccag agtggtgtgg acagtttgcg gaagcacttg cgagctgaca | 1380 |
| ccttcaccca gcagcagctg gaagctttgg atcgggtctt tgagcgtcct tcctaccctg | 1440 |
| acgtcttcca ggcatcagag cacatcaaat cagaacaggg gaacgagtac tccctcccag | 1500 |
| ccctgacccc tgggcttgat gaagtcaagt cgagtctatc tgcatccacc aaccctgagc | 1560 |
| tgggcagcaa cgtgtcaggc acacagacat acccagttgt gactggtcgt gacatggcga | 1620 |
| gcaccactct gctggttac ccccctcacg tgccccccac tggccaggga agctaccca | 1680 |
| cctccaccct ggcaggaatg gtgcctggga gcgagttctc cggcaacccg tacagccacc | 1740 |
| cccagtacac ggcctacaac gaggcttgga gattcagcaa cccccgcctta ctaagttccc | 1800 |
| cttattatta tagtgccgcc cccggtccg ccctgccgc tgctgccgct gcctatgacc | 1860 |
| gccactagtt accgcgggga ccacatcaag cttcaggccg acagcttcgg cctccacatc | 1920 |
| gtccccgtct gaccccaccc cggagggagg aggaccgac gcgacgcgat gcctcccggc | 1980 |
| caccgcccca gcctcacccc atcccacgac ccccgcaacc cttcacatca ccccctcga | 2040 |
| aggtcggaca ggacgggtgg agccgtgggc gggaccctca ggcccgggcc cgccgccccc | 2100 |
| agccccgcct gccgccctc cccgcctgcc tggactgcgc ggcgccgtga gggggattcg | 2160 |
| gcccagctcg tcccggcctc caccaagcca gccccgaagc ccgccagcca ccctgccgga | 2220 |

-continued

```
ctcgggcgcg acctgctggc gcgcgccgga tgtttctgtg acacacaatc agcgcggacc    2280
gcagcgcggc ccagcccgg gcacccgcct cggacgctcg ggcgccagga ggcttcgctg     2340
gaggggctgg gccaaggaga ttaagaagaa aacgactttc tgcaggagga agagcccgct    2400
gccgaatccc tggaaaaat tcttttcccc cagtgccagc cggactgccc tcgccttccg     2460
ggtgtgccct gtcccagaag atggaatggg ggtgtggggg tccggctcta ggaacgggct    2520
ttgggggcgt caggtctttc caaggttggg acccaaggat cggggggccc agcagcccgc    2580
accgatcgag ccggactctc ggctcttcac tgctcctcct ggcctgccta gttccccagg    2640
gcccggcacc tcctgctgcg agacccggct ctcagccctg ccttgcccct acctcagcgt    2700
ctcttccacc tgctggcctc ccagtttccc ctcctgccag tccttcgcct gtcccttgac    2760
gccctgcatc ctcctccctg actcgcagcc catcggacg ctctcccggg accgccgcag     2820
gaccagtttc catagactgc ggactggggt cttcctccag cagttacttg atgccccctc    2880
ccccgacaca gactctcaat ctgccggtgg taagaaccgg ttctgagctg gcgtctgagc    2940
tgctgcgggg tggaagtggg gggctgccca ctccactcct cccatcccct cccagcctcc    3000
tcctccggca ggaactgaac agaaccacaa aaagtctaca tttatttaat atgatggtct    3060
ttgcaaaaag gaacaaaaca acacaaaagc ccaccaggct gctgctttgt ggaaagacgg    3120
tgtgtgtcgt gtgaaggcga aacccggtgt acataacccc tcccctccg ccccgccccg     3180 cccggccccg tagagtccct gtcgcccgcc ggccctgcct gtagatacgc cccgctgtct    3240
gtgctgtgag agtcgccgct cgctggggg gaagggggg acacagctac acgcccatta     3300
aagcacagca cgtcctgggg gaggggggca tttttatgt tacaaaaaaa aattacgaaa     3360
gaaaagaaat ctctatgcaa aatgacgaac atggtcctgt ggactcctct ggcctgtttt    3420
gttggctctt tctctgtaat tccgtgtttt cgcttttcc tccctgcccc tctctcccc     3480 tgccctctc tcctctccgc ttctctcccc ctctgtctct gtctctctcc gtctctgtcg     3540
ctcttgtctg tctgtctctg ctcttcctc ggcctctctc cccagacctg gcccggccgc     3600
cctgtctccg caggctagat ccgaggtggc agctccagcc ccgggctcg ccccctcgcg     3660 ggcgtgcccc gcgcgccccg ggcggccgaa ggccgggccg ccccgtcccg ccccgtagtt    3720
gctctttcgg tagtggcgat gcgccctgca tgtctcctca cccgtggatc gtgacgactc    3780
gaaataacag aaacaaagtc aataaagtga aataaataa aaatccttga acaaatccga     3840
aaaggcttgg agtcctcgcc cagatctctc tcccctgcga gcccttttta tttgagaagg    3900
aaaaagagaa aagagaatcg tttaaggaa cccggcgccc agccaggctc cagtggcccg     3960
aacggggcgg cgagggcggc gagggcgccg aggtccggcc catcccagtc ctgtggggct    4020
ggccgggcag agaccccgga cccaggccca ggcctaacct gctaaatgtc cccgacggt     4080 tctggtctcc tcggccactt tcagtgcgtc ggttcgtttt gattcttttt cttttgtgca    4140
cataagaaat aaataataat aataaataaa gaataaaatt ttgtatgtca aaaaaaaaa    4200 aaaaaaa                                                              4207
```

<210> SEQ ID NO 64
<211> LENGTH: 396
<212> TYPE: PRT
<213> ORGANISM: Homo sapiens

<400> SEQUENCE: 64

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
```

```
                20                  25                  30
Leu Pro Asp Val Val Arg Gln Arg Ile Val Glu Leu Ala His Gln Gly
                35                  40                  45

Val Arg Pro Cys Asp Ile Ser Arg Gln Leu Arg Val Ser His Gly Cys
 50                  55                  60

Val Ser Lys Ile Leu Gly Arg Tyr Tyr Glu Thr Gly Ser Ile Lys Pro
 65                  70                  75                  80

Gly Val Ile Gly Gly Ser Lys Pro Lys Val Ala Thr Pro Lys Val Val
                 85                  90                  95

Asp Lys Ile Ala Glu Tyr Lys Arg Gln Asn Pro Thr Met Phe Ala Trp
                100                 105                 110

Glu Ile Arg Asp Arg Leu Leu Ala Glu Gly Ile Cys Asp Asn Asp Thr
                115                 120                 125

Val Pro Ser Val Ser Ser Ile Asn Arg Ile Ile Arg Thr Lys Val Gln
                130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
                180                 185                 190

Ile Pro Arg Ser Asn Gly Glu Lys Arg Lys Arg Asp Glu Asp Val Ser
                195                 200                 205

Glu Gly Ser Val Pro Asn Gly Asp Ser Gln Ser Gly Val Asp Ser Leu
                210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
                260                 265                 270

Leu Thr Pro Gly Leu Asp Glu Val Lys Ser Ser Leu Ser Ala Ser Thr
                275                 280                 285

Asn Pro Glu Leu Gly Ser Asn Val Ser Gly Thr Gln Thr Tyr Pro Val
                290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Glu Ala Ala Val Gly Pro Ser Ser Ser Leu Met Ser
                340                 345                 350

Lys Pro Gly Arg Lys Leu Ala Glu Val Pro Pro Cys Val Gln Pro Thr
                355                 360                 365

Gly Ala Ser Ser Pro Ala Thr Arg Thr Ala Thr Pro Ser Thr Arg Pro
                370                 375                 380

Thr Thr Arg Leu Gly Asp Ser Ala Thr Pro Pro Tyr
385                 390                 395

<210> SEQ ID NO 65
<211> LENGTH: 4290
<212> TYPE: DNA
<213> ORGANISM: Homo sapiens

<400> SEQUENCE: 65
aggctccagt ctccggccga gtcttctcgc agccgcaacc cacctggggc cagcccagag    60
```

| | |
|---|---|
| ctgccagcgc cgctcggctc cctccctccc tcccggccct tcggccgcgg cggcgtgcgc | 120 |
| ctgccttttc cggggcggg ggcctggccc gcgcgctccc ctcccgcagg cgccacctcg | 180 |
| gacatccccg ggattgctac ttctctgcca acttcgccaa ctcgccagca cttggagagg | 240 |
| cccggctccc ctcccggcgc cctctgaccg ccccccgccc gcgcgctctc cgaccaccgc | 300 |
| ctctcggatg accaggttcc aggggagctg agcgagtcgc ctcccccgcc cagcttcagc | 360 |
| cctggctgca gctgcagcgc gagccatgcg cccccagtgc accccggccc ggccaccgc | 420 |
| cccggggcca ttctgctgac cgcccagccc cgagccccga cagtggcaag ttgcggctac | 480 |
| tgcagttgca agctccggcc aacccggagg agccccagcg gggagcgcag tgttgcgccc | 540 |
| cccgcccccg cgcgcccgc agcagccggg cgttcactca tcctccctcc cccaccgtcc | 600 |
| ctccctttc tcctcaagtc ctgaagttga gtttgagagg cgacacggcg gcggcggccg | 660 |
| cgctgctccc gctcctctgc ctccccatgg atatgcactg caaagcagac cccttctccg | 720 |
| cgatgcaccc agggcacggg ggtgtgaacc agctcggggg ggtgtttgtg aacggccggc | 780 |
| ccctacccga cgtggtgagg cagcgcatcg tggagctggc ccaccagggt gtgcggccct | 840 |
| gtgacatctc ccggcagctg cgggtcagcc acggctgtgt cagcaaaatc ctgggcaggt | 900 |
| actacgagac cggcagcatc aagccgggtg tgatcggtgg ctccaagccc aaagtggcga | 960 |
| cgcccaaagt ggtggacaag attgctgaat acaaacgaca gaacccgact atgttcgcct | 1020 |
| gggagattcg agaccggctc ctggccgagg gcatctgtga caatgacaca gtgcccagcg | 1080 |
| tctcttccat caacagaatc atccggacca aagttcagca gcctttccac ccaacgccgg | 1140 |
| atggggctgg acaggagtg accgcccctg ccacaccat tgttcccagc acggcctccc | 1200 |
| ctcctgtttc cagcgcctcc aatgacccag tgggatccta ctccatcaat gggatcctgg | 1260 |
| ggattcctcg ctccaatggt gagaagagga acgtgatga agatgtgtct gagggctcag | 1320 |
| tccccaatgg agattcccag agtggtgtgg acagtttgcg gaagcacttg cgagctgaca | 1380 |
| ccttcaccca gcagcagctg gaagctttgg atcgggtctt tgagcgtcct tcctacccgt | 1440 |
| acgtcttcca ggcatcagag cacatcaaat cagaacaggg gaacgagtac tcccctcccag | 1500 |
| ccctgacccc tgggcttgat gaagtcaagt cgagtctatc tgcatccacc aaccctgagc | 1560 |
| tgggcagcaa cgtgtcaggc acacagacat acccagttgt gactggtcgt gacatggcga | 1620 |
| gcaccactct gcctggttac cccctcacg tgccccccac tggccaggga agctacccca | 1680 |
| cctccaccct ggcaggaatg gtgcctgagg ctgcagttgg tccctcatcc tccctcatga | 1740 |
| gcaagccggg gaggaagctt gcagaagtgc cccttgtgt gcaacccact ggagcgagtt | 1800 |
| ctccggcaac ccgtacagcc accccagta cacggcctac aacgaggctt ggagattcag | 1860 |
| caaccccgcc ttactaagtt ccccttatta ttatagtgcc gcccccggt ccgcccctgc | 1920 |
| cgctgctgcc gctgcctatg accgccacta gttaccgcgg ggaccacatc aagcttcagg | 1980 |
| ccgacagctt cggcctccac atcgtccccg tctgacccca ccccggaggg agggaggacc | 2040 |
| gacgcgacgc gatgcctccc ggccaccgcc ccagcctcac cccatccac gaccccccgca | 2100 |
| acccttcaca tcacccccct cgaaggtcgg acaggacggg tggagccgtg ggcgggaccc | 2160 |
| tcaggcccgg gccgccgcc cccagccccg cctgccgccc ctccccgcct gcctggactg | 2220 |
| cgcggcgccg tgaggggat tcggcccagc tcgtcccgga ctccaccaag ccagcccga | 2280 |
| agcccgccag ccaccctgcc ggactcgggc gcgacctgct ggcgcgcgcc ggatgtttct | 2340 |
| gtgacacaca atcagcgcgg accgcagcgc ggcccagccc cgggcacccg cctcggacgc | 2400 |
| tcgggcgcca ggaggcttcg ctggaggggc tgggccaagg agattaagaa gaaaacgact | 2460 |

```
ttctgcagga ggaagagccc gctgccgaat ccctgggaaa aattcttttc ccccagtgcc     2520
agccggactg ccctcgcctt ccgggtgtgc cctgtcccag aagatggaat ggggtgtgg      2580 gggtccggct ctaggaacgg gctttggggg cgtcaggtct ttccaaggtt gggacccaag     2640 gatcggggg cccagcagcc cgcaccgatc gagccggact ctcggctctt cactgctcct     2700
cctggcctgc ctagttcccc agggcccggc acctcctgct gcgagacccg gctctcagcc     2760
ctgccttgcc cctacctcag cgtctcttcc acctgctggc ctcccagttt ccctcctgc     2820 cagtccttcg cctgtccctt gacgcccgc atcctcctcc ctgactcgca gccccatcgg     2880
acgctctccc gggaccgccg caggaccagt ttccatagac tgcggactgg ggtcttcctc     2940
cagcagttac ttgatgcccc ctcccccgac acagactctc aatctgccgg tggtaagaac     3000
cggttctgag ctggcgtctg agctgctgcg gggtggaagt ggggggctgc ccactccact     3060
cctcccatcc cctcccagcc tcctcctccg gcaggaactg aacagaacca caaaagtct     3120 acatttattt aatatgatgg tctttgcaaa aggaacaaa acaacacaaa agcccaccag     3180
gctgctgctt tgtggaaaga cggtgtgtgt cgtgtgaagg cgaaacccgg tgtacataac     3240 ccctcccct ccgccccgcc ccgcccggcc ccgtagagtc cctgtcgccc gccggccctg     3300
cctgtagata cgccccgctg tctgtgctgt gagagtcgcc gctcgctggg ggaaggg       3360 gggacacagc tacacgccca ttaaagcaca gcacgtcctg ggggaggggg cattttta     3420 tgttacaaaa aaaattacg aaagaaaaga aatctctatg caaatgacg aacatggtcc     3480 tgtggactcc tctggcctgt tttgttggct ctttctctgt aattccgtgt tttcgctttt     3540
tcctccctgc ccctctctcc ctctgcccct ctctcctctc cgcttctctc cccctctgtc     3600
tctgtctctc tccgtctctg tgctcttgt ctgtctgtct ctgctctttc ctcggcctct     3660
ctccccagac ctggcccggc cgccctgtct ccgcaggcta gatccgaggt ggcagctcca     3720
gcccccgggc tcgcccctc gcgggcgtgc ccgcgcgcc ccgggcggcc gaaggccggg     3780
ccgccccgtc ccgccccgta gttgctcttt cggtagtggc gatgcgccct gcatgtctcc     3840 tcaccgtgg atcgtgacga ctcgaaataa cagaaacaaa gtcaataaag tgaaaataaa     3900
taaaaatcct tgaacaaatc cgaaaaggct tggagtcctc gcccagatct ctctcccctg     3960
cgagcccttt ttattgaga aggaaaaaga gaaaagagaa tcgtttaagg gaacccggcg     4020
cccagccagg ctccagtggc ccgaacgggg cggcgagggc ggcgagggcg ccgaggtccg     4080
gcccatccca gtcctgtggg gctggccggg cagagacccc ggaccaggc ccaggcctaa     4140 cctgctaaat gtccccggac ggttctggtc tcctcggcca ctttcagtgc gtcggttcgt     4200
tttgattctt tttcttttgt gcacataaga aataaataat aataataaat aagaataaa    4260 attttgtatg tcaaaaaaaa aaaaaaaaa                                       4290
```

<210> SEQ ID NO 66
<211> LENGTH: 408
<212> TYPE: PRT
<213> ORGANISM: Homo sapiens

<400> SEQUENCE: 66

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

-continued

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
    210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
    290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
        355                 360                 365

Leu Met Pro Pro Gly Pro Pro Leu Pro Leu Pro Leu Pro Leu Pro Met
    370                 375                 380

Thr Ala Thr Ser Tyr Arg Gly Asp His Ile Lys Leu Gln Ala Asp Ser
385                 390                 395                 400

Phe Gly Leu His Ile Val Pro Val
                405

<210> SEQ ID NO 67
<211> LENGTH: 4188
<212> TYPE: DNA
<213> ORGANISM: Homo sapiens

<400> SEQUENCE: 67
aggctccagt ctccggccga gtcttctcgc agccgcaacc cacctggggc cagcccagag      60
ctgccagcgc cgctcggctc cctccctccc tccggcccct tcggccgcgg cggcgtgcgc     120

```
ctgccttttc cggggggcggg ggcctggccc gcgcgctccc ctcccgcagg cgccacctcg    180
gacatccccg ggattgctac ttctctgcca acttcgccaa ctcgccagca cttggagagg    240
cccggctccc ctcccggcgc cctctgaccg ccccgcccc gcgcgctctc cgaccaccgc     300
ctctcggatg accaggttcc aggggagctg agcgagtcgc ctcccccgcc cagcttcagc    360
cctggctgca gctgcagcgc gagccatgcg cccccagtgc accccggccc ggcccaccgc    420
cccggggcca ttctgctgac cgcccagccc cgagccccga cagtggcaag ttgcggctac    480
tgcagttgca agctccggcc aaccggagg agccccagcg gggagcgcag tgttgcgccc     540
cccgcccccg cgcgccccgc agcagccggg cgttcactca tcctccctcc cccaccgtcc    600
ctcccttttc tcctcaagtc ctgaagttga gtttgagagg cgacacgcg gcggcggccg     660
cgctgctccc gctcctctgc ctcccatgg atatgcactg caaagcagac cccttctccg     720
cgatgcaccc agggcacggg ggtgtgaacc agctcggggg ggtgtttgtg aacggccggc    780
ccctacccga cgtggtgagg cagcgcatcg tggagctggc ccaccagggt gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct   1020
gggagattcg agaccggctc ctggccgagg gcatctgtga caatgacaca gtgcccagcg   1080
tctcttccat caacagaatc atccggacca agttcagca gcctttccac ccaacgccgg    1140
atggggctgg gacaggagtg accgcccctg gccacaccat tgttcccagc acggcctccc   1200
ctcctgtttc cagcgcctcc aatgacccag tgggatccta ctccatcaat gggatcctgg   1260
ggattcctcg ctccaatggt gagaagagga acgtgatga agatgtgtct gagggctcag    1320
tccccaatgg agattcccag agtggtgtgg acagtttgcg gaagcacttg cgagctgaca   1380
ccttcaccca gcagcagctg gaagctttgg atcgggtctt tgagcgtcct tcctaccctg   1440
acgtcttcca ggcatcagag cacatcaaat cagaacaggg gaacgagtac tccctcccag   1500
ccctgacccc tgggcttgat gaagtcaagt cgagtctatc tgcatccacc aaccctgagc   1560
tgggcagcaa cgtgtcaggc acacagacat acccagttgt gactggtcgt gacatggcga   1620
gcaccactct gcctggttac cccccctcacg tgcccccac tggccaggga agctacccca   1680
cctccaccct ggcaggaatg gtgcctggga gcgagttctc cggcaacccg tacagccacc   1740
cccagtacac ggcctacaac gaggcttgga gattcagcaa cccgcccta ctaatgccgc    1800
cccccggtcc gccctgccg ctgctgccgc tgcctatgac cgccactagt taccgcgggg    1860
accacatcaa gcttcaggcc gacagcttcg gcctccacat cgtccccgtc tgaccccacc   1920
ccggagggag ggaggaccga cgcgacgcga tgcctcccgg ccaccgcccc agcctcaccc   1980
catcccacga cccccgcaac ccttcacatc ccccctcg aaggtcggac aggacgggtg      2040
gagccgtggg cgggacctc aggcccgggc ccgccgcccc cagccccgcc tgccgccct     2100
ccccgcctgc ctggactgcg cggcgccgtg aggggattc ggcccagctc gtcccggcct    2160
ccaccaagcc agccccgaag cccgccagcc accctgccgg actcgggcgc gacctgctgg   2220
cgcgcgccgg atgtttctgt gacacacaat cagcgcggac cgcagcgcgg cccagccccg   2280
ggcacccgcc tcggacgctc gggcgccagg aggcttcgct ggaggggctg ggccaaggag   2340
attaagaaga aaacgacttt ctgcaggagg aagagcccgc tgccgaatcc ctgggaaaaa   2400
ttcttttccc ccagtgccag ccggactgcc ctcgccttcc gggtgtgccc tgtcccagaa   2460
gatggaatgg gggtgtgggg gtccggctct aggaacgggc tttgggggcg tcaggtctt   2520
```

-continued

```
ccaaggttgg gacccaagga tcgggggggcc cagcagcccg caccgatcga gccggactct    2580
cggctcttca ctgctcctcc tggcctgcct agttccccag ggcccggcac ctcctgctgc    2640
gagacccggc tctcagccct gccttgcccc tacctcagcg tctcttccac ctgctggcct    2700
cccagttttcc cctcctgcca gtccttcgcc tgtcccttga cgccctgcat cctcctccct    2760
gactcgcagc cccatcggac gctctcccgg gaccgccgca ggaccagttt ccatagactg    2820
cggactgggg tcttcctcca gcagttactt gatgccccct cccccgacac agactctcaa    2880
tctgccggtg gtaagaaccg gttctgagct ggcgtctgag ctgctgcggg gtggaagtgg    2940
ggggctgccc actccactcc tcccatcccc tcccagcctc ctcctccggc aggaactgaa    3000
cagaaccaca aaaagtctac atttatttaa tatgatggtc tttgcaaaaa ggaacaaaac    3060
aacacaaaag cccaccaggc tgctgctttg tggaaagacg gtgtgtgtcg tgtgaaggcg    3120
aaacccggtg tacataaccc ctcccccctcc gccccgcccc gcccggcccc gtagagtccc    3180
tgtcgcccgc cggccctgcc tgtagatacg ccccgctgtc tgtgctgtga gagtcgccgc    3240
tcgctggggg ggaagggggg gacacagcta cacgcccatt aaagcacagc acgtcctggg    3300
ggagggggcc attttttatg ttacaaaaaa aaattacgaa agaaaagaaa tctctatgca    3360
aaatgacgaa catggtcctg tggactcctc tggcctgttt tgttggctct ttctctgtaa    3420
ttccgtgttt tcgcttttttc ctccctgccc ctctctccct ctgcccctct ctcctctccg    3480
cttctctccc cctctgtctc tgtctctctc cgtctctgtc gctcttgtct gtctgtctct    3540
gctctttcct cggcctctct ccccagacct ggcccggccg ccctgtctcc gcaggctaga    3600
tccgaggtgg cagctccagc cccgggctc gcccctcgc gggcgtgccc cgcgcgcccc    3660
gggcggccga aggccgggcc gccccgtccc gccccgtagt tgctcttttcg gtagtggcga    3720
tgcgccctgc atgtctcctc acccgtggat cgtgacgact cgaaataaca gaaacaaagt    3780
caataaagtg aaaataaata aaaatccttg aacaaatccg aaaaggcttg gagtcctcgc    3840
ccagatctct ctcccctgcg agccctttttt atttgagaag gaaaaagaga aagagaatc    3900
gtttaaggga acccggcgcc cagccaggct ccagtggccc gaacggggcg gcgagggcgg    3960
cgagggcgcc gaggtccggc ccatcccagt cctgtggggc tggccgggca gagacccccgg    4020
acccaggccc aggcctaacc tgctaaatgt ccccggacgg ttctggtctc ctcggccact    4080
ttcagtgcgt cggttcgttt tgattctttt tcttttgtgc acataagaaa taaataataa    4140
taataaataa agaataaaat tttgtatgtc aaaaaaaaaa aaaaaaaa                4188
```

<210> SEQ ID NO 68
<211> LENGTH: 431
<212> TYPE: PRT
<213> ORGANISM: Homo sapiens

<400> SEQUENCE: 68

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80
```

```
Gly Val Ile Gly Gly Ser Lys Pro Lys Val Ala Thr Pro Lys Val Val
                    85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Val Glu Val
        195                 200                 205

Tyr Thr Asp Pro Ala His Ile Arg Gly Gly Gly Leu His Leu Val
    210                 215                 220

Trp Thr Leu Arg Asp Val Ser Glu Gly Ser Val Pro Asn Gly Asp Ser
225                 230                 235                 240

Gln Ser Gly Val Asp Ser Leu Arg Lys His Leu Arg Ala Asp Thr Phe
                245                 250                 255

Thr Gln Gln Gln Leu Glu Ala Leu Asp Arg Val Phe Glu Arg Pro Ser
            260                 265                 270

Tyr Pro Asp Val Phe Gln Ala Ser Glu His Ile Lys Ser Glu Gln Gly
        275                 280                 285

Asn Glu Tyr Ser Leu Pro Ala Leu Thr Pro Gly Leu Asp Glu Val Lys
    290                 295                 300

Ser Ser Leu Ser Ala Ser Thr Asn Pro Glu Leu Gly Ser Asn Val Ser
305                 310                 315                 320

Gly Thr Gln Thr Tyr Pro Val Val Thr Gly Arg Asp Met Ala Ser Thr
                325                 330                 335

Thr Leu Pro Gly Tyr Pro Pro His Val Pro Pro Thr Gly Gln Gly Ser
            340                 345                 350

Tyr Pro Thr Ser Thr Leu Ala Gly Met Val Pro Gly Ser Glu Phe Ser
        355                 360                 365

Gly Asn Pro Tyr Ser His Pro Gln Tyr Thr Ala Tyr Asn Glu Ala Trp
    370                 375                 380

Arg Phe Ser Asn Pro Ala Leu Leu Met Pro Pro Pro Gly Pro Pro Leu
385                 390                 395                 400

Pro Leu Leu Pro Leu Pro Met Thr Ala Thr Ser Tyr Arg Gly Asp His
                405                 410                 415

Ile Lys Leu Gln Ala Asp Ser Phe Gly Leu His Ile Val Pro Val
            420                 425                 430

<210> SEQ ID NO 69
<211> LENGTH: 4257
<212> TYPE: DNA
<213> ORGANISM: Homo sapiens

<400> SEQUENCE: 69
aggctccagt ctccggccga gtcttctcgc agccgcaacc cacctggggc cagcccagag      60
ctgccagcgc cgctcggctc cctccctccc tccggccct tcggccgcgg cggcgtcgc       120 ctgccttttc cggggcggg ggcctggccc gcgcgctccc ctcccgcagg cgccaccctcg    180
```

| | |
|---|---|
| gacatccccg ggattgctac ttctctgcca acttcgccaa ctcgccagca cttggagagg | 240 |
| cccggctccc ctcccggcgc cctctgaccg ccccgcccc gcgcgctctc cgaccaccgc | 300 |
| ctctcggatg accaggttcc aggggagctg agcgagtcgc ctcccccgcc cagcttcagc | 360 |
| cctggctgca gctgcagcgc gagccatgcg ccccagtgc accccggccc ggccaccgc | 420 |
| cccggggcca ttctgctgac cgcccagccc cgagcccga cagtggcaag ttgcggctac | 480 |
| tgcagttgca agctccggcc aacccggagg agccccagcg gggagcgcag tgttgcgccc | 540 |
| cccgccccg cgcgccccgc agcagccggg cgttcactca tcctccctcc cccaccgtcc | 600 |
| ctcccttttc tcctcaagtc ctgaagttga gtttgagagg cgacacgcg gcggcggccg | 660 |
| cgctgctccc gctcctctgc ctccccatgg atatgcactg caaagcagac cccttctccg | 720 |
| cgatgcaccc agggcacggg ggtgtgaacc agctcggggg ggtgtttgtg aacgccggc | 780 |
| ccctacccga cgtggtgagg cagcgcatcg tggagctggc ccaccagggt gtgcggccct | 840 |
| gtgacatctc ccggcagctg cgggtcagcc acggctgtgt cagcaaaatc ctgggcaggt | 900 |
| actacgagac cggcagcatc aagccgggtg tgatcggtgg ctccaagccc aaagtggcga | 960 |
| cgcccaaagt ggtggacaag attgctgaat acaaacgaca gaacccgact atgttcgcct | 1020 |
| gggagattcg agaccggctc ctggccgagg gcatctgtga caatgacaca gtgcccagcg | 1080 |
| tctcttccat caacagaatc atccggacca aagttcagca gcctttccac ccaacgccgg | 1140 |
| atggggctgg gacaggagtg accgcccctg gccacaccat tgttcccagc acggcctccc | 1200 |
| ctcctgtttc cagcgcctcc aatgaccag tgggatccta ctccatcaat gggatcctgg | 1260 |
| ggattcctcg ctccaatggt gagaagagga aacgtgatga agttgaggta tacactgatc | 1320 |
| ctgcccacat tagaggaggt ggaggttttgc atctggtctg gactttaaga gatgtgtctg | 1380 |
| agggctcagt ccccaatgga gattcccaga gtggtgtgga cagtttgcgg aagcacttgc | 1440 |
| gagctgacac cttcacccag cagcagctgg aagctttgga tcgggtcttt gagcgtcctt | 1500 |
| cctaccctga cgtcttccag gcatcagagc acatcaaatc agaacagggg aacgagtact | 1560 |
| ccctcccagc cctgaccct gggcttgatg aagtcaagtc gagtctatct gcatccacca | 1620 |
| accctgagct gggcagcaac gtgtcaggca cacagacata cccagttgtg actggtcgtg | 1680 |
| acatggcgag caccactctg cctggttacc ccctcacgt gccccccact ggccagggaa | 1740 |
| gctaccccac ctccacccctg gcaggaatgg tgcctgggag cgagttctcc ggcaacccgt | 1800 |
| acagccaccc ccagtacacg gcctacaacg aggcttggag attcagcaac cccgccttac | 1860 |
| taatgccgcc ccccggtccg cccctgccgc tgctgccgct gcctatgacc gccactagtt | 1920 |
| accgcgggga ccacatcaag cttcaggccg acagcttcgg cctccacatc gtccccgtct | 1980 |
| gaccccaccc cggagggagg gaggaccgac gcgacgcgat gcctcccggc caccgcccca | 2040 |
| gcctcacccc atcccacgac ccccgcaacc cttcacatca ccccctcga aggtcggaca | 2100 |
| ggacgggtgg agccgtgggc gggaccctca ggcccgggcc cgccgccccc agcccgcct | 2160 |
| gccgcccctc cccgcctgcc tggactgcgc ggcgccgtga gggggattcg gcccagctcg | 2220 |
| tcccggcctc caccaagcca gccccgaagc ccgccagcca cctgccgga ctcgggcgcg | 2280 |
| acctgctggc gcgcgccgga tgtttctgtg acacacaatc agcgcggacc gcagcgcggc | 2340 |
| ccagcccgg gcaccgcct cggacgctcg ggcgccagga ggcttcgctg gaggggctgg | 2400 |
| gccaaggaga ttaagaagaa aacgactttc tgcaggagga agagcccgct gccgaatccc | 2460 |
| tgggaaaaat tctttcccc cagtgccagc cggactgccc tcgccttccg ggtgtgccct | 2520 |
| gtcccagaag atggaatggg ggtgtggggg tccggctcta ggaacgggct ttggggggcgt | 2580 |

```
caggtctttc caaggttggg acccaaggat cgggggccc agcagcccgc accgatcgag      2640
ccggactctc ggctcttcac tgctcctcct ggcctgccta gttccccagg gcccggcacc      2700
tcctgctgcg agaccggct ctcagccctg ccttgcccct acctcagcgt ctcttccacc       2760
tgctggcctc ccagtttccc ctcctgccag tccttcgcct gtcccttgac gccctgcatc      2820
ctcctccctg actcgcagcc ccatcggacg ctctcccggg accgccgcag gaccagtttc      2880
catagactgc ggactggggt cttcctccag cagttacttg atgcccctc ccccgacaca       2940 gactctcaat ctgccggtgg taagaaccgg ttctgagctg gcgtctgagc tgctgcgggg      3000
tggaagtggg gggctgccca ctccactcct cccatccct cccagcctcc tcctccggca       3060
ggaactgaac agaaccacaa aaagtctaca tttatttaat atgatggtct ttgcaaaaag      3120
gaacaaaaca acacaaaagc ccaccaggct gctgctttgt ggaaagacgg tgtgtgtcgt      3180
gtgaaggcga aacccggtgt acataacccc tcccctccg ccccgccccg cccggccccg       3240
tagagtccct gtcgcccgcc ggccctgcct gtagatacgc cccgctgtct gtgctgtgag      3300
agtcgccgct cgctgggggg gaagggggg acacagctac acgcccatta aagcacagca      3360
cgtcctgggg gagggggca ttttttatgt tacaaaaaaa aattacgaaa gaaaagaaat       3420
ctctatgcaa aatgacgaac atggtcctgt ggactcctct ggcctgtttt gttggctctt      3480
tctctgtaat tccgtgtttt cgcttttttcc tccctgcccc tctctccctc tgcccctctc     3540
tcctctccgc ttctctcccc ctctgtctct gtctctctcc gtctctgtcg ctcttgtctg      3600
tctgtctctg ctcttccctc ggcctctctc cccagcctg gcccggccgc cctgtctccg       3660
caggctagat ccgaggtggc agctccagcc cccgggctcg ccccctcgcg ggcgtgcccc      3720
gcgcgccccg ggcggccgaa ggccgggccg cccgtcccg ccccgtagtt gctcttccgg      3780
tagtggcgat gcgccctgca tgtctcctca cccgtggatc gtgacgactc gaaataacag      3840
aaacaaagtc aataaagtga aaataaataa aaatccttga acaaatccga aaaggcttgg      3900
agtcctcgcc cagatctctc tcccctgcga gccctttta tttgagaagg aaaaagagaa       3960
aagagaatcg tttaagggaa cccgcgcgcc agccaggctc cagtggcccg aacggggcgg      4020
cgagggcggc gagggcgccg aggtccggcc catcccagtc ctgtggggct ggccgggcag      4080
agaccccgga cccaggccca ggcctaacct gctaaatgtc cccggacggt tctggtctcc      4140
tcggccactt tcagtgcgtc ggttcgtttt gattctttt cttttgtgca cataagaaat       4200
aaataataat aataaataaa gaataaaatt ttgtatgtca aaaaaaaaa aaaaaa         4257

<210> SEQ ID NO 70
<211> LENGTH: 104
<212> TYPE: DNA
<213> ORGANISM: Homo sapiens

<400> SEQUENCE: 70
ttcacccttg actgtggcac ctcccttcag ttccgtcgac gaggttgtgc aatccaccag      60
tcttataaat acagtgacgc tccagcctct ggaagcctct gtca                      104

<210> SEQ ID NO 71
<211> LENGTH: 17
<212> TYPE: DNA
<213> ORGANISM: Homo sapiens

<400> SEQUENCE: 71
tcaagcgtga ctaattg                                                    17
```

DETECTING PAX2 FOR THE DIAGNOSIS OF BREAST CANCER

This application is a continuation of U.S. patent application Ser. No. 12/546,292, filed Aug. 24, 2009, which is a continuation-in-part of the U.S. patent application Ser. No. 12/440,193, filed Mar. 13, 2009, now U.S. Pat. No. 8,088,603, as a national stage application of PCT/US2008/051168, filed Jan. 16, 2008, which claims priority of U.S. Provisional Application No. 60/885,142, filed Jan. 16, 2007. The entirety of all of the aforementioned application is incorporated herein by reference.

FIELD

The present application generally relates to medical diagnosis and, in particular, to methods for diagnosing cancerous conditions in various tissues.

BACKGROUND

Breast cancer is the most common cause of cancer in women and the second most common cause of cancer death in women in the U.S. While the majority of new breast cancers are diagnosed as a result of an abnormality seen on a mammogram, a lump or change in consistency of the breast tissue can also be a warning sign of the disease. Heightened awareness of breast cancer risk in the past decades has led to an increase in the number of women undergoing mammography for screening, leading to detection of cancers in earlier stages and a resultant improvement in survival rates. Still, breast cancer is the most common cause of death in women between the ages of 45 and 55.

Breast cancer may be classified into several stages. Stage 0 is carcinoma (including lobular carcinoma and ductal carcinoma) in situ. Stage I is an early stage of invasive breast cancer. The tumor is no more than 2 centimeters across. Cancer cells have not spread beyond the breast. Stage II tumors include tumors that are no more than 2 centimeters across but has spread to the lymph nodes under the arm, tumors that are between 2 and 5 centimeters and may have spread to the lymph nodes under the arm, and tumors that are larger than 5 centimeters (2 inches) but has not spread to the lymph nodes under the arm. Stage III is locally advanced cancer. It is further divided into Stage IIIA, IIIB, and IIIC. Stage IV is distant metastatic cancer. The cancer has spread to other parts of the body. Early-stage treatment options are different from late-stage options.

It is known that many types of cancer are caused by genetic aberrations, i.e., mutations. The accumulation of mutations and the loss of cellular control functions cause progressive phenotypic changes from normal histology to early pre-cancer such as intraepithelial neoplasia (IEN) to increasingly severe IEN to superficial cancer and finally to invasive disease. Although this process can be relatively aggressive in some cases, it generally occurs relatively slowly over years and even decades. Oncogene addiction is the physiologic dependence of cancer cells on the continued activation or over expression of single oncogenes for maintaining the malignant phenotype. This dependence occurs in the milieu of the other changes that mark neoplastic progression.

The long period of progression to invasive cancer provides an opportunity for clinical intervention. Therefore, it is important to identify biomarkers that are indicative of pre-cancerous conditions so that treatment measures can be taken to prevent or delay the development of invasive cancer.

SUMMARY

One aspect of the present invention relates to a method for monitoring breast conditions in a subject. The method comprises determining a Paired Box 2 gene-to-beta defensin-1 gene (PAX2-to-DEFB1) expression ratio in cells obtained from the breast of the subject, wherein the PAX2-to-DEFB1 expression ratio is correlated with breast conditions and may serve as a prognosticator used for determining course of treatment.

In one embodiment, a PAX2-to-DEFB1 expression ratio of 100:1 or higher is indicative of the presence of breast cancer in the subject, and a PAX2-to-DEFB1 expression ratio less than 100:1 is indicative of the presence of non-cancerous or pre-cancerous breast condition in the subject.

In another embodiment, the determining step comprises determining the expression level of PAX2 gene relative to the expression level of a control gene, determining the expression level of DEFB1 gene relative to the expression level of the same control gene; and determining the PAX2-to-DEFB1 expression ratio based on the expression levels of PAX2 and DEFB1.

In one embodiment, the method further comprising determining an oestrogen receptor/progesterone receptor/human epidermal growth factor receptor 2 (ER/PR/HER2) status in cells obtained from the breast tissue with the breast condition.

Another aspect of the present invention relates to a kit for monitoring breast conditions. In one embodiment, the kit for monitoring breast conditions comprises: one or more pairs of oligonucleotide primers for detecting PAX2 expression in a tissue sample, one or more pairs of oligonucleotide primers for detecting DEFB1 expression in the tissue sample, and instructions on how to determine the PAX2-to-DEFB1 expression ratio in a tissue sample using the primers. In another embodiment, the one or more pairs of oligonucleotide primers for detecting PAX2 expression comprising an oligonucleotide primer pair selected from the group consisting of SEQ ID NOS: 43 and 47, SEQ ID NOS: 44 and 48, and SEQ ID NOS: 45 and 49. In another embodiment, the one or more pairs of oligonucleotide primers for detecting DEFB1 expression comprising SEQ ID NOS: 35 and 37.

In another embodiment, the kit further comprises one or more pairs of control oligonucleotide primers. In one embodiment, the one or more pairs of control oligonucleotide primers comprise oligonucleotide primers for detecting expression of β-actin expression. In a preferred embodiment, the oligonucleotide primers for detecting expression of β-actin expression comprise SEQ ID NOS: 34 and 36.

In another embodiment, the one or more pairs of control oligonucleotide primers comprise oligonucleotide primers for detecting expression of GAPDH expression. In a preferred embodiment, the oligonucleotide primers for detecting expression of GAPDH expression comprise SEQ ID NOS: 42 and 46.

In another related embodiment, the kit further comprises one or more reagents for PCR reaction.

In yet another related embodiment, the kit further comprises one or more reagents for RNA extraction.

In another embodiment, the kit for monitoring breast conditions comprises an oligonucleotide microarray having oligonucleotide probes for detecting PAX2 and DEFB1 expression and instructions on how to determine the PAX2-to-DEFB1 expression ratio in a tissue sample using the oligonucleotide microarray.

In a related embodiment, the kit further comprises reagents for extracting RNA from a tissue sample.

Another aspect of the invention relates to a method for determining a treatment regimen for a subject with a breast condition. The method includes the step of determining the expression level of PAX2 gene relative to the expression level of a control gene in cells obtained from a breast tissue with the breast condition in said subject, and determining a treatment regimen for said subject based on the relative expression level of the PAX2 gene.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A shows DEFB1 relative expression levels compared in clinical samples from 6 patients that underwent radical prostatectomies. FIG. 1B shows DEFB1 relative expression levels compared in benign and malignant prostatic clinical samples, hPrEC cells and in prostate cancer cell lines before and after DEFB1 induction. FIG. 1C shows DEFB1 relative expression levels analyzed in benign tissue, malignant tissue and prostate intraepithelial neoplasia (PIN) in a single tissue section. FIG. 1D shows DEFB1 expression in benign tissue, malignant tissue and PIN in one patient compared to the average DEFB1 expression level found in benign tissue.

FIG. 10A shows Bcl-2-associated X protein (BAX) expression levels increased in DU145, PC3 and LNCaP. FIG. 10B shows BH3 interacting domain death agonist (BID) expression increased in DU145 and LNCaP, but change in PC3. FIG. 10C shows Bcl-2-associated death promoter (BAD) expression levels increased in all three cell lines.

Figure 15A:
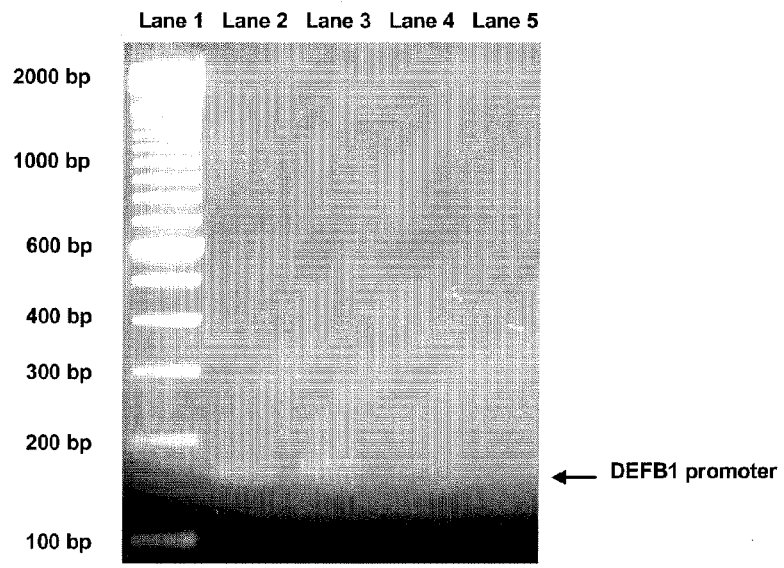
Figure 15B:
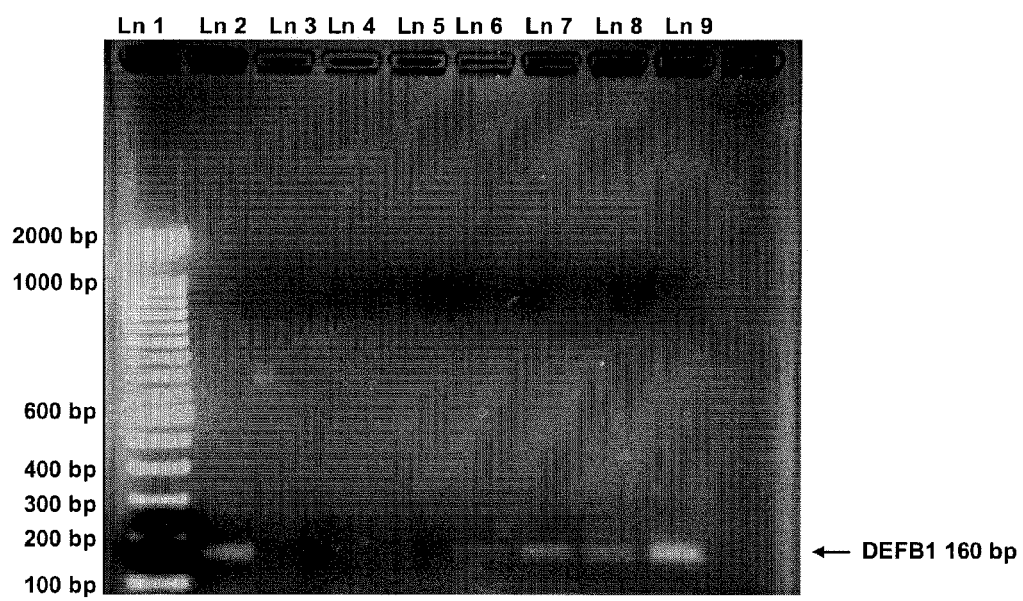

FIGS. 15A and 15B show ChIP analysis of PAX2 binding to DEFB1 promoter. ChIP analysis was performed on DU145 and PC3 cells. Following immunoprecipitation with an anti-PAX2 antibody, PCR was performed to detect the DEFB1 promoter region containing the GTTCC (SEQ ID NO: 2) PAX2 recognition site. This demonstrates that the PAX2 transcriptional repressor is bound to the DEFB1 promoter in prostate cancer cell lines.

Figure 16:
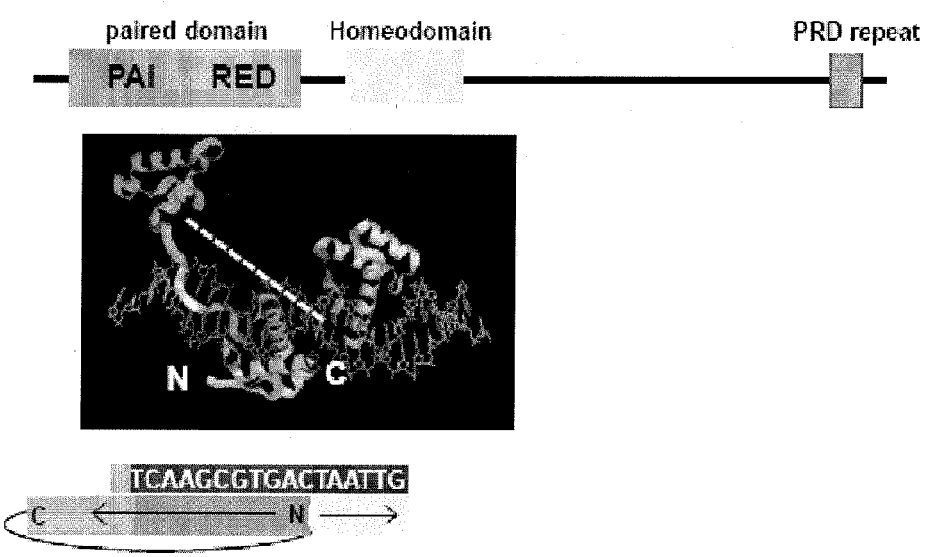

FIG. 16 shows predicted structure of the PrdPD and PrdHD with DNA. The coordinates of the structures of the PrdPD bound to DNA (Xu et al., 1995) and the PrdHD bound to DNA (Wilson et al., 1995) were used to construct a model of the two domains as they bound to a PH0 site. The individual binding sites are abutted next to each other with a specific orientation as indicated. The RED domain is oriented based on the PrdPD crystal structure.

Figure 17:
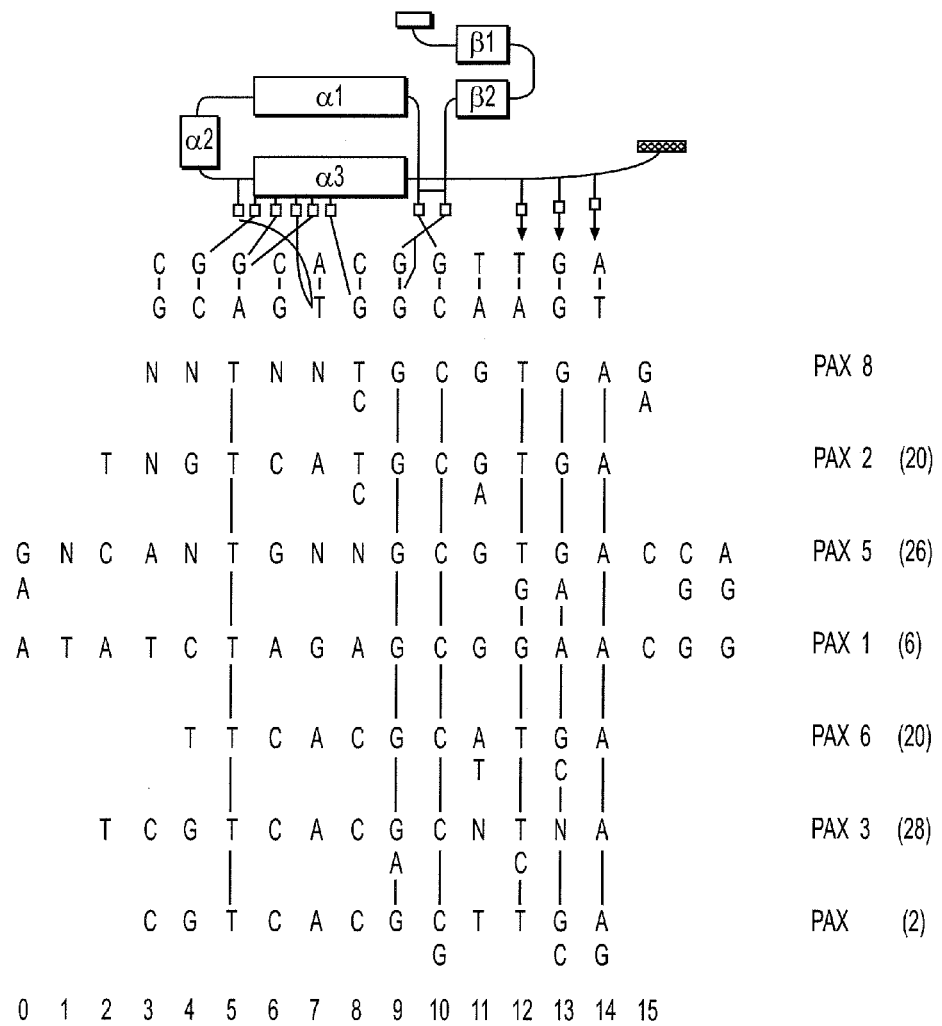

FIG. 17 shows comparison of consensus sequences of different paired domains. At the top of the Figure is drawn a schematic representation of protein±DNA contacts described in the crystallographic analysis of the Prd-paired-domain±DNA complex. Empty boxes indicate a-helices, shaded boxes indicates b-sheets and a thick line indicate a b-turn. Contacting amino acids are shown by single-letter code. Only direct amino acid±base contacts are shown. Empty circles indicate major groove contacts while red arrows indicate minor groove contacts. This scheme is aligned to all known consensus sequences for paired-domain proteins (top strands only are shown). Vertical lines between consensus sequences indicate conserved base-pairs. Numbering of the positions is shown at the bottom of the Figure.

Figure 18:
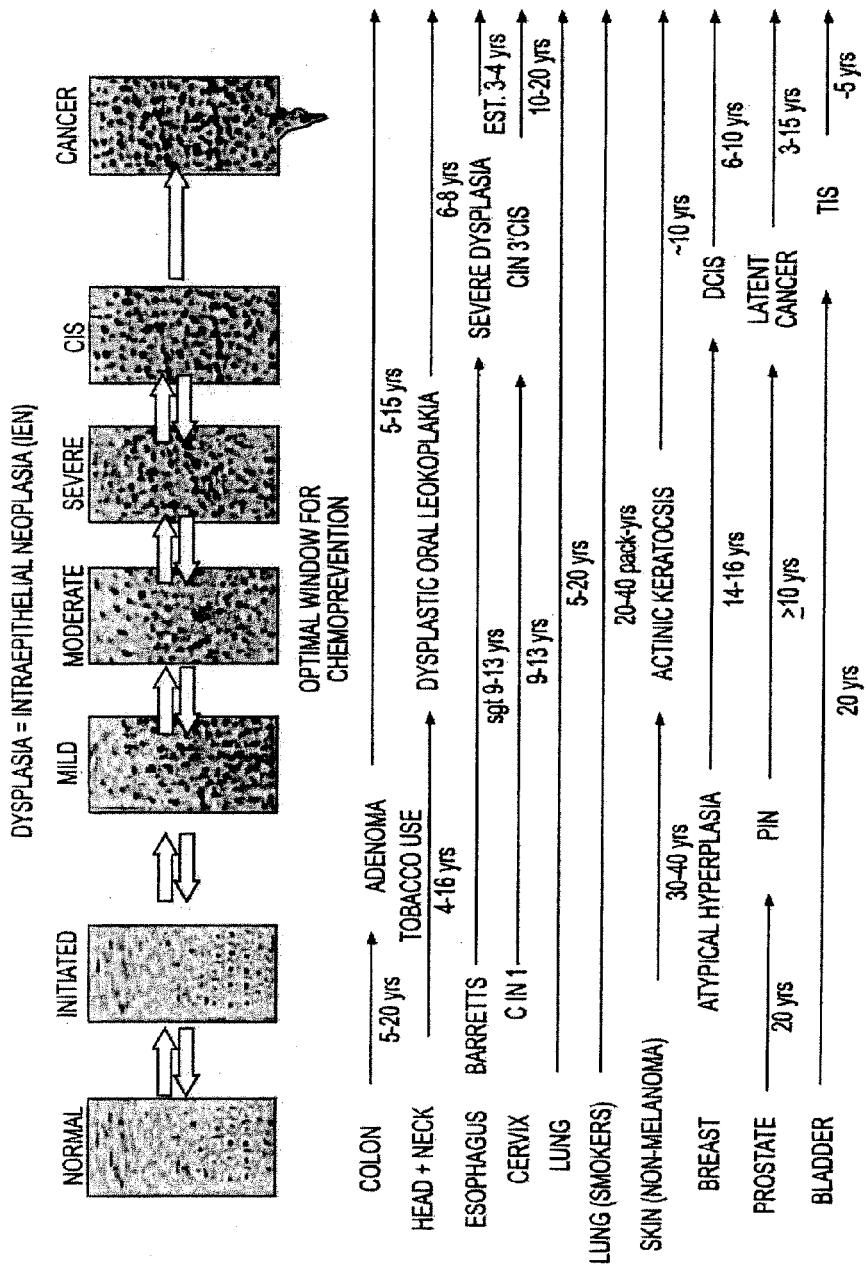

FIG. 18 shows targeting PAX2 as a chemopreventive strategy. Aberrant PAX2 expression is an early event in the initiation and progression of cancer. Inhibition of PAX2 during dysplasia or other precancerous stage can be used for cancer prevention.

Figure 19:
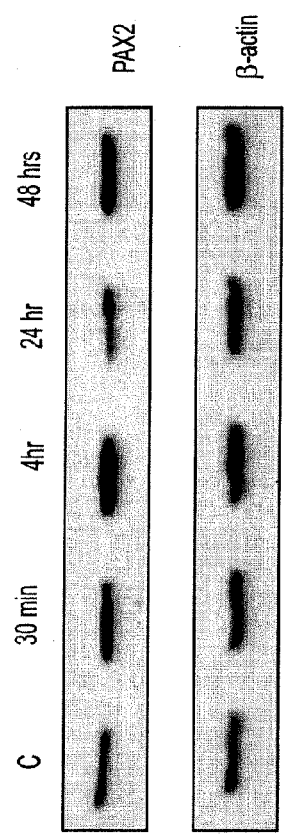

FIG. 19 shows effect of angiotensin II (Ang II) on PAX2 expression in DU145 Cells. In order to determine the effect of AngII on PAX2 expression, DEFB1 protein levels was monitored following treatment. Here PAX2 expression levels increased as early as 4 hours and persisted until 48 hours.

Figure 20A:
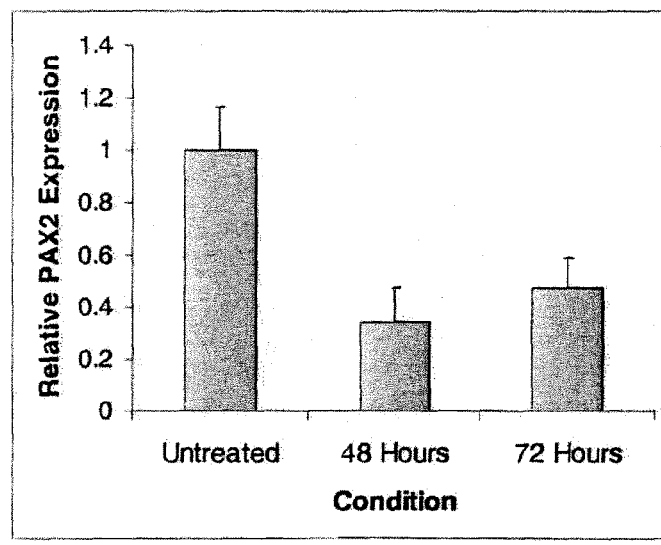
Figure 20B:
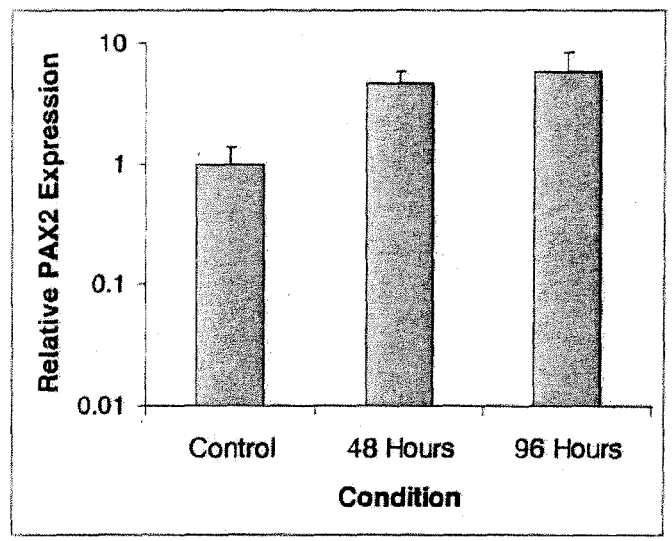

FIG. 20A shows effect of Losartan (Los) on PAX2 expression in DU145. DU145 cells were treated with the angiotensin II type 1 receptor (ATR1) blocker Losartan. QRT-PCR revealed that PAX2 message levels were decreased by at least half following treatment. FIG. 20B shows effect of an angiotensin II type 2 receptor (ATR2) blocker on PAX2 Expression in DU145. To determine the effect of the ATR2 receptor on PAX2 expression, DU145 cells were treated with the ATR2 receptor blocker PD123319. Here, PAX2 expression was increased 7 to 8-fold.

Figure 21:
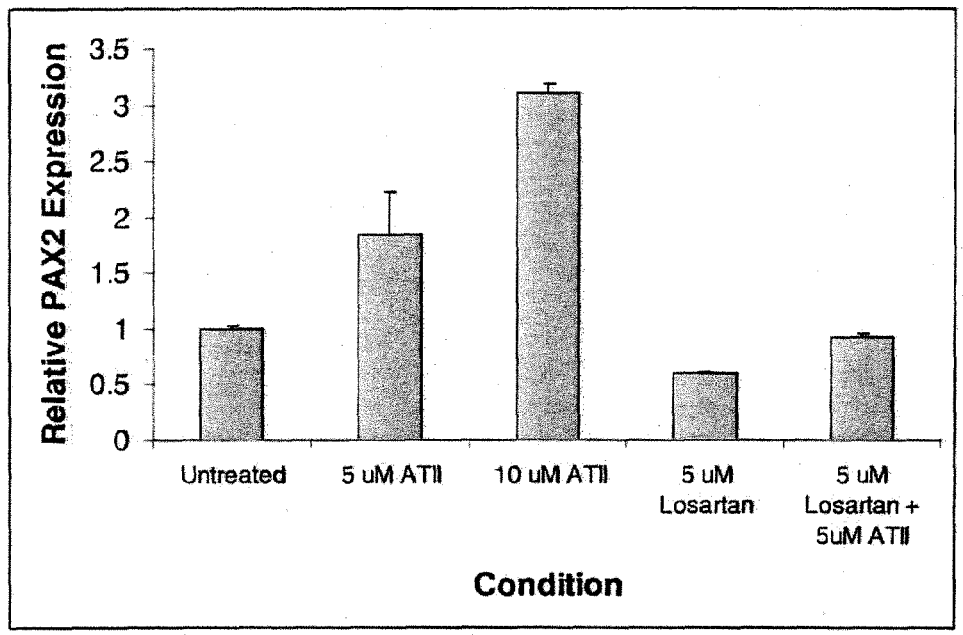

FIG. 21 shows Los blocks AngII effect on PAX2 expression in DU145. Treatment of DU145 cells with 5 µM of AngII for 72 hours resulted in a 2-fold increase in PAX2 expression. In addition, treatment with 10 µM for 72 hours resulted in more than a 3-fold increase in expression. Treatment of cells with 5 µM of Losartan suppressed proliferation by 50%. In addition, treatment with Losartan for 30 min prior to treatment with AngII blocked the effect of AngII on proliferation.

Figure 22:
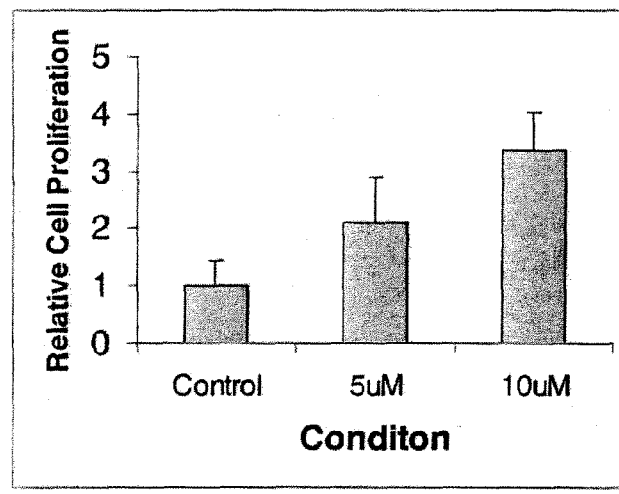

FIG. 22 shows AngII increases DU145 cell proliferation. Treatment of DU145 cells with 5 µM of AngII for 72 hours resulted in a 2-fold increase in proliferation. In addition, treatment with 10 µM for 72 hours resulted in more than a 3-fold increase in proliferation.

Figure 23A:
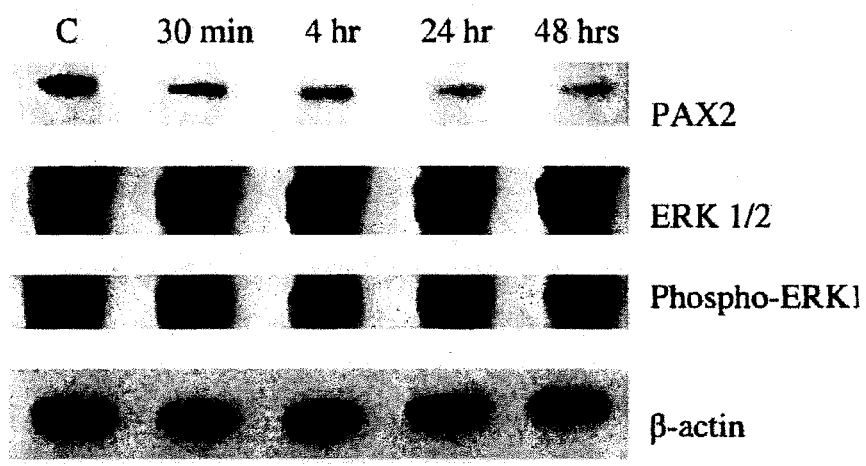
Figure 23B:
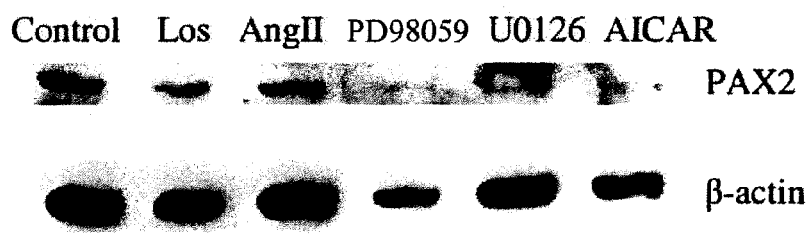
Figure 23C:
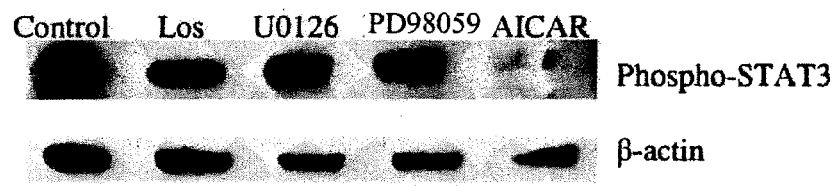

FIGS. 23A-23C show effect of Los and MAP Kinase inhibitors on PAX2 expression in DU145 cells. FIG. 23A shows treatment of DU145 cells with Losartan suppresses phosphor-ERK 1/2 and PAX2 expression; FIG. 23B shows MEK kinase inhibitors and AICAR suppresses PAX2 protein expression; FIG. 23C shows MEK kinase inhibitors and Losartan suppresses phospho-STAT3 protein expression.

Figure 24A:
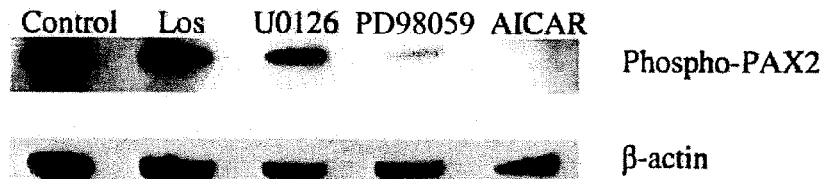
Figure 24B:
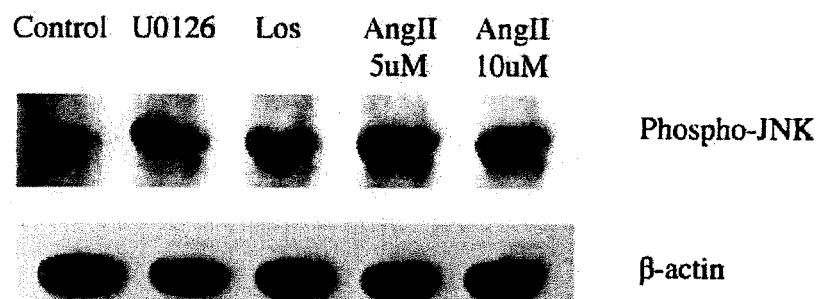

FIGS. 24A and 24B show effect of Los and MEK kinase inhibitors on PAX2 activation in DU145 cells. FIG. 24A shows treatment of DU145 cells with inhibitors of AT1R signaling resulted in a decrease in phosphor-PAX2 protein levels which is the active form of PAX2. In addition, treatment with the AMP kinase inducer AICAR resulted in suppressed PAX2 expression. FIG. 24B shows inhibition of AT1R signaling with Los decreased phopho-JNK levels. However, AngII increased phosphor-JNK protein levels.

Figure 25:
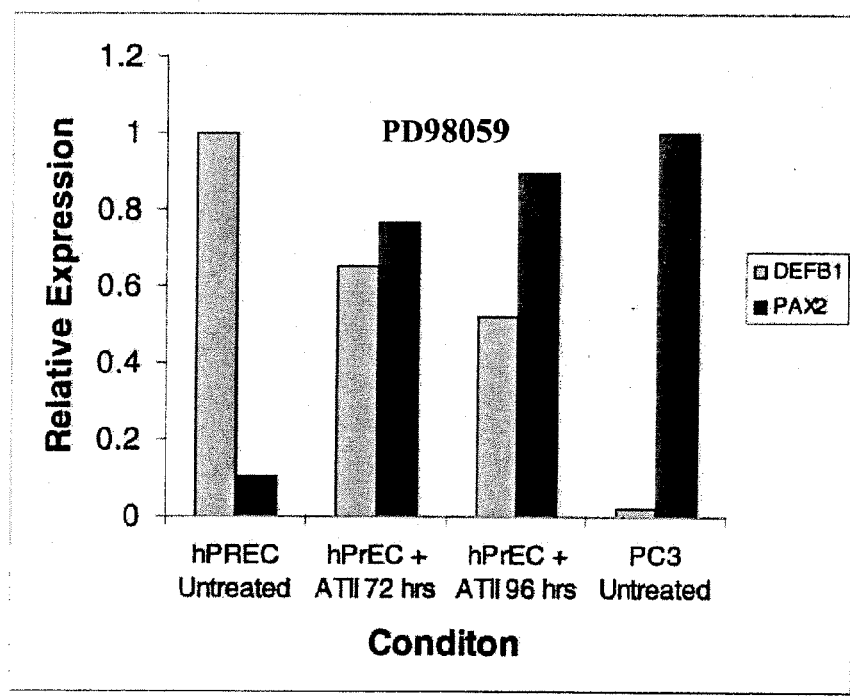

FIG. 25 shows AngII increases PAX2 and decreases DEFB1 expression in hPrEC cells. To determine the effect of AngII on PAX2 levels in hPrEC, cells were treated for 72 and 96 hours and PAX2 and DEFB1 expression was examined by QRT-PCR. Here, AngII treatment resulted in dramatic increases in PAX2 to levels similar to PC3 prostate cancer cells. Conversely, DEFB1 expression was reduced significantly after AngII treatment.

Figure 26:
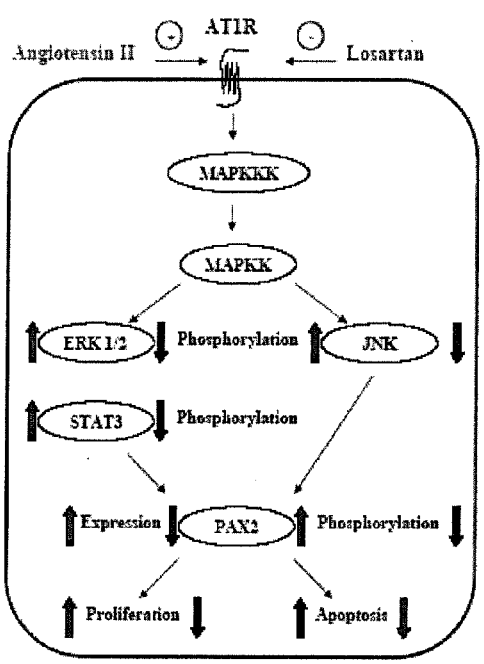

FIG. 26 shows schematic of AngII signaling and PAX2 prostate cancer. PAX2 expression in prostate cancer cells is regulated by the AT1R signaling pathway. Specifically, the MEK kinase signaling cascade leads to increased PAX2 expression. In addition, the AT1R and AngII upregulates PAX2 activation via JNK.

Figure 27:
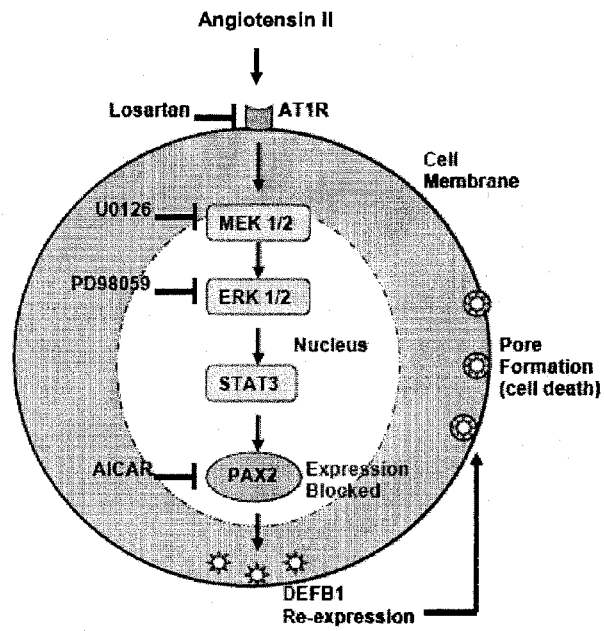

FIG. 27 shows schematic of blocking PAX2 expression as a therapy for prostate cancer. FIG. 27 shows PAX2 expression is regulated by the AT1R signaling pathway. Inhibition of PAX2 expression results in the re-expression of DEFB1 and cancer cell death. FIG. 27 also shows compounds which block the AT1R, downstream kinases or directly suppresses PAX2 offer a novel approach to treating prostate cancer.

Figure 28:
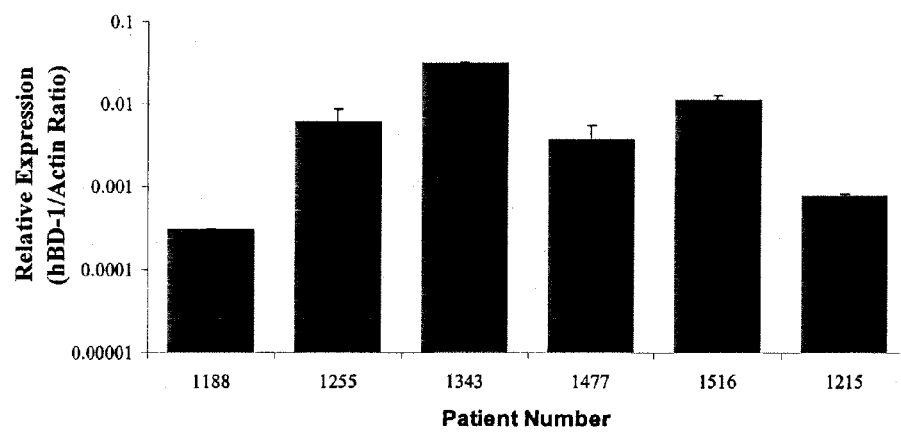

FIG. 28 shows comparison of DEFB1 and PAX2 expression with Gleason Score. DEFB1 relative expression levels were compared in benign clinical samples from 6 patients that underwent radical prostatectomies. Here Gleason score inversely correlated with DEFB1 expression levels in adjacent benign prostate tissue. Patients with relative DEFB1 expression levels higher than 0.005 had Gleason sores of 6. However, those with expression levels less than 0.005 had Gleason scores of 7.

Figure 29A:
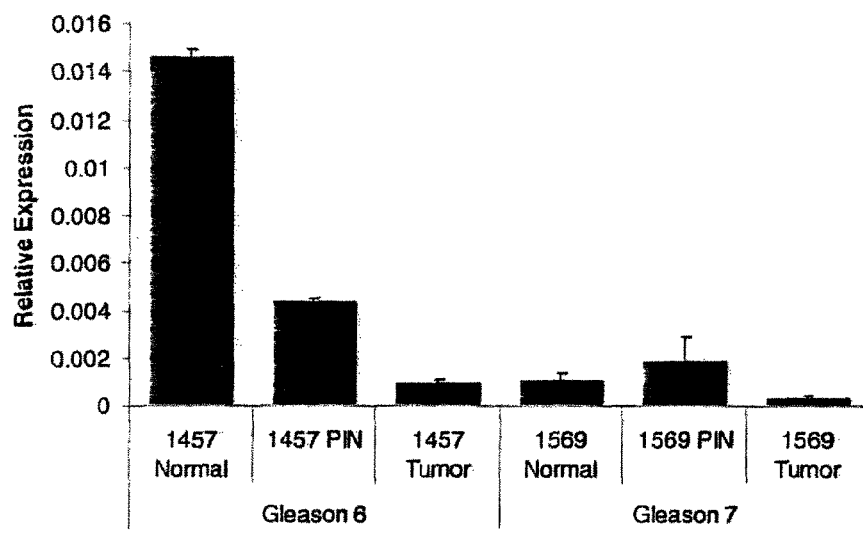
Figure 29B:
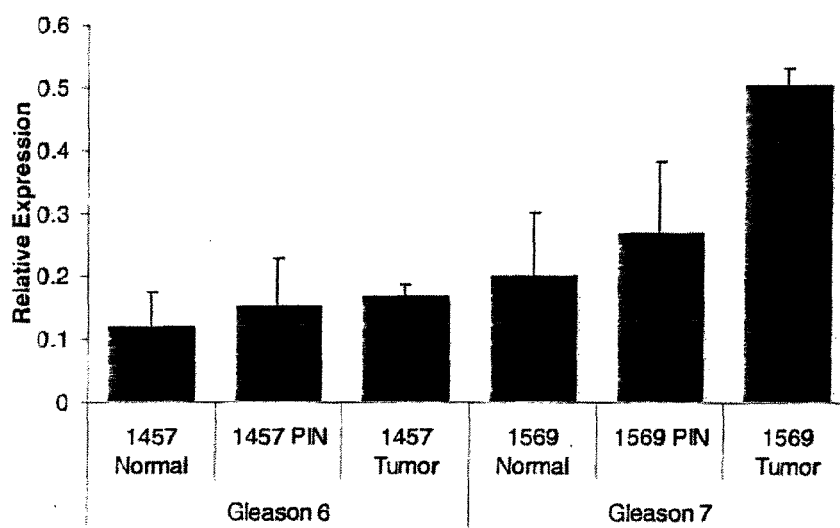

FIGS. 29A and 29B show PAX2-DEFB1 ratio as a predictive factor for prostate cancer development. QRT-PCR was performed on laser capture microdissection (LCM) prostate tissue sections to determine relative DEFB1 (FIG. 29A) and PAX2 (FIG. 29B) expression levels. DEFB1 expression levels decreased from Normal to PIN to cancer. However, PAX2 expression increased from normal to PIN to cancer. In addition, patient #1457 with Gleason score 6 cancer had more DEFB1 in normal tissue and PIN compared to patient #1569 with Gleason score 7 cancer. Conversely, patient #1569 had higher PAX2 levels in cancerous regions compared to patient #1457.

Figure 30:
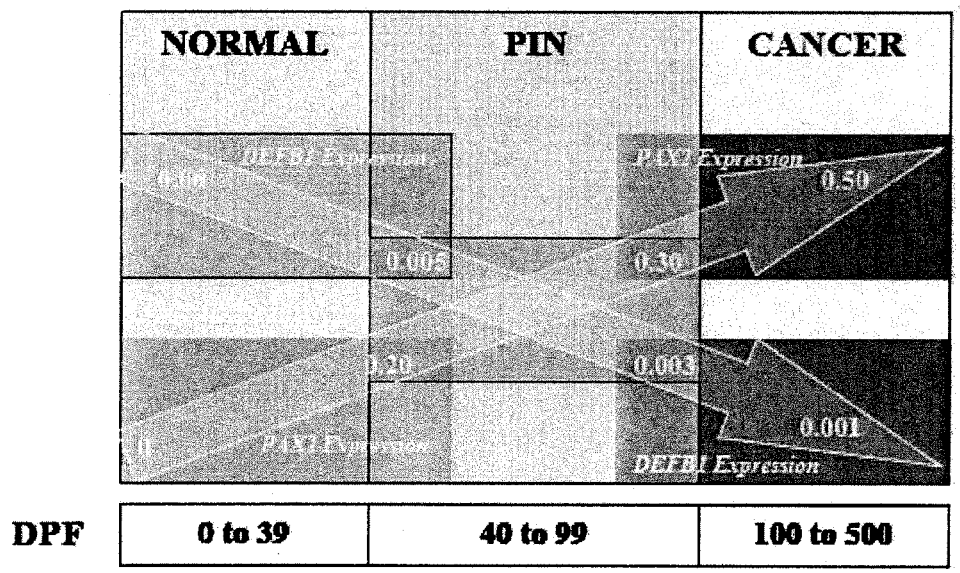

FIG. 30 shows the Donald Predictive Factor (DPF) is based on the relative PAX2-DEFB1 expression ratio. An increase in the DPF of prostate tissue increases the chance of developing prostate cancer. Tissue with a PAX2-DEFB1 ratio between 0 and 39 based on the DPF was normal (benign). Tissue with a PAX2-DEFB1 ratio between 40 and 99 represented PIN (precancerous) based on the DPF scale. Finally, tissue with a PAX2-DEFB1 ratio between 100 and 500 was malignant (low to high grade cancer).

Figure 31A:
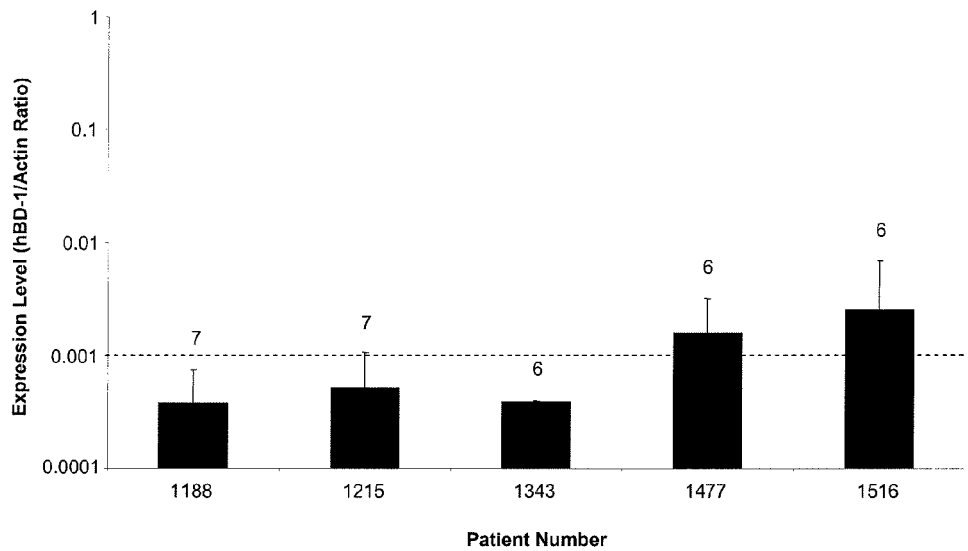
Figure 31B:
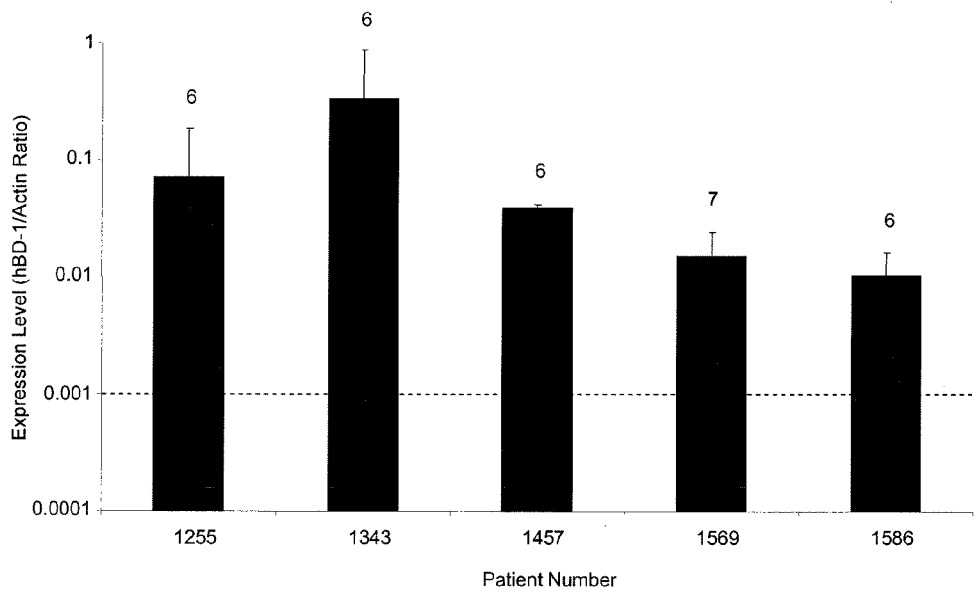

FIGS. 31A and 31B show analysis of hBD-1 expression in human prostate tissue. hBD-1 relative expression levels were compared in normal clinical samples from patients that underwent radical prostatectomies. The dashed line serves as a point of reference to compare values obtained between gross and LCM-derived specimen, and corresponding Gleason scores are indicated above each bar. FIG. 31A shows hBD-1 expression levels compared in tissues obtained by gross dissection. FIG. 31B shows hBD-1 expression levels compared in tissue obtained by Laser Capture Microdissection.

Figure 32A:
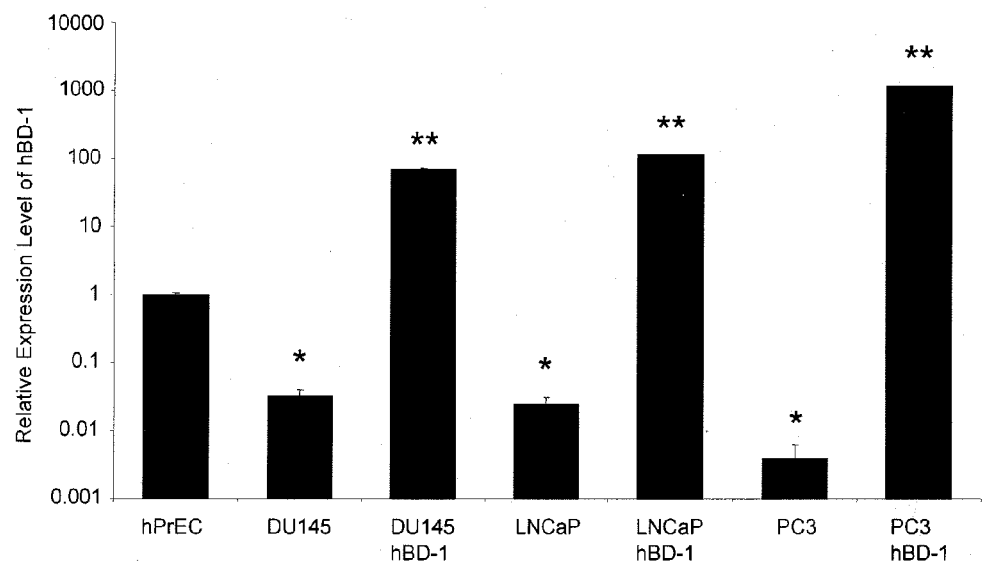
Figure 32B:
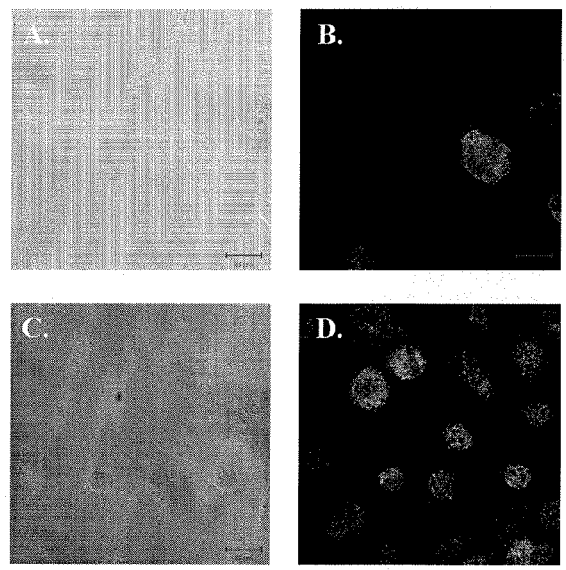

FIGS. 32A and 32B show analysis of hBD-1 expression in prostate cell lines. FIG. 32A shows hBD-1 expression levels compared relative to hPrEC cells in prostate cancer cell lines before and after hBD-1 induction. An asterisk represents statistically higher expression levels compared to hPrEC. Double asterisks represent statistically significant levels of expression compared to the cell line before hBD-1 induction (Student's t-test, p<0.05). FIG. 32B shows ectopic hBD-1 expression verified in the prostate cancer cell line DU145 by immunocytochemistry. hPrEC cells were stained for hBD-1 as appositive control (a: DIC and b: fluorescence). DU145 cells were transfected with hBD-1 and induced for 18 hours (c: DIC and d: fluorescence). Sizebar=20 µM.

Figure 33:
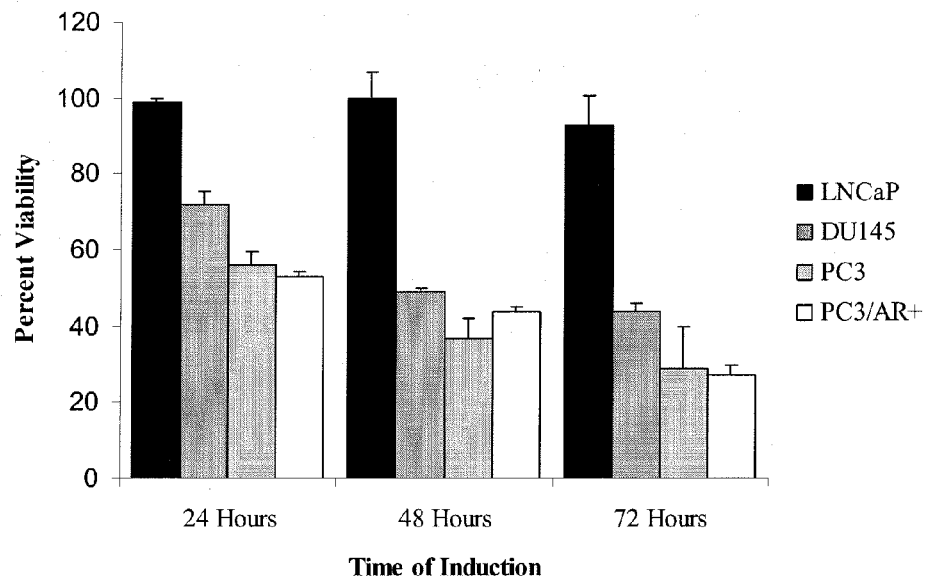

FIG. 33 shows analysis of hBD-1 cytotoxicity in prostate cancer cells. The prostate cell lines DU145, PC3, PC3/AR+ and LNCaP were treated with Pon A to induce hBD-1 expression for 1-3 days after which MTT assay was performed to determine cell viability. Each bar represents the mean±S.E.M. of three independent experiments performed in triplicate.

Figure 34A:
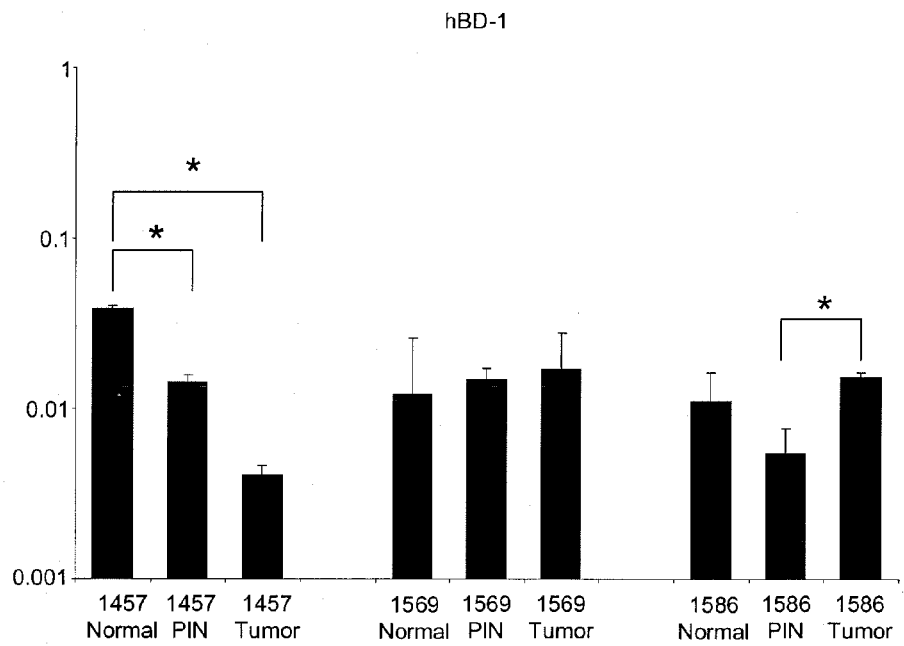
Figure 34B:
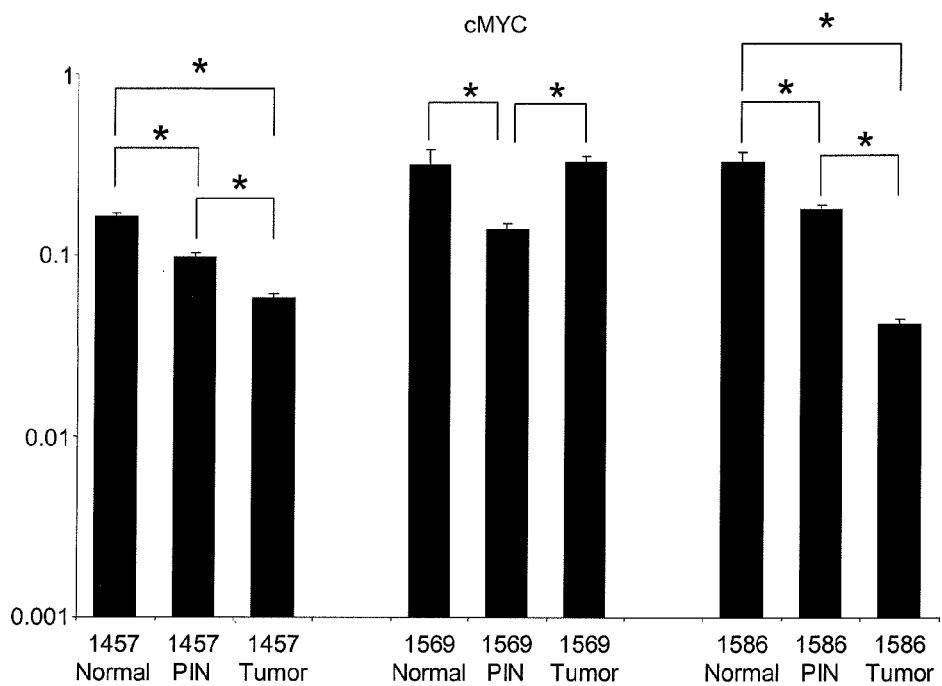

FIGS. 34A and 34B show QRT-PCR analysis of hBD-1 and cMYC expression in LCM human prostate tissue sections of normal, PIN and tumor. Expression for each gene is presented as expression ratios compared to β-actin. FIG. 34A shows comparison of hBD-1 expression levels in normal, PIN and tumor sections. FIG. 34B shows comparison of cMYC expression level in normal, PIN and tumor sections.

Figure 35:
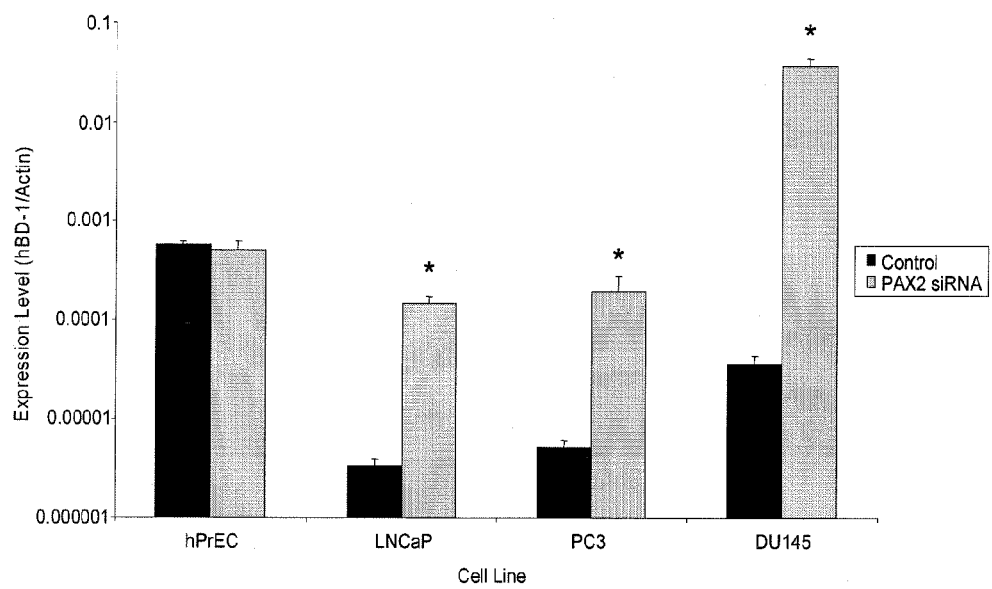

FIG. 35 shows QRT-PCR analysis of hBD1 expression following PAX2 knockdown with siRNA. hBD-1 expression levels are presented as expression ratios compared to β-actin. An asterisk represents statistically higher expression levels compared to the cell line before PAX2 siRNA treatment (Student's t-test, p<0.05).

Figure 36A:
Figure 36B:
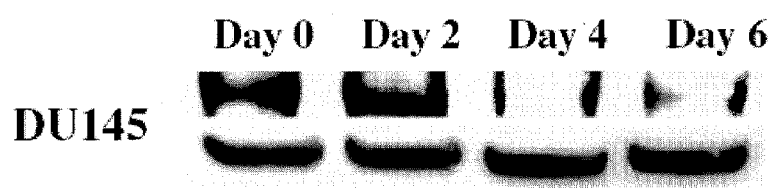
Figure 36B:
Figure 36B:
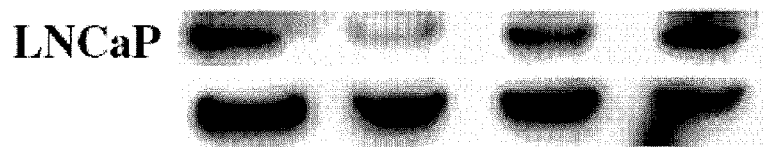

FIGS. 36A and 36B show silencing of PAX2 protein expression following PAX2 siRNA treatment. FIG. 36A shows PAX2 expression examined by Western blot analysis in HPrEC prostate primary cells (lane 1) and in DU145 (lane 2), PC3 (lane 3) and LNCaP (lane 4) prostate cancer cells. Blots were stripped and re-probed for -actin as an internal control to ensure equal loading. FIG. 36B shows Western blot analysis of DU145, PC3 and LNCaP all confirmed knockdown of PAX2 expression following transfection with PAX2 siRNA duplex. Again, blots were stripped and re-probed for β-actin as an internal control.

Figure 37:
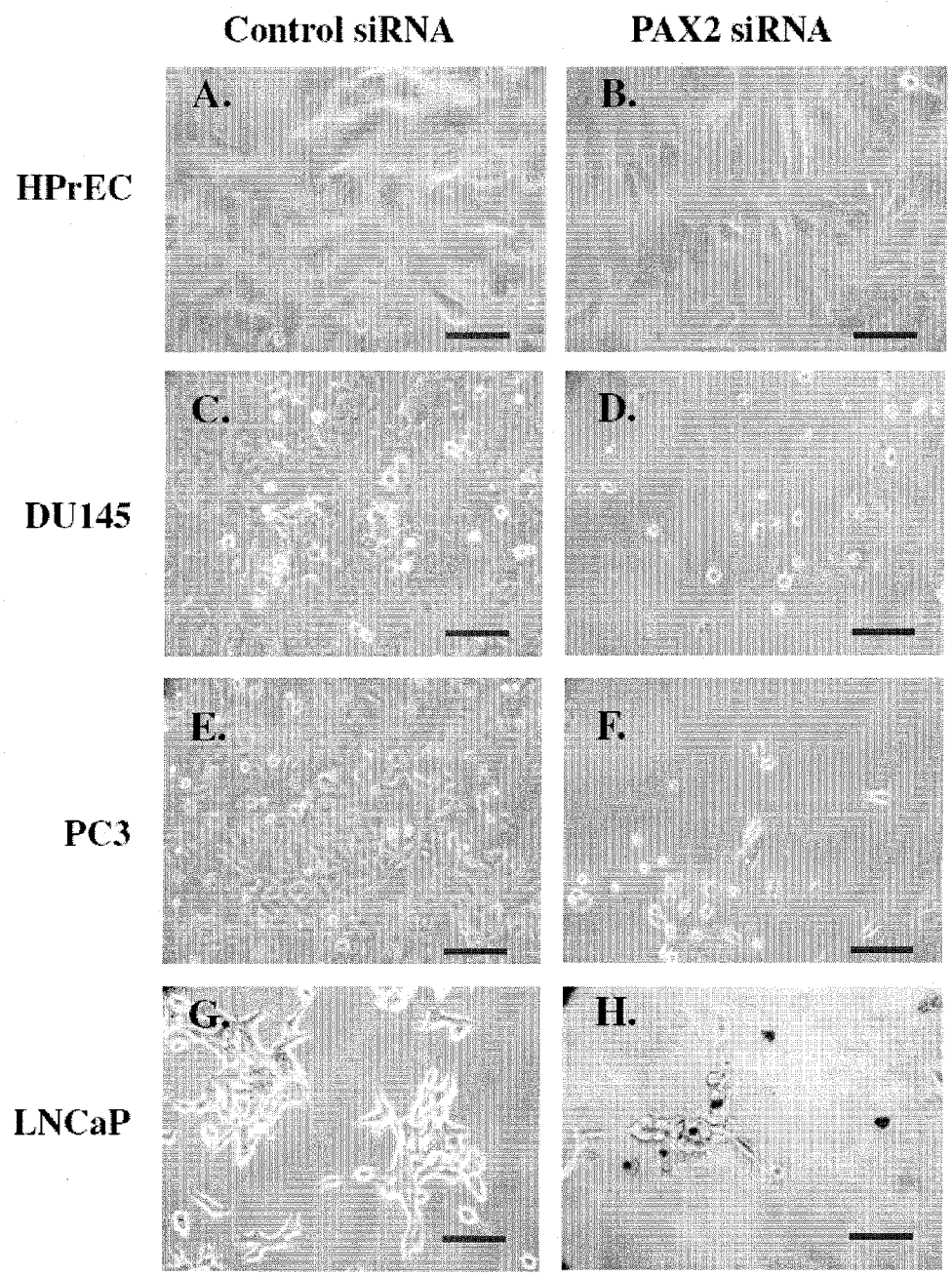

FIG. 37 shows analysis of prostate cancer cells growth after treatment with PAX2 siRNA. Phase contrast microscopic analysis of HPrEC (Panel A), LNCaP (Panel C), DU145 (Panel E) and PC3 (Panel G) at 6 days in the presence of negative control non-specific siRNA. There was a significant reduction in cell number in DU145 (Panel D), PC3 (Panel F) and LNCaP (Panel H) following treatment with PAX2 siRNA. However, there appeared to be no effect in HPrEC (Panel B). Bar=20 µm.

Figure 38:
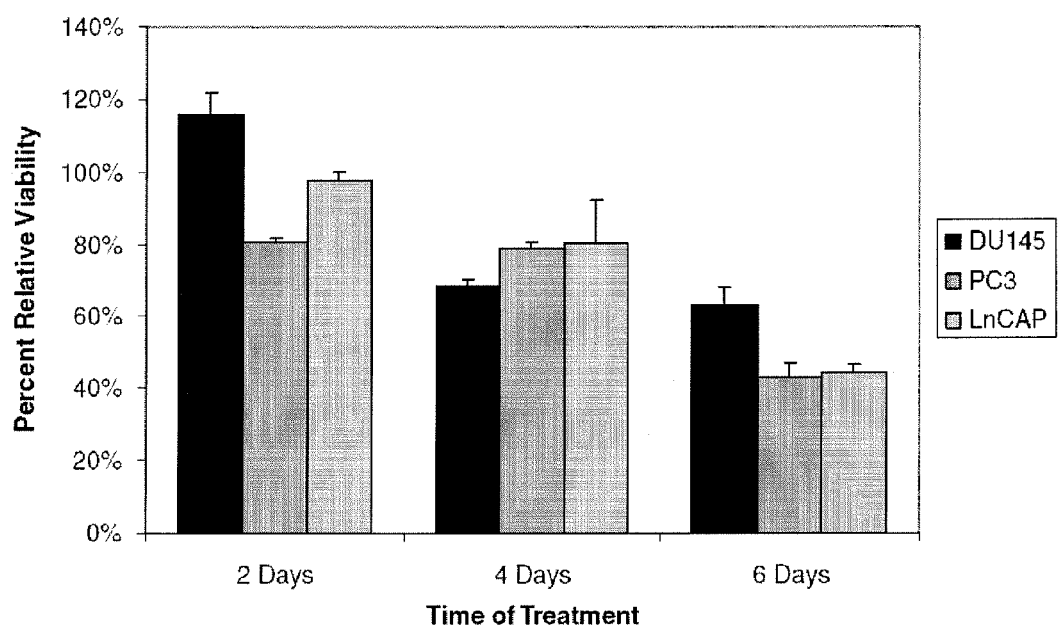

FIG. 38 shows analysis of cell death following siRNA silencing of PAX2. Prostate cancer cell lines PC3, DU145 and LNCaP were treated with PAX2 siRNA or non-specific negative control siRNAs for 2, 4 or 6 days after which MTT assay was performed. Knockdown of PAX2 resulted in a decrease in relative cell viability in all three lines. Results represent mean±SD, n=9.

Figure 39:
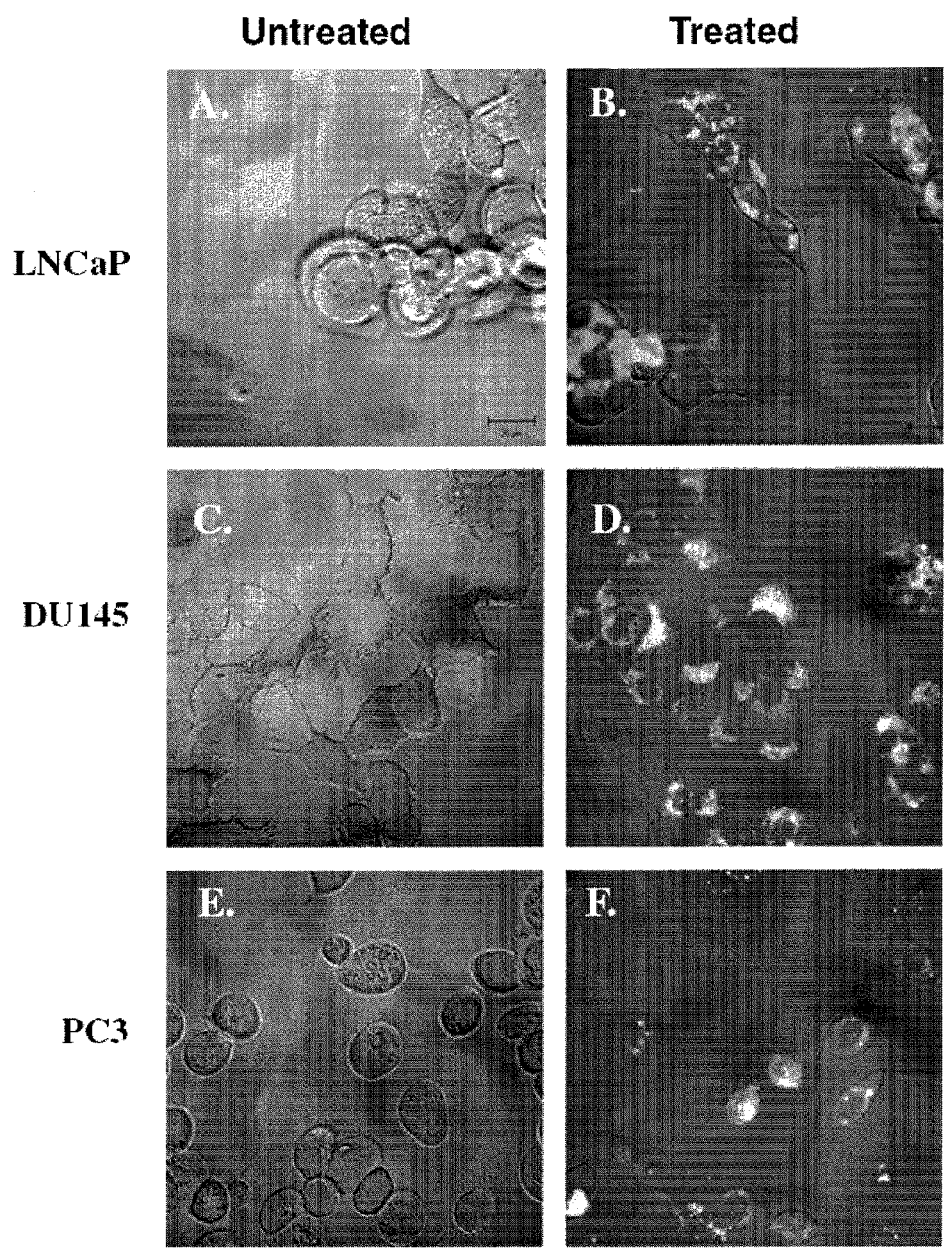

FIG. 39 shows analysis of caspase activity. DU145, PC3 and LNCaP cells were stained with carboxyfluorescein-labeled fluoromethyl ketone to detected caspase activity following treatment with PAX2 siRNA. Analysis under fluorescence revealed no caspase staining in control DU145 (Panel A), PC3 cells (Panel C) and LNCaP cells (Panel E). However, cell treated with PAX2 siRNA induced caspase activity in DU145 (Panel B), PC3 (Panel D) and LNCaP (Panel F). Bar=20 µm.

Figure 40A:
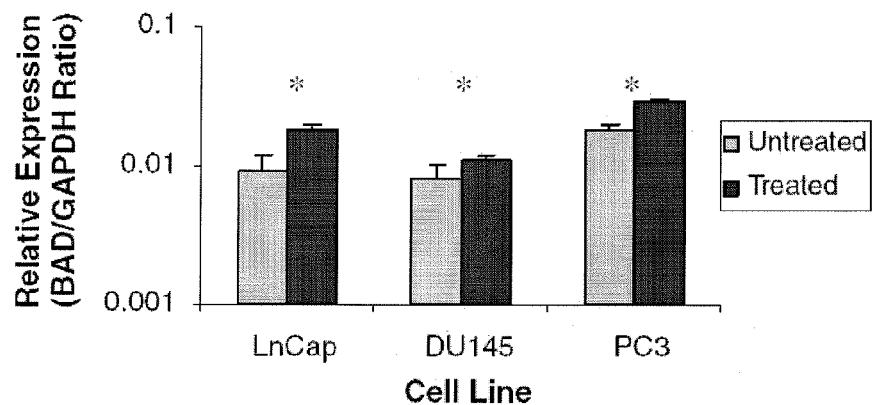
Figure 40B:
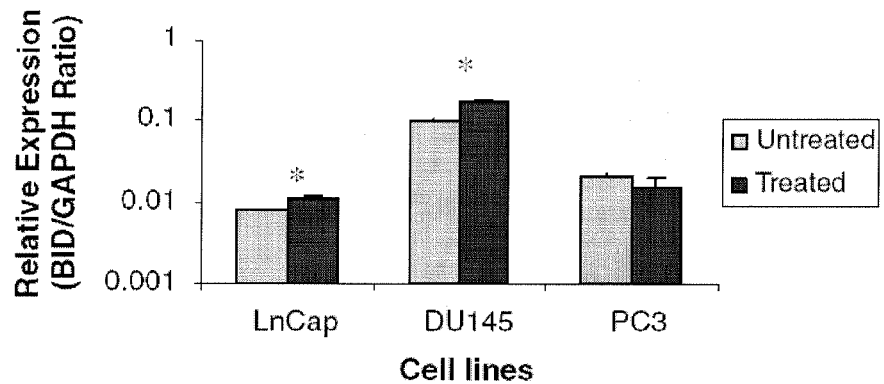
Figure 40C:
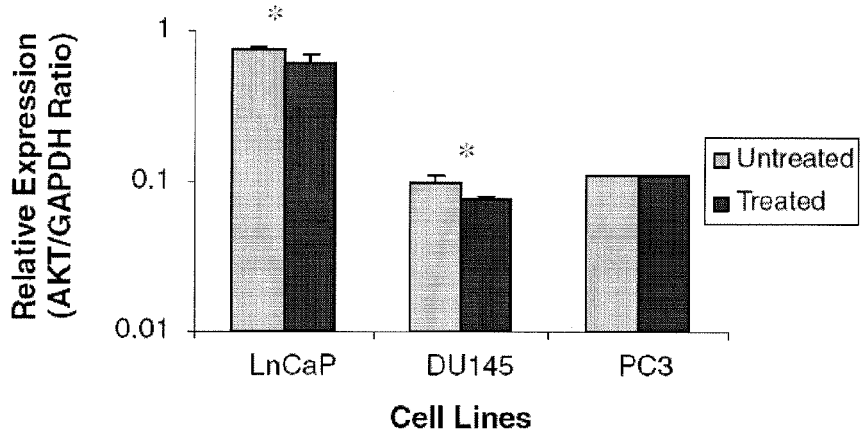

FIGS. 40A-40C show analysis of apoptotic factors following PAX2 siRNA treatment. Changes in expression of pro-apoptotic factors were compared in untreated control cells and in cells treated for 6 days with PAX2 siRNA. FIG. 40A shows BAD expression increased in DU145, PC3 and LNCaP following PAX2 knockdown. FIG. 40B shows BID expression levels increased in LNCaP and DU145, but not in PC3 cells. FIG. 40C shows AKT expression decreased in LNCaP and DU145. However, there was no change in AKT expression in PC3 cells following PAX2 knockdown. Results represent mean±SD, n=9. Asterisks represents statistical differences (p<0.05).

DETAILED DESCRIPTION

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

One aspect of the present invention relates to a method for monitoring cancer development. In certain embodiments, the method relates to monitoring pre-cancerous conditions, such as intraepithelial neoplasia, and cancerous conditions in the prostate or breast of a subject. The method comprises determining a Paired Box 2 gene-to-beta defensin-1 gene (PAX2-to-DEFB1) expression ratio in cells obtained from the prostate or breast of the subject, wherein the PAX2-to-DEFB1 expression ratio is correlated with prostate or breast conditions. The gene expression ratio may be determined at the mRNA level (e.g., by RT-PCR or oligonucleotide array) or at the protein level (e.g., by Western blot or antibody array).

In certain embodiments, the PAX2-to-DEFB1 expression ratio is determined at the mRNA level and is referred to as the "Donald Predictive Factor" or "DPF" in the specification.

In certain embodiments, the PAX2-to-DEFB1 expression ratio (determined at the RNA level) in prostate is used for distinguishing among normal, pre-cancerous and cancerous prostate conditions in the subject. In one embodiment, a PAX2-to-DEFB1 ratio of less than 40:1 is indicative of a normal prostate condition, a PAX2-to-DEFB1 ratio of at least 40:1 to less than 100:1 is indicative of prostate intraepithelial neoplasia (PIN), and a PAX2-to-DEFB1 ratio of at least 100:1 is indicative of prostate cancer.

Also provided is a method for diagnosing prostate cancer in a subject. The method comprises detecting in cells from the prostate of the subject levels of PAX2 and beta defensin-1 (DEFB1), wherein the ratio of PAX2 to DEFB1 is at least 100:1.

Also provided is a method of diagnosing prostate intraepithelial neoplasia (PIN) in a subject. The method comprises detecting in cells from the prostate of the subject levels of PAX2 and beta DEFB1, wherein the ratio of PAX2 to DEFB1 is at least 40:1 and less than 100:1.

In certain other embodiments, the PAX2-to-DEFB1 expression ratio (at the RNA level) in breast is used for distinguishing among non-cancerous (benign and/or pre-cancerous) and cancerous breast conditions in the subject. In one embodiment, a PAX2-to-DEFB1 ratio less than 100:1 is indicative of non-cancerous (normal) and/or pre-cancerous (mammary intraepithelial neoplasia (MIN)), and a PAX2-to-DEFB1 ratio of at least 100:1 is indicative of breast cancer.

Also provided is a method for diagnosing breast cancer in a subject. The method comprises detecting in cells from the breast of the subject levels of PAX2 and DEFB1, wherein the ratio of PAX2 to DEFB1 of at least 100:1 is indicative of breast cancer in the subject. Also provided is a method of diagnosing non-cancerous breast conditions (normal and/or MIN) in a subject. The method comprises detecting in cells from the breast of the subject levels of PAX2 and DEFB1, wherein the ratio of PAX2 to DEFB1 of less than 100:1 is indicative of non-cancerous breast conditions in the subject.

In one embodiment, the method further comprising determining an oestrogen receptor/progesterone receptor (ER/PR) status in cells obtained from the breast tissue with the breast condition. The ER/PR status of the breast tissue may be used, in combination with the PAX2-to-DEFB1 ratio in the same tissue, for determining the breast conditions in the subject.

As used hereinafter, the term "mammary intraepithelial neoplasia" includes lobular intraepithelial neoplasia and ductal intraepithelial neoplasia.

The monitoring and diagnosing methods of the present invention provide clinicians with a prognosticator for initiated or pre-cancerous tissue. Candidates for this test include patients at high risk (based on age, race) for cancer. As a diagnostic, a positive or negative PAX2 test can then be followed by additional screening with biomarker to determine cancer site. In addition, these patients can be candidates for treatment with PAX2/DEFB1 modulators. Alternatively, this test can be used on patients (i.e., those with triple negative breast cancer) as a measure of the effectiveness of their cancer therapy, to determine treatment course, or to monitor cancer recurrence.

As another example, patients who present with potential indicators of cancer such as the detection of nodules in the prostate during a digital rectal exam by the clinician, or those who experience a sudden rise in PSA often are in the "Watchful Waiting" state. It is often difficult to ascertain whether these patients have or will develop cancer. The detection of PAX2-to-DEFB1 ratio in samples, such as plasma/serum, from these patients can be used to assist the decision to obtain a biopsy in men with suspected prostate cancer, which can lead to a reduction in the number of unnecessary prostatic biopsies and earlier intervention for their disease.

Prostate Cancer

Prostate cancer screening currently consists of a rectal examination and measurement of prostate specific antigen (PSA) levels. These methods lack specificity as digital rectal examination has considerable inter-examiner variability and PSA levels may be elevated in benign prostatic hyperplasia (BPH), prostatic inflammation and other conditions.

Prostate cancers can be scored using the Gleason system (Gleason, et al. 1966). This uses tissue architecture rather than cytological features. A grade of 1 to 5 (well to poorly differentiated) is used, and the combined score of the most frequent and more severe areas of the lesion are combined. Gleason scores provide prognostic information that may be valuable in addition to the assessment of the stage of the tumor (staging). Gleason scores of 2 to 4 and 8 to have good predictive value, but about three quarters of tumors have intermediate values.

Two principal systems are used for staging prostate cancer: TNM and the Jewett system (Benson & Olsson, et al. 1989). Staging takes in to account any metastatic spread of the tumor and is difficult, because it is difficult to assess either local lymph node involvement or local invasion. Tumor size is also difficult to measure as tumor tissue cannot be distinguished macroscopically from normal prostate tissue, and because the prostate gland lacks a distinct capsule and is surrounded by a layer of fibrous fatty tissue.

Four categories describe the prostate tumor's (T) stage, ranging from T1 to T4. For T1, the cancer is microscopic, unilateral and non palpable. The doctor can't feel the tumor or see it with imaging such as transrectal ultrasound. Treatment for BPH may have disclosed the disease, or it was confirmed through the use of a needle biopsy done because of an elevated PSA. For T2, the doctor can feel the cancer with a DRE. It appears the disease is confined to the prostate gland on one or both sides of the gland. For T3, the cancer has advanced to tissue immediately outside the gland. For T4, the cancer has spread to other parts of the body.

Present screening methods are therefore unsatisfactory; there is no reliable method for diagnosing prostate cancer, or predicting or preventing its possible metastatic spread, which is the main cause of death for most patients.

Breast Cancer

The commonly used screening methods for breast cancer include self and clinical breast exams, x-ray mammography, and breast Magnetic Resonance Imaging (MRI). The most recent technology for breast cancer screening is ultrasound computed tomography, which uses sound waves to create a three-dimensional image and detect breast cancer without the use of dangerous radiation used in x-ray mammography. Genetic testing may also be used. Genetic testing for breast cancer typically involves testing for mutations in the BRCA genes. It is not a generally recommended technique except for those at elevated risk for breast cancer.

The incidence of breast cancer, a leading cause of death in women, has been gradually increasing in the United States over the last thirty years. While the pathogenesis of breast cancer is unclear, transformation of normal breast epithelium to a malignant phenotype may be the result of genetic factors, especially in women under 30 (Miki et al., 1994, Science, 266:66-71). The discovery and characterization of BRCA1 and BRCA2 has recently expanded our knowledge of genetic factors which can contribute to familial breast cancer. Germline mutations within these two loci are associated with a 50 to 85% lifetime risk of breast and/or ovarian cancer (Casey, 1997, Curr. Opin. Oncol. 9:88-93; Marcus et al, 1996, Cancer 77:697-709). However, it is likely that other, non-genetic factors also have a significant effect on the etiology of the disease. Regardless of its origin, breast cancer morbidity and mortality increases significantly if it is not detected early in its progression. Thus, considerable effort has focused on the early detection of cellular transformation and tumor formation in breast tissue.

Currently, the principal manner of identifying breast cancer is through detection of the presence of dense tumorous tissue. This may be accomplished to varying degrees of effectiveness by direct examination of the outside of the breast, or through mammography or other X-ray imaging methods (Jatoi, 1999, Am. J. Surg. 177:518-524). The latter approach is not without considerable cost, however. Every time a mammogram is taken, the patient incurs a small risk of having a breast tumor induced by the ionizing properties of the radiation used during the test. In addition, the process is expensive and the subjective interpretations of a technician can lead to imprecision, e.g., one study showed major clinical disagreements for about one-third of a set of mammograms that were interpreted individually by a surveyed group of radiologists. Moreover, many women find that undergoing a mammogram is a painful experience. Accordingly, the National Cancer Institute has not recommended mammograms for women under fifty years of age, since this group is not as likely to develop breast cancers as are older women. It is compelling to note, however, that while only about 22% of breast cancers occur in women under fifty, data suggests that breast cancer is more aggressive in pre-menopausal women.

PAX2

PAX genes are a family of nine developmental control genes coding for nuclear transcription factors. They play an important role in embryogenesis and are expressed in a very ordered temporal and spatial pattern. They all contain a "paired box" region of 384 base pairs encoding a DNA binding domain which is highly conserved throughout evolution (Stuart, E T, et al. 1994). The influence of Pax genes on developmental processes has been demonstrated by the numerous natural mouse and human syndromes that can be attributed directly to even a heterozygous insufficiency in a Pax gene. A PAX2 sequence is given in Dressler, et al. 1990. The amino acid sequences of the human PAX2 protein and its variants, as well as the DNA sequences encoding the proteins, are listed in SEQ ID NOS: 58-69 (SEQ ID NO:58, amino acid sequence encoded by exon 1 of the human PAX2 gene; SEQ ID NO:59, human PAX2 gene promoter and exon 1; SEQ ID NO:60, amino acid sequence of the human PAX2; SEQ ID NO:61, human PAX2 gene; SEQ ID NO:62, amino acid sequence of the human PAX2 gene variant b; SEQ ID NO:63, human PAX2 gene variant b; SEQ ID NO:64, amino acid sequence of the human PAX2 gene variant c; SEQ ID NO:65, human PAX2 gene variant c; SEQ ID NO:66, amino acid sequence of the human PAX2 gene variant d; SEQ ID NO:67, human PAX2 gene variant d; SEQ ID NO:68, amino acid sequence of the human PAX2 gene variant e; SEQ ID NO:69 human PAX2 gene variant e).

Examples of cancers in which PAX2 expression has been detected are listed in Table 1

TABLE 1

| PAX2-expressing cancers | | | | |
|---|---|---|---|---|
| PAX2 Expressing Cancers | Estimated New Cases in US | Estimated Deaths in US | Estimated New Cases Global | Estimated Deaths Global |
| Prostate | 234,460 | 27,350 | 679,023 | 221,002 |
| Breast | 214,600 | 41,430 | 1,151,298 | 410,712 |
| Ovarian | 20,180 | 15,310 | 204,500 | 124,860 |
| Renal | 38,890 | 12,840 | 208,479 | 101,895 |
| Brain | 12,820 | 18,820 | 189,485 | 141,650 |
| Cervical | 9,710 | 3,700 | 493,243 | 273,505 |
| Bladder | 61,420 | 13,060 | 356,556 | 145,009 |
| Leukemia | 35,020 | 22,280 | 300,522 | 222,506 |
| Kaposi Sarcoma | Data Not Available | Data Not Available | Data Not Available | Data Not Available |
| TOTAL(approx.) | 627,100 | 154,790 | 3,583,106 | 1,641,139 |

DEFB1

Beta-defensins are cationic peptides with broad-spectrum antimicrobial activity that are products of epithelia and leukocytes. These two exon, single gene products are expressed at epithelial surfaces and secreted at sites including the skin, cornea, tongue, gingiva, salivary glands, esophagus, intestine, kidney, urogenital tract, and the respiratory epithelium. To date, five beta-defensin genes of epithelial origin have been identified and characterized in humans: DEFB1 (Bensch et al., 1995), DEFB2 (Harder et al., 1997), DEFB3 (Harder et al., 2001; Jia et al., 2001), DEFB4, and HE2/EP2.

The primary structure of each beta-defensin gene product is characterized by small size, a six cysteine motif, high cationic charge and exquisite diversity beyond these features. The most characteristic feature of defensin proteins is their six-cysteine motif that forms a network of three disulfide bonds. The three disulfide bonds in the beta-defensin proteins are between C1-C5, C2-C4 and C3-C6. The most common spacing between adjacent cysteine residues is 6, 4, 9, 6, 0. The spacing between the cysteines in the beta-defensin proteins can vary by one or two amino acids except for C5 and C6, located nearest the carboxy terminus. In all known vertebrate beta-defensin genes, these two cysteine residues are adjacent to each other.

A second feature of the beta-defensin proteins is their small size. Each beta-defensin gene encodes a preproprotein that ranges in size from 59 to 80 amino acids with an average size of 65 amino acids. This gene product is then cleaved by an unknown mechanism to create the mature peptide that ranges in size from 36 to 47 amino acids with an average size of 45 amino acids. The exceptions to these ranges are the EP2/HE2 gene products that contain the beta-defensin motif and are expressed in the epididymis.

A third feature of beta-defensin proteins is the high concentration of cationic residues. The number of positively charged residues (arginine, lysine, histidine) in the mature peptide ranges from 6 to 14 with an average of 9.

The final feature of the beta-defensin gene products is their diverse primary structure but apparent conservation of tertiary structure. Beyond the six cysteines, no single amino acid at a given position is conserved in all known members of this protein family. However, there are positions that are conserved that appear to be important for secondary and tertiary structures and function.

Despite the great diversity of the primary amino acid sequence of the beta-defensin proteins, the limited data suggests that the tertiary structure of this protein family is conserved. The structural core is a triple-stranded, antiparallel beta-sheet, as exemplified for the proteins encoded by BNBD-12 and DEFB2. The three beta-strands are connected by a beta-turn, and an alpha-hairpin loop, and the second beta-strand also contains a beta-bulge. When these structures are folded into their proper tertiary structure, the apparently random sequences of cationic and hydrophobic residues are concentrated into two faces of a globular protein. One face is hydrophilic and contains many of the positively charged side chains and the other is hydrophobic. In solution, the HBD-2 protein encoded by the DEFB2 gene exhibited an alpha-helical segment near the N-terminus not previously ascribed to solution structures of alpha-defensins or to the beta-defensin BNBD-12. The amino acids whose side chains are directed toward the surface of the protein are less conserved between beta defensin proteins while the amino acid residues in the three beta-strands of the core beta-sheet are more highly conserved.

Beta-defensin peptides are produced as pre-pro-peptides and then cleaved to release a C-terminal active peptide fragment; however the pathways for the intracellular processing, storage and release of the human beta-defensin peptides in airway epithelia are unknown.

Determination of PAX2-to-DEFB1 Expression Ratio

Levels of PAX2 and DEFB1 expression in a tissue can be measured any method known in the art. In certain embodiments, the levels of PAX2 and DEFB1 expression in a target tissue are determined by determining the levels of PAX2 and DEFB1 in a cell or cells obtained directly from the target tissue, such as a biopsy sample. In other embodiments, the levels of PAX2 and DEFB1 expression in a target tissue are determined indirectly by determining the levels of PAX2 and DEFB1 in certain body fluids such as blood or plasma.

In certain embodiments, levels of PAX2 and DEFB1 expression in the prostate or breast of the subject can be measured using a cell sample from the prostate or breast. Cell samples include biopsy samples of the prostate or breast and blood sample. Biopsy is a procedure in which small tissue samples are removed from a target organ for further analysis. Prostate biopsy is typically performed when the scores from a PSA blood test rise to a level that is associated with the possible presence of prostate cancer. Similarly, breast biopsy is typically performed in patients with breast lumps or suspicious mammograms.

Levels of gene expression can be evaluated at the RNA and protein levels. The RNA levels may be measured, for example, with DNA arrays, RT-PCR and Northern Blotting. The protein levels may be measured with immunoassays and enzyme assays. In certain embodiments, the PAX2-to-DEFB1 expression ratio is determined by determining the expression level of PAX2 gene relative to the expression level of a control gene, determining the expression level of DEFB1 gene relative to the expression level of the same control gene, and calculating the PAX2-to-DEFB1 expression ratio based on the expression levels of PAX2 and DEFB1. In one embodiment, the control gene is the glyceraldehyde 3-phosphate dehydrogenase (GAPDH) gene.

Oligonucleotide Microarray

An oligonucleotide microarray consists of an arrayed series of a plurality of microscopic spots of oligonucleotides, called features, each containing a small amount (typically in the range of picomoles) of a specific oligonucleotide sequence. The specific oligonucleotide sequence can be a short section of a gene or other oligonucleotide element that are used as probes to hybridize a cDNA or cRNA sample under high-stringency conditions. Probe-target hybridization is usually detected and quantified by fluorescence-based detection of fluorophore-labeled targets to determine relative abundance of nucleic acid sequences in the target.

The probes are typically attached to a solid surface by a covalent bond to a chemical matrix (via epoxy-silane, amino-silane, lysine, polyacrylamide or others). The solid surface can be glass or a silicon chip or microscopic beads. Oligonucleotide arrays are different from other types of microarray only in that they either measure nucleotides or use oligonucleotide as part of its detection system.

To detect gene expression in target tissue or cells using an oligonucleotide array, nucleic acid of interest is purified from the target tissue or cells. The nucleotide can be all RNA for expression profiling, DNA for comparative hybridization, or DNA/RNA bound to a particular protein which is immunoprecipitated (ChIP-on-chip) for epigenetic or regulation studies.

In one embodiment, total RNA is isolated (total as it is nuclear and cytoplasmic) by guanidinium thiocyanate-phenol-chloroform extraction (e.g. Trizol). The purified RNA may be analyzed for quality (e.g., by capillary electrophoresis) and quantity (e.g., by using a nanodrop spectrometer. The total RNA is RNA is reverse transcribed into DNA with either polyT primers or random primers. The DNA products may be optionally amplified by PCR. A label is added to the amplification product either in the RT step or in an additional step after amplification if present. The label can be a fluorescent label or radioactive labels. The labeled DNA products are then hybridized to the microarray. The microarray is then washed and scanned. The expression level of the gene of interest is determined based on the hybridization result using method well known in the art.

Immunoassays

Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

Also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner. Antibody arrays are available commercially. In addition to the conventional antibodies, Fab and scFv fragments, single V-domains from camelids or engineered human equivalents (Domantis, Waltham, Mass.) may also be useful in arrays.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumor extracts, and SELDI-TOF mass spectrometry is used to detection the retained proteins.

Other useful methodology includes large-scale functional chips constructed by immobilizing large numbers of purified proteins on a chip, and multiplexed bead assays.

Antibodies

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with, for example, PAX2 or DEFB1, such that PAX2 is inhibited from interacting with DEFB1. Antibodies that bind the disclosed regions of PAX2 or DEFB1 involved in the interaction between PAX2 and DEFB1 are also disclosed. The antibodies can be tested for their desired activity using the in vitro assays described herein, or by analogous methods, after which their in vivo therapeutic and/or prophylactic activities are tested according to known clinical testing methods.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response. Methods for humanizing non-human antibodies are well known in the art.

Pharmacogenomics

In another embodiment, the PAX2 and/or DEFB1 expression profiles are used for determine pharmacogenomics of breast cancer. Pharmacogenomics refers to the relationship between an individual's genotype and that individual's response to a foreign compound or drug. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an anti-cancer drug, as well as tailoring the dosage and/or therapeutic regimen of treatment with the anti-cancer drug.

Pharmacogenomics deals with clinically significant hereditary variations in the response to drugs due to altered drug disposition and abnormal action in affected persons. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related sites (e.g., a "bi-allelic" gene marker map which consists of 60,000-100,000 polymorphic or variable sites on the human genome, each of which has two variants). Such a high-resolution genetic map can be compared to a map of the genome of each of a statistically substantial number of subjects taking part in a Phase II/III drug trial to identify genes associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, an SNP may occur once per every 1,000 bases of DNA. An SNP may be involved in a disease process. However, the vast majority of SNPs may not be disease associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the PAX2 and/or DEFB1 to SNP maps of breast patients may allow easier identification of these genes according to the genetic methods described herein.

Alternatively, a method termed the "candidate gene approach," can be utilized to identify genes that predict drug response. According to this method, if a gene that encodes a drug target is known, all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYPZC19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a breast condition.

In one embodiment, the PAX2 and/or DEFB1 expression profiles, as well as the ER/PR status, in a subject are used to determine the appropriate treatment regimens for an individual with a breast condition.

In another embodiment, the PAX2 expression level (typically determine in reference to a control gene as actin gene or GAPDH gene) is used in patients with triple negative breast cancer (i.e., oestrogen receptor (ER) negative, progesterone receptor (PR) negative, human epidermal growth factor receptor 2 (HER2) negative) to measure of the effectiveness of cancer therapy, to determine treatment course, or to monitor cancer recurrence.

Diagnosis Kits

Another aspect of the present invention relates to a kit for monitoring breast conditions. In one embodiment, the kit for monitoring breast conditions comprises: one or more pairs of oligonucleotide primers for detecting PAX2 expression in a tissue sample, one or more pairs of oligonucleotide primers for detecting DEFB1 expression in the tissue sample, and instructions on how to determine the PAX2-to-DEFB1 expression ratio in a tissue sample using the primers. In another embodiment, the one or more pairs of oligonucleotide primers for detecting PAX2 expression comprising an oligonucleotide primer pair selected from the group consisting of SEQ ID NOS: 43 and 47, SEQ ID NOS: 44 and 48, and SEQ ID NOS: 45 and 49. In another embodiment, the one or more pairs of oligonucleotide primers for detecting DEFB1 expression comprising SEQ ID NOS: 35 and 37.

In another embodiment, the kit further comprises one or more pairs of control oligonucleotide primers. In one embodiment, the one or more pairs of control oligonucleotide primers comprise oligonucleotide primers for detecting expression of β-actin expression. In a preferred embodiment, the oligonucleotide primers for detecting expression of β-actin expression comprise SEQ ID NOS: 34 and 36.

In another embodiment, the one or more pairs of control oligonucleotide primers comprise oligonucleotide primers for detecting expression of GAPDH expression. In a preferred embodiment, the oligonucleotide primers for detecting expression of GAPDH expression comprise SEQ ID NOS: 42 and 46.

In another related embodiment, the kit further comprises one or more reagents for PCR reaction.

In yet another related embodiment, the kit further comprises one or more reagents for RNA extraction.

In another embodiment, the kit for monitoring breast conditions comprises an oligonucleotide microarray having oligonucleotide probes for detecting PAX2 and DEFB1 expression and instructions on how to determine the PAX2-to-DEFB1 expression ratio in a tissue sample using the oligonucleotide microarray.

In a related embodiment, the kit further comprises reagents for extracting RNA from a tissue sample.

The present invention is further illustrated by the following examples which should not be construed as limiting. The contents of all references, patents and published patent applications cited throughout this application, as well as the Figures and Tables are incorporated herein by reference.

EXAMPLE 1

Human Beta Defensin-1 is Cytotoxic to Late-Stage Prostate Cancer and Plays a Role in Prostate Cancer Tumor Immunity In this example, DEFB1 was cloned into an inducible expression system to examine what effect it had on normal prostate epithelial cells, as well as androgen receptor positive (AR+) and androgen receptor negative (AR−) prostate cancer cell lines. Induction of DEFB1 expression resulted in a decrease in cellular growth in AR− cells DU145 and PC3, but had no effect on the growth of the AR+ prostate cancer cells LNCaP. DEFB1 also caused rapid induction of caspase-mediated apoptosis. Data presented here are the first to provide evidence of its role in innate tumor immunity and indicate that its loss contributes to tumor progression in prostate cancer.

Materials and Methods

Cell Lines: The cell lines DU145 were cultured in DMEM medium, PC3 were grown in F12 medium, and LNCaP were grown in RPMI medium (Life Technologies, Inc., Grand Island, N.Y.). Growth media for all three lines was supplemented with 10% (v/v) fetal bovine serum (Life Technologies). The hPrEC cells were cultured in prostate epithelium basal media (Cambrex Bio Science, Inc., Walkersville, Md.). All cell lines were maintained at 37° C. and 5% CO2.

Tissue Samples and Laser Capture Microdissection: Prostate tissues obtained from consented patients that underwent radical prostatectomy were acquired through the Hollings Cancer Center tumor bank in accordance with an Institutional Review Board-approved protocol. This included guidelines for the processing, sectioning, histological characterization, RNA purification and PCR amplification of samples. Following pathologic examination of frozen tissue sections, laser capture microdissection (LCM) was performed to ensure that the tissue samples assayed consisted of pure populations of benign prostate cells. For each tissue section analyzed, LCM was performed at three different regions containing benign tissue and the cells collected were then pooled.

Cloning of DEFB1 Gene: DEFB1 cDNA was generated from RNA by reverse transcription-PCR. The PCR primers were designed to contain ClaI and KpnI restriction sites. DEFB1 PCR products were restriction digested with ClaI and KpnI and ligated into a TA cloning vector. The TA/DEFB1 vector was then transfected into E. coli by heat shock and individual clones were selected and expanded. Plasmids were isolated by Cell Culture DNA Midiprep (Qiagen, Valencia, Calif.) and sequence integrity verified by automated sequencing. The DEFB1 gene fragment was then ligated into the pTRE2 digested with ClaI and KpnI, which served as an intermediate vector for orientation purposes. Then the pTRE2/DEFB1 construct was digested with ApaI and KpnI to excise the DEFB1 insert, which was ligated into pIND vector of the Ecdysone Inducible Expression System (Invitrogen, Carlsbad, Calif.) also double digested with ApaI and KpnI. The construct was again transfected into E. coli and individual clones were selected and expanded. Plasmids were isolated and sequence integrity of pIND/DEFB1 was again verified by automated sequencing.

Transfection: Cells ($1\times10^6$) were seeded onto 100-mm Petri dishes and grown overnight. Then the cells were co-transfected using Lipofectamine 2000 (Invitrogen, Carlsbad, Calif.) with 1 µg of pVgRXR plasmid, which expresses the heterodimeric ecdysone receptor, and 1 µg of the pIND/DEFB1 vector construct or empty pIND control vector in Opti-MEM media (Life Technologies, Inc., Grand Island, N.Y.).

RNA Isolation and Quantitative RT-PCR: In order to verify DEFB1 protein expression in the cells transfected with DEFB1 construct, RNA was collected after a 24 hour induction period with Ponasterone A (Pon A). Briefly, total RNA was isolated using the SV Total RNA Isolation System (Promega, Madison, Wis.) from approximately $1\times10^6$ cells harvested by trypsinizing. Here, cells were lysed and total RNA was isolated by centrifugation through spin columns. For cells collected by LCM, total RNA was isolated using the PicoPure RNA Isolation Kit (Arcturus Biosciences, Mt. View, Calif.) following the manufacturer's protocol. Total RNA (0.5 µg per reaction) from both sources was reverse transcribed into cDNA utilizing random primers (Promega). AMV Reverse Transcriptase II enzyme (500 units per reaction; Promega) was used for first strand synthesis and Tfl DNA Polymerase for second strand synthesis (500 units per reaction; Promega) as per the manufacturer's protocol. In each case, 50 pg of cDNA was used per ensuing PCR reaction. Two-step QRT-PCR was performed on cDNA generated using the MultiScribe Reverse Transcripatase from the TaqMan Reverse Transcription System and the SYBR® Green PCR Master Mix (Applied Biosystems).

The primer pair for DEFB1 (Table 2) was generated from the published DEFB1 sequence (GenBank Accession No. U50930). Forty cycles of PCR were performed under standard conditions using an annealing temperature of 56° C. In addition, β-actin (Table 3) was amplified as a housekeeping gene to normalize the initial content of total cDNA. DEFB1 expression was calculated as the relative expression ratio between DEFB1 and β-actin and was compared in cells lines induced and uninduced for DEFB1 expression, as well as LCM benign prostatic tissue. As a negative control, QRT-PCR reactions without cDNA template were also performed. All reactions were run three times in triplicate.

TABLE 2

Sequences of QRT-PCR Primers.

| | Sense (5'-3') | |
|---|---|---|
| β-actin | 5'-CCTGGCACCCAGCACAAT-3' | SEQ ID NO: 34 |
| DEFB1 | 5'-GTTGCCTGCCAGTCGCCATGA GAACTTCCTAC-3' | SEQ ID NO: 35 |
| | Antisense (5'-3') | |
| β-actin | 5'-GCCGATCCACACGGAGTACT-3' | SEQ ID NO: 36 |
| DEFB1 | 5'-TGGCCTTCCCTCTGTAACAGGT GCCTTGAATT-3' | SEQ ID NO: 37 |

MTT Cell Viability Assay: To examine the effects of DEFB1 on cell growth, metabolic 3-[4,5-dimethylthiazol-2-yl]-2,5 diphenyl tetrazolium bromide (MTT) assays were performed. PC3, DU145 and LNCaP cells co-transfected with pVgRXR plasmid and pIND/DEFB1 construct or empty pIND vector were seeded onto a 96-well plate at $1-5\times10^3$ cells per well. Twenty-four hours after seeding, fresh growth medium was added containing 10 µM Ponasterone A daily to induce DEFB1 expression for 24-, 48- and 72 hours after which the MTT assay was performed according to the manufacturer's instructions (Promega). Reactions were performed three times in triplicate.

Flow Cytometry: PC3 and DU145 cells co-transfected with the DEFB1 expression system were grown in 60-mm dishes and induced for 12, 24, and 48 hours with 10 µM Ponasterone A. Following each incubation period, the medium was collected from the plates (to retain any detached cells) and combined with PBS used to wash the plates. The remaining attached cells were harvested by trypsinization and combined with the detached cells and PBS. The cells were then pelleted at 4° C. (500×g) for 5 min, washed twice in PBS, and resuspended in 100 µl of 1× Annexin binding buffer (0.1 M Hepes/NaOH at pH 7.4, 1.4 M NaCl, 25 mM CaCl2)

containing 5 μl of Annexin V-FITC and 5 μl of PI. The cells were incubated at RT for min in the dark, then diluted with 4001 of 1×Annexin binding buffer and analyzed by FACscan (Becton Dickinson, San Jose, Calif.). All reactions were performed three times.

Microscopic Analysis: Cell morphology was analyzed by phase contrast microscopy. DU145, PC3 and LNCaP cells containing no vector, empty plasmid or DEFB1 plasmid were seeded onto 6 well culture plates (BD Falcon, USA). The following day plasmid-containing cells were induced for a period of 48 h with media containing 10 μM Ponasterone A, while control cells received fresh media. The cells were then viewed under an inverted Zeiss IM 35 microscope (Carl Zeiss, Germany). Phase contrast pictures of a field of cells were obtained using the SPOT Insight Mosaic 4.2 camera (Diagnostic Instruments, USA). Cells were examined by phase contrast microscopy under 32× magnification and digital images were stored as uncompressed TIFF files and exported into Photoshop CS software (Adobe Systems, San Jose, Calif.) for image processing and hard copy presentation.

Caspase Detection: Detection of caspase activity in the prostate cancer cell lines was performed using APO LOGIX™ Carboxyfluorescin Caspase detection kit (Cell Technology, Mountain View, Calif.). Active caspases were detected through the use of a FAM-VAD-FMK inhibitor that irreversibly binds to active caspases. Briefly, DU145 and PC3 cells (1.5-3×105) containing the DEFB1 expression system were plated in 35 mm glass bottom microwell dishes (Matek, Ashland, Mass.) and treated for 24 hours with media only or with media containing PonA as previously described. Next, 101 of a 30× working dilution of carboxyfluorescein labeled peptide fluoromethyl ketone (FAM-VAD-FMK) was added to 300 μl of media and added to each 35 mm dish. Cells were then incubated for 1 hour at 37° C. under 5% CO2. Then, the medium was aspirated and the cells were washed twice with 2 ml of a 1× Working dilution Wash Buffer. Cells were viewed under differential interference contrast (DIC) or under laser excitation at 488 nm. The fluorescent signal was analyzed using a confocal microscope (Zeiss LSM 5 Pascal) and a 63×DIC oil lens with a Vario 2 RGB Laser Scanning Module.

Statistical Analysis: Statistical differences were evaluated using the Student's t-test for unpaired values. P values were determined by a two-sided calculation, and a P value of less than 0.05 was considered statistically significant.

Figure 1A:
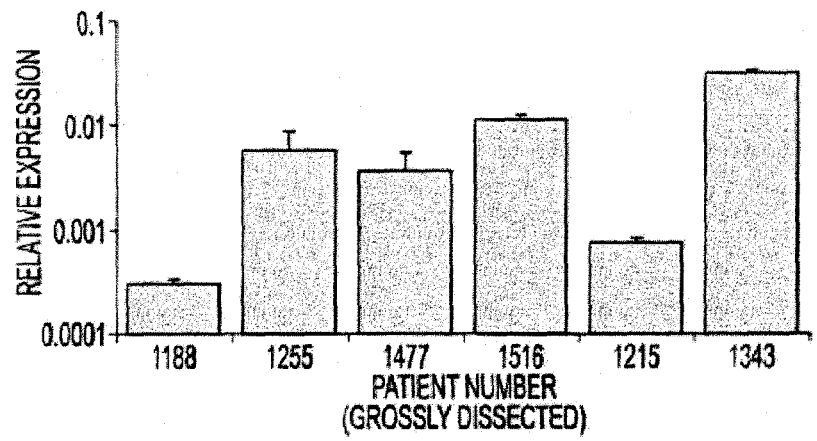
FIGS. 1A-1D show quantitative RT-PCR (QRT-PCR) analysis of beta-defensin-1 (DEFB1) expression. In order to verify induction of DEFB1 expression, QRT-PCR was performed.
Figure 1B:
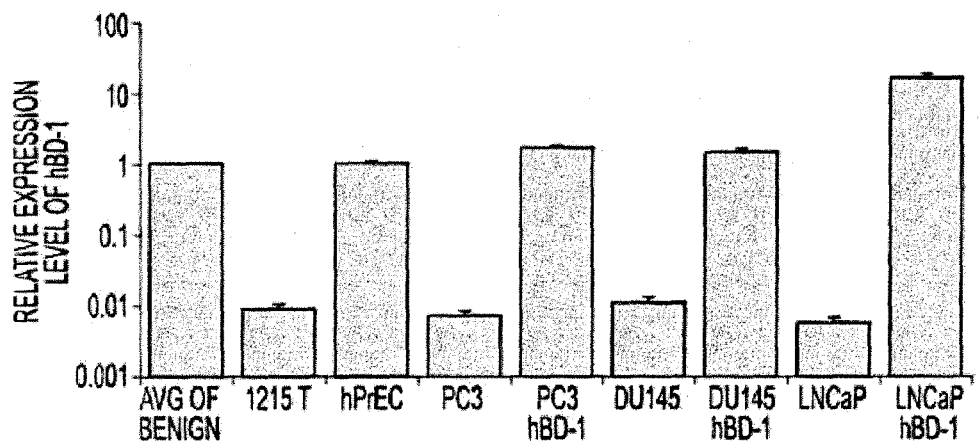

DEFB1 Expression in Prostate Tissue and Cell Lines: DEFB1 expression levels were measured by QRT-PCR in benign and malignant prostatic tissue, hPrEC prostate epithelial cells and DU145, PC3 and LNCaP prostate cancer cells. DEFB1 expression was detected in all of the benign clinical samples. The average amount of DEFB1 relative expression was 0.0073. In addition, DEFB1 relative expression in hPrEC cells was 0.0089. There was no statistical difference in DEFB1 expression detected in the benign prostatic tissue samples and hPrEC (FIG. 1A). Analysis of the relative DEFB1 expression levels in the prostate cancer cell lines revealed significantly lower levels in DU145, PC3 and LNCaP. As a further point of reference, relative DEFB1 expression was measured in the adjacent malignant section of prostatic tissue from patient #1215. There were no significant differences in the level of DEFB1 expression observed in the three prostate cancer lines compared to malignant prostatic tissue from patient #1215 (FIG. 1B). In addition, expression levels in all four samples were close to the no template negative controls which confirmed little to no endogenous DEFB1 expression (data not shown). QRT-PCR was also performed on the prostate cancer cell lines transfected with the DEFB1 expression system. Following a 24 hour induction period, relative expression levels were 0.01360 in DU145, 0.01503 in PC3 and 0.138 in LNCaP. Amplification products were verified by gel electrophoresis.

Figure 1C:
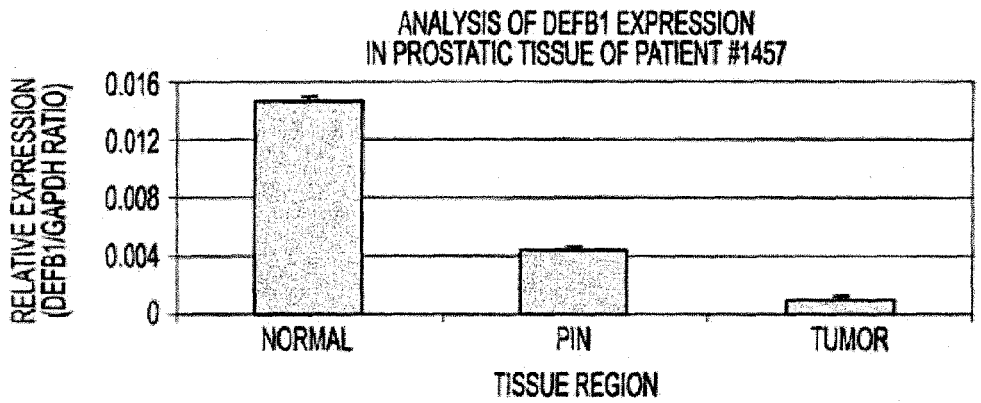
Figure 1D:
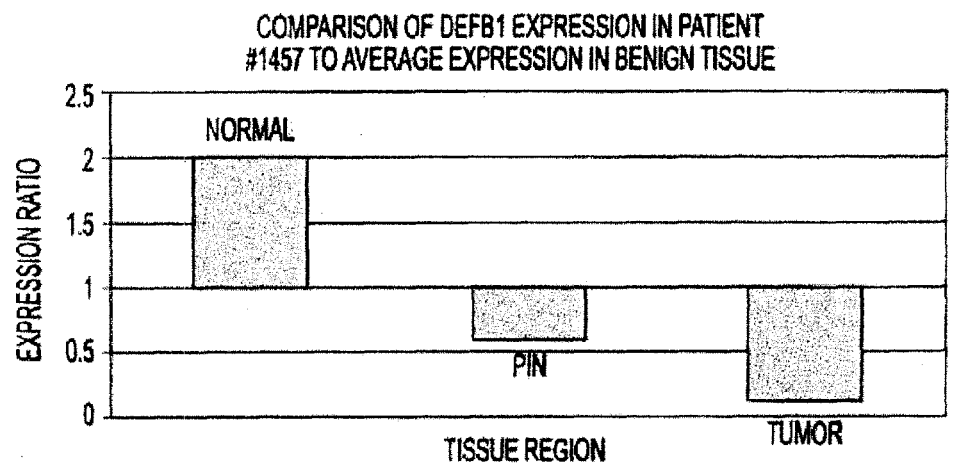

QRT-PCR was performed on LCM tissues regions containing benign, PIN and cancer. DEFB1 relative expression was 0.0146 in the benign region compared to 0.0009 in the malignant region (FIG. 1C). This represents a 94% decrease which again demonstrates a significant down-regulation of expression. Furthermore, analysis of PIN revealed that DEFB1 expression level was 0.044 which was a 70% decrease. Comparing expression in patient #1457 to the average expression level found in benign regions of six other patients (FIG. 1A.) revealed a ratio of 1.997 representing almost twice as much expression (FIG. 1D). However, the expression ratio was 0.0595 in PIN and was 0.125 in malignant tissue compared to average expression levels in benign tissue.

Figure 2:
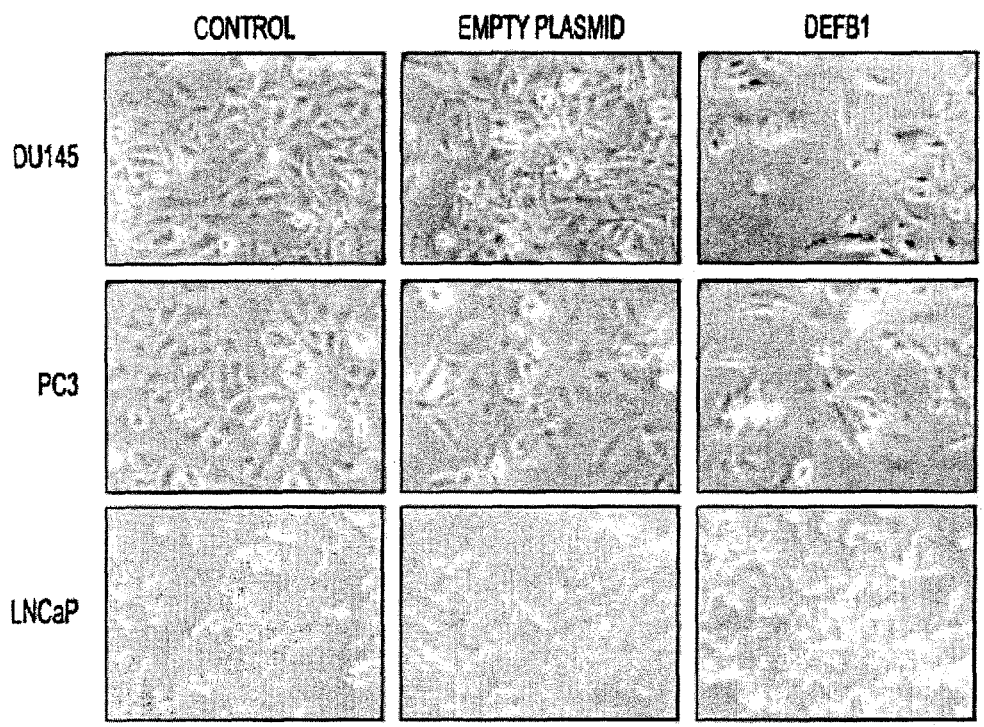
FIG. 2 shows microscopic analysis of DEFB1 induced changes in membrane integrity and cell morphology. Cell morphology of DU145, PC3 and LNCaP was analyzed by phase contrast microscopy after 48 hours of DEFB1 induction. Membrane ruffling is indicated by black arrows and apoptotic bodies are indicated white arrows.

DEFB1 Causes Cell Membrane Permeability and Ruffling: Induction of DEFB1 in the prostate cancer cell lines resulted in a significant reduction in cell number in DU145 and PC3, but had no effect on cell proliferation in LNCaP (FIG. 2). As a negative control, cell proliferation was monitored in all three lines containing empty plasmid. There were no observable changes in cell morphology in DU145, PC3 or LNCaP cells following the addition of PonA. In addition, DEFB1 induction resulted in morphological changes in both DU145 and PC3. Here cells appeared more rounded and exhibited membrane ruffling indicative of cell death. Apoptotic bodies were also present in both lines.

Figure 3:
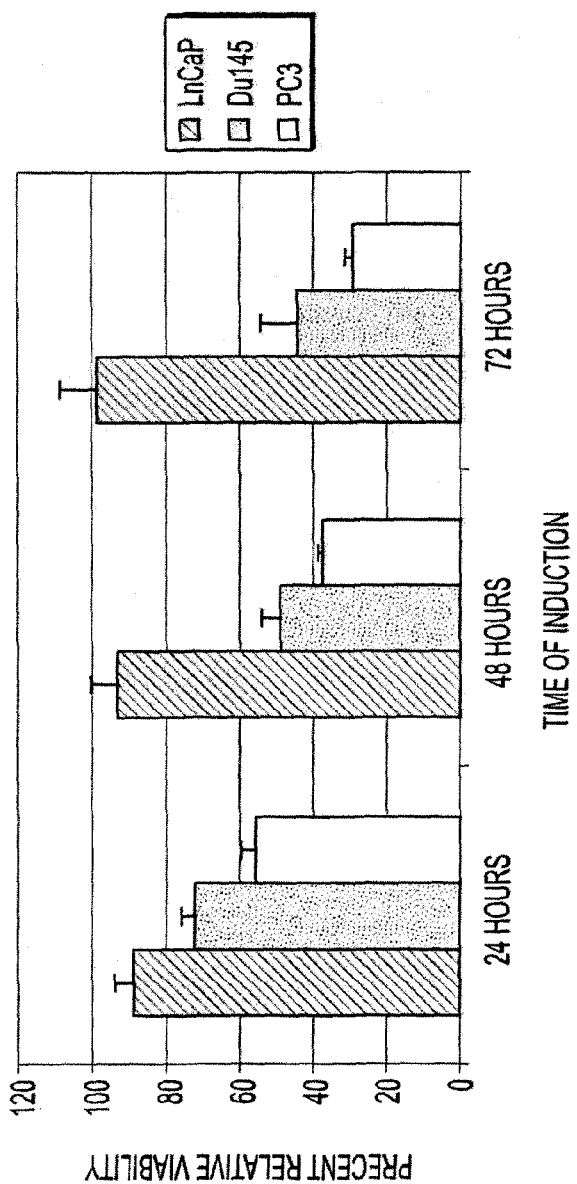
FIG. 3 shows analysis of DEFB1 Cytotoxicity in Prostate Cancer Cells. The prostate cell lines DU145, PC3 and LNCaP were treated with PonA to induce DEFB1 expression for 1-3 days after which MTT assay was performed to determine cell viability. Results represent mean±s.d., n=9.

Expression of DEFB1 Results in Decreased Cell Viability: The MTT assay showed a reduction in cell viability by DEFB1 in PC3 and DU145 cells, but no significant effect on LNCaP cells (FIG. 3). After 24 hours, relative cell viability was 72% in DU145 and 56% in PC3. Analysis 48 hours after induction revealed 49% cell viability in DU145 and 37% cell viability in PC3. After 72 hours of DEFB1 expression resulted in 44% and 29% relative cell viability in DU145 and PC3 cells, respectively.

Figure 4A:
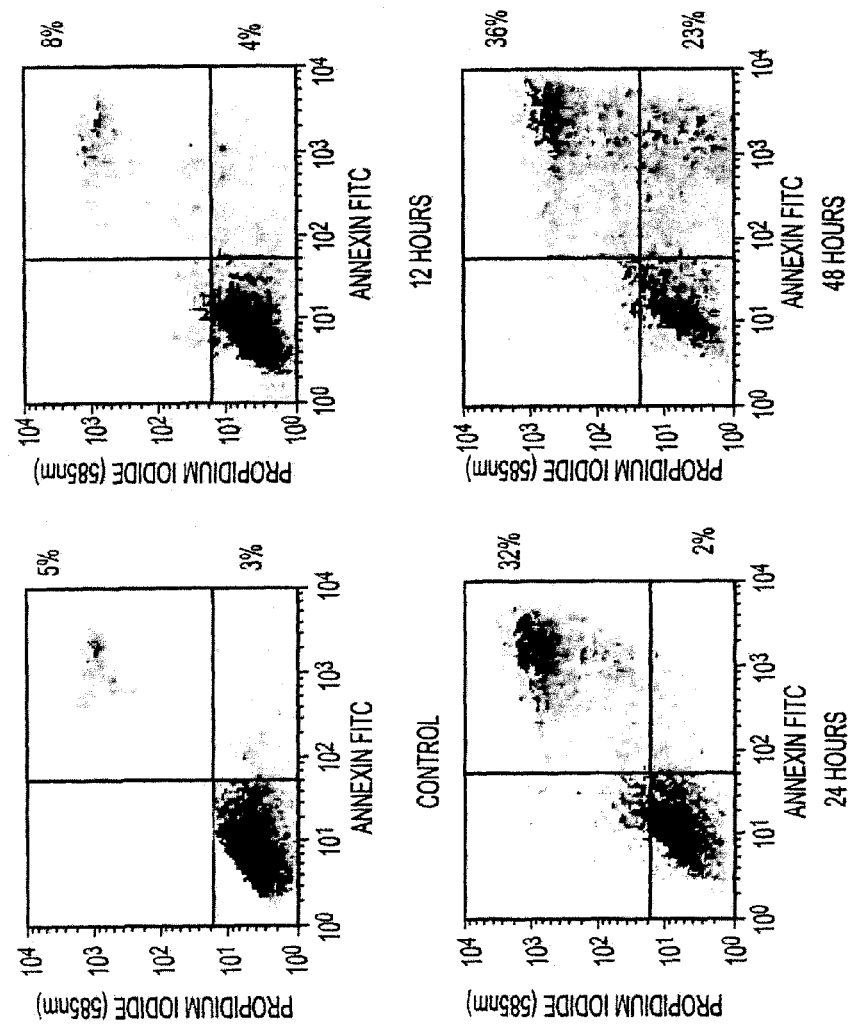
FIG. 4A and FIG. 4B show induction of cell death in DU145 and PC3 cells by DEFB1. DEFB1 expression was induced in prostate cancer cell lines DU145 (FIG. A) and PC3 (FIG. B) and then subjected to annexin V/FITC/propidium iodide staining and flow cytometric analysis. Cells positive for propidium iodide and annexin V were considered apoptotic. Times of induction are shown under each panel. Numbers next to the boxes for each time point represent the percentages of propidium iodide (PI)– annexin V+ cells (lower right quadrant), and PI+ annexin V+ cells (upper right quadrant). The data are from a single experiment that is representative of three separate experiments.
Figure 4B:
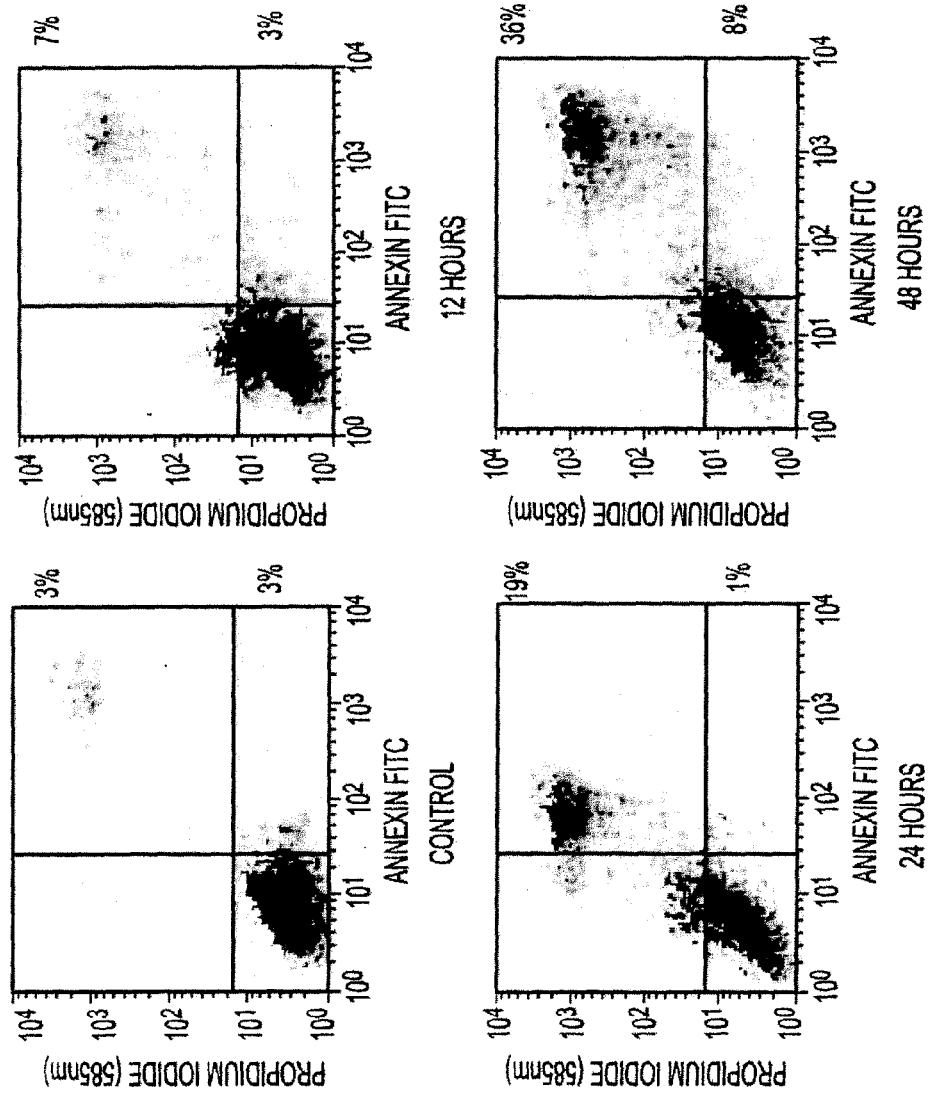

DEFB1 Causes Rapid Caspase-mediated Apoptosis in Late-stage Prostate Cancer Cells: In order to determine whether the effects of DEFB1 on PC3 and DU145 were cytostatic or cytotoxic, FACS analysis was performed (FIGS. 4 and 4B). Under normal growth conditions, more than 90% of PC3 and DU145 cultures were viable and non-apoptotic (lower left quadrant) and did not stain with annexin V or PI. After inducing DEFB1 expression in PC3 cells, the number of apoptotic cells (lower and upper right quadrants) totaled 10% at 12 hours, 20% at 24 hours, and 44% at 48 hours. For DU145 cells, the number of apoptotic cells totaled 12% after 12 hours, 34% at 24 hours, and 59% after 48 hours of induction. There was no increase in apoptosis observed in cells containing empty plasmid following induction with PonA (data not shown).

Figure 5:
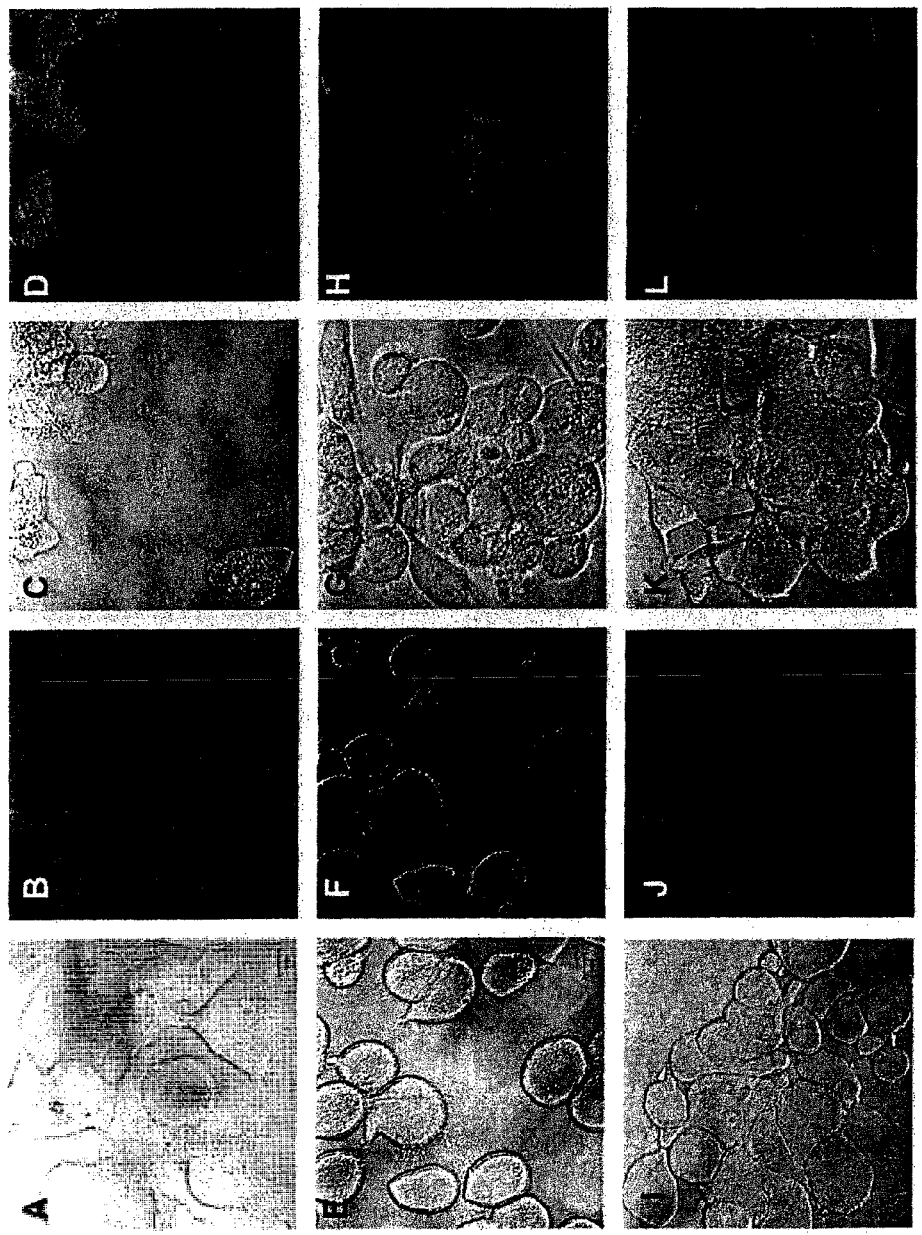
FIG. 5 shows pan-caspase analysis following DEFB1 induction in DU145 and PC3 cells (Panels C, D, G, H, K, L) compared to untreated controls (Panels A, B, E, F, I, J). DU145 and PC3 cells were stained with FAM-VAD-FMK-labeled fluoromethyl ketone to detect caspase activity. For each condition, DU145 cells (Panels A-D), PC3 cells (Panels E-H) and LNCaP cells (Panels I-L) were viewed by differential interference contrast (DIC) under visible light (Panels A, C, E, G, I, K) and by confocal microscopic analysis (Panels B, D, F, H, J, L) under laser excitation at 488 nm. Confocal microscopic analysis revealed no caspase staining in control DU145 (Panel B), PC3 cells (Panel F) and LNCaP (Panel J). Cells treated with PonA for 24 hours to induce DEFB1 (Panels C, D, G, H, K, L) revealed caspase activity in DU145 (Panel D) and PC3 (Panel H). No caspase activity was detected in LNCaP (Panel L).

Caspase activity was determined by confocal laser microscopic analysis (FIG. 5). DU145 and PC3 cell were induced for DEFB1 expression and activity was monitored based on the binding of green fluorescing FAM-VAD-FMK to caspases in cells actively undergoing apoptosis. Analysis of cells under DIC showed the presence of viable control DU145 (Panel A), PC3 (Panel E) and LNCaP (Panel I) cells at 0 hours. Excitation by the confocal laser at 488 nm produced no detectable green staining which indicates no caspase activity in DU145 (Panel B), PC3 (Panel F) or LNCaP (Panel J). Following induction for 24 hours, DU145 (Panel C), PC3 (Panel G) and LNCaP (Panel K) cells were again visible under DIC. Confocal analysis under fluorescence revealed green staining in DU145 (Panel D) and PC3 (Panel H) cell indicating caspase activity. However, there was no green staining in LNCaP (Panel L), indicating no induction of apoptosis by DEFB1.

In conclusion, this study provides the functional role of DEFB1 in prostate cancer. Furthermore, these findings show that DEFB1 is part of an innate immune system involved in tumor immunity. Data presented here demonstrate that DEFB1 expressed at physiological levels is cytotoxic to AR− hormone refractory prostate cancer cells, but not to AR+ hormone sensitive prostate cancer cell nor to normal prostate epithelial cells. Given that DEFB1 is constitutively expressed in normal prostate cells without cytotoxicity, it may be that late-stage AR− prostate cancer cells possess distinct phenotypic characteristics that render them sensitive to DEFB1 cytotoxicity. Thus, DEFB1 is a viable therapeutic agent for the treatment of late-stage prostate cancer, and potentially other cancers as well.

EXAMPLE 2 siRNA Mediated Knockdown of PAX2 Expression Results in Prostate Cancer Cell Death Independent of P53 Status This example examines the effects of inhibiting PAX2 expression by RNA interference in prostate cancer cells which differ in p53 gene status. The results demonstrate that the inhibition of PAX2 results in cell death irrespective of p53 status, indicating that there are additional tumor suppressor genes or cell death pathways inhibited by PAX2 in prostate cancer.

Materials and Methods siRNA Silencing of PAX2: In order to achieve efficient gene silencing, a pool of four complementary short interfering ribonucleotides (siRNAs) targeting human PAX2 mRNA (Accession No. NM_003989.1), were synthesized (Dharmacon Research, Lafayette, Colo., USA). A second pool of four siRNAs were used as an internal control to test for the specificity of PAX2 siRNAs. Two of the sequences synthesized target the GL2 luciferase mRNA (Accession No. X65324), and two were non-sequence-specific (Table 3). For annealing of siRNAs, 35 M of single strands were incubated in annealing buffer (100 mM potassium acetate, 30 mM HEPES-KOH at pH 7.4, 2 mM magnesium acetate) for 1 min at 90° C. followed by 1 hour incubation at 37° C.

TABLE 3

PAX2 siRNA Sequences. A pool of four siRNA was utilized to inhibit PAX2 protein expression.

| | Sense (5'-3') | |
|---|---|---|
| Sequence A | 5'-GAAGUCAAGUCGAGUCUAUUU-3' | SEQ ID NO: 38 |
| Sequence B | 5'-GAGGAAACGUGAUGAAGAUUU-3' | SEQ ID NO: 39 |
| Sequence C | 5'-GGACAAGAUUGCUGAAUACUU-3' | SEQ ID NO: 40 |
| Sequence D | 5'-CAUCAGAGCACAUCAAAUCUU-3' | SEQ ID NO: 41 |
| | Antisense (5'-3') | |
| Sequence A | 5'-AUAGACUCGACUUGACUUCUU-3' | SEQ ID NO: 3 |
| Sequence B | 5'-AUCUUCAUCACGUUUCCUCUU-3' | SEQ ID NO: 4 |

TABLE 3-continued

PAX2 siRNA Sequences. A pool of four siRNA was utilized to inhibit PAX2 protein expression.

| | | |
|---|---|---|
| Sequence C | 5'-GUAUUCAGCAAUCUUGUCCUU-3' | SEQ ID NO: 5 |
| Sequence D | 5'-GAUUUGAUGUGCUCUGAUGUU-3' | SEQ ID NO: 6 |

Western Analysis:

Briefly, cells were harvested by trypsinization and washed twice with PBS. Lysis buffer was prepared according to the manufacturer's instructions (Sigma), and was then added to the cells. Following a 15 minute incubation period at 4° C. on an orbital shaker, cell lysate were then collected and centrifuged for 10 minutes at 12000×g to pellet cellular debris. The protein-containing supernatant were then collected and quantitated. Next, 25 µg protein extract was loaded onto an 8-16% gradient SDS-PAGE (Novex). Following electrophoresis, proteins were transferred to PVDF membranes, and then blocked with 5% nonfat dry milk in TTBS (0.05% Tween 20 and 100 mM Tris-C1) for 1 hour. Blots were then probed with rabbit anti-PAX2 primary antibody (Zymed, San Francisco, Calif.) at a 1:2000 dilution. After washing, the membranes were incubated with anti-rabbit antibody conjugated to horseradish peroxidase (HRP) (dilution 1:5000; Sigma), and signal detection was visualized using chemilluminescence reagents (Pierce) on an Alpha Innotech Fluorchem 8900. As a control, blots were stripped and reprobed with mouse anti-β-actin primary antibody (1:5000; Sigma-Aldrich) and HRP-conjugated anti-mouse secondary antibody (1:5000; Sigma-Aldrich) and signal detection was again visualized.

Phase Contrast Microscopy: The effect of PAX2 knockdown on cell growth was analyzed by phase contrast microscopy. Here, 1-2×104 cells were seeded onto 6 well culture plates (BD Falcon, USA). The following day cells were treated with media only, negative control non-specific siRNA or PAX2 siRNA and allowed to incubate for six days. The cells were then viewed under an inverted Zeiss IM 35 microscope (Carl Zeiss, Germany) at 32× magnification. Phase contrast pictures of a field of cells were obtained using the SPOT Insight Mosaic 4.2 camera (Diagnostic Instruments, USA).

MTT Cytotoxicity Assay: DU145, PC3 and LNCaP cells (1×105) were transfected with 0.5 µg of the PAX2 siRNA pool or control siRNA pool using Codebreaker transfection reagent according to the manufacturer's protocol (Promega). Next, cell suspensions were diluted and seeded onto a 96-well plate at 1-5×103 cells per well and allowed to grow for 2-, 4- or 6 days. After culture, cell viability was determined by measuring the conversion of 3-[4,5-dimethylthiazol-2-yl]-2,5 diphenyl tetrazolium bromide, MTT (Promega), to a colored formazan product. Absorbance was read at 540 nm on a scanning multiwell spectrophotometer.

Pan-Caspase detection in the prostate cancer cell lines and quantitative real-time PCR were performed as described in Example 1. The primer pairs for BAX, BID and BAD were generated from the published sequences (Table 4). Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Gene expression was calculated as the relative expression ratio between the pro-apoptotic genes and GAPDH. All reactions were carried out in triplicate.

TABLE 4

Quantitative RT-PCR Primers. Nucleotide sequences of primers used to amplify PAX2 and GAPDH.

Sense (5'-3')

| | | |
|---|---|---|
| GAPDH | 5'-CCACCCATGGCAAATTCCATGGCA-3' | SEQ ID NO: 42 |
| BAD | 5'-CTCAGGCCTATGCAAAAAGAGGA-3' | SEQ ID NO: 43 |
| BID | 5'-AACCTACGCACCTACGTGAGGAG-3' | SEQ ID NO: 44 |
| BAX | 5'-GACACCTGAGCTGACCTTGG-3' | SEQ ID NO: 45 |

Antisense (5'-3')

Figure 6:
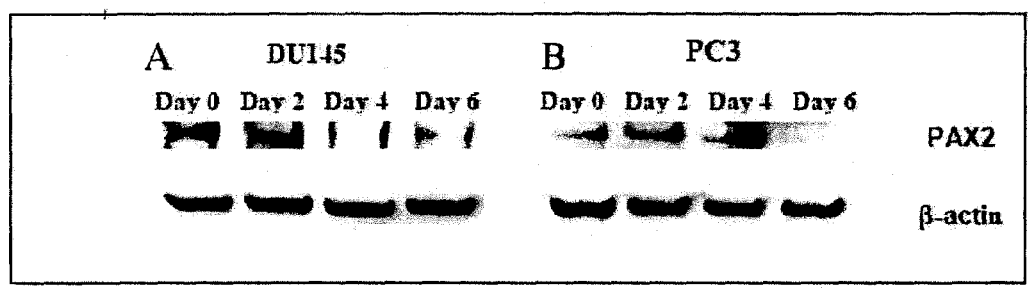
FIG. 6 shows silencing of paired box homeotic gene 2 (PAX2) protein expression following PAX2 siRNA Treatment. Panel A shows Western blot analysis of PC3 and DU145 cells transfected with PAX2 siRNA duplex at day zero (lane 1), day two (lane 2), and day four (lane 3). Panel B shows Western blot analysis of PC3 and DU145 cells transfected with PAX2 siRNA duplex at day zero (lane 1), day two (lane 2), day four (lane 3) and day 6 (lane 4). PAX2 protein was undetectable as early as after four days of treatment (lane 3) in DU145 cells and after six days of treatment in PC3. Blots were stripped and re-probed for β-actin as an internal control.

| | | |
|---|---|---|
| GAPDH | 5'-TCTAGACGGCAGGTCAGGTCAACC-3' | SEQ ID NO: 46 |
| BAD | 5'-GCCCTCCCTCCAAAGGAGAC-3' | SEQ ID NO: 47 |
| BID | 5'-CGTTCAGTCCATCCCATTTCTG-3' | SEQ ID NO: 48 |
| BAX | 5'-GAGGAAGTCCAGTGTCCAGC-3' | SEQ ID NO: 49 | siRNA Inhibition of PAX2 Protein: In order to confirm that the siRNA effective targeted the PAX2 mRNA, Western Analysis was performed to monitor PAX2 protein expression levels over a six day treatment period. Cells were given a single round of transfection with the pool of PAX2 siRNA. The results confirmed specific targeting of PAX2 mRNA by showing knock-down of PAX2 protein by day four in DU145 (FIG. 6 Panel A) and by day six in PC3 (FIG. 6 Panel B ).

Figure 7:
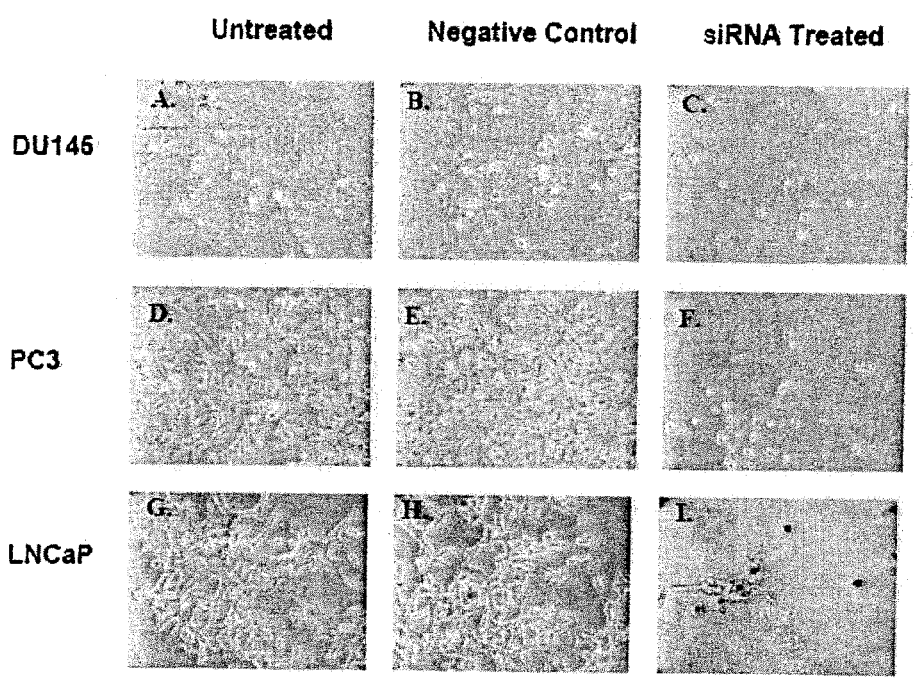
FIG. 7 shows analysis of prostate cancer cells growth after treatment with PAX2 siRNA. Panels A-L show contrast microscopic analysis of DU145, PC3 and LNCaP at 6 days in the presence of normal growth media. Treatment with negative control siRNA had no effect on the cells. However, there was a significant reduction in cell number in all three lines following treatment with PAX2 siRNA.

Knock-down of PAX2 inhibit Prostate Cancer Cell Growth: Cells were analyzed following a six day treatment period with media only, negative control non-specific siRNA or PAX2 siRNA (FIG. 7). DU145 (Panel A), PC3 (Panel D) and LNCaP (Panel G) cells all reached at least 90% confluency in the culture dishes containing media only. Treatment of DU145 (Panel B), PC3 (Panel E) and LNCaP (Panel H) with negative control non-specific siRNA had no effect on cell growth, and cells again reached confluency after six days. However, treatment with PAX2 siRNA resulted in a significant decrease in cell number. DU145 cells were approximately 15% confluent (Panel C) and PC3 cells were only 10% confluent (Panel F). LNCaP cell were 5% confluent following siRNA treatment (Panel I).

Figure 8:
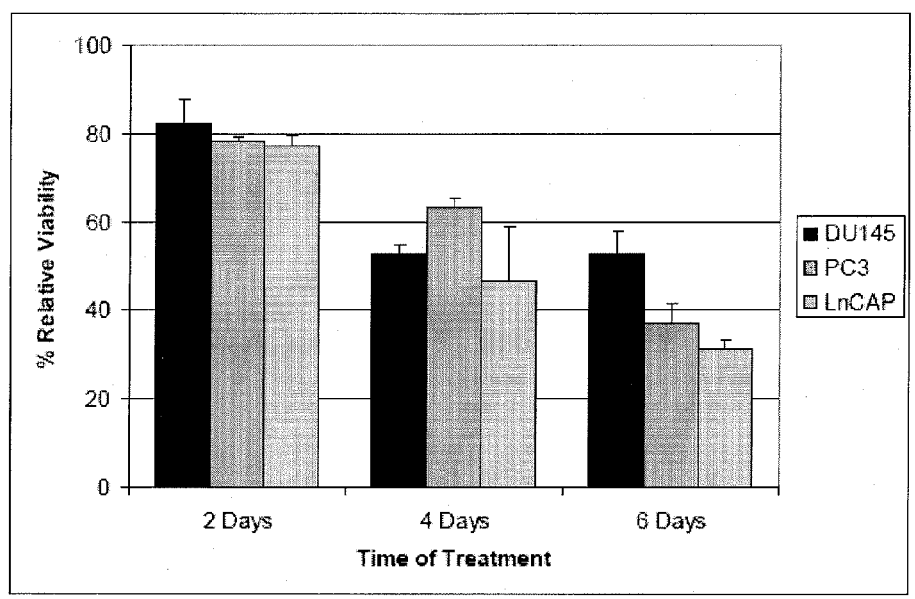
FIG. 8 shows analysis of cell death following siRNA silencing of PAX2. Prostate cancer cell lines PC3, DU145, and LNCaP were treated with 0.5 μg of a pool of four PAX2 siRNA's or four non-specific control siRNA's for 2, 4 or 6 days after which MTT assay was done to determine cell viability. Results represent mean±s.d., n=9.

Cytotoxicity Assays: Cell viability was measured after two-, four-, and six-day exposure times, and is expressed as a ratio of the 570-630 nm absorbance of treated cells divided by that of the untreated control cells (FIG. 8). Relative cell viability following 2 days of treatment was 77% in LNCaP, 82% in DU145 and 78% in PC3. After four days, relative cell viability was 46% in LNCaP, 53% in DU145 and 63% in PC3. After six days of treatment, relative cell viability decreased to 31% in LNCaP, 37% in PC3, and was 53% in DU145. As negative controls, cell viability was measured in after a six day treatment period with negative control non-specific siRNA or transfection reagent alone. For both conditions, there was no statistically significant change in cell viability compared to normal growth media.

Figure 9:
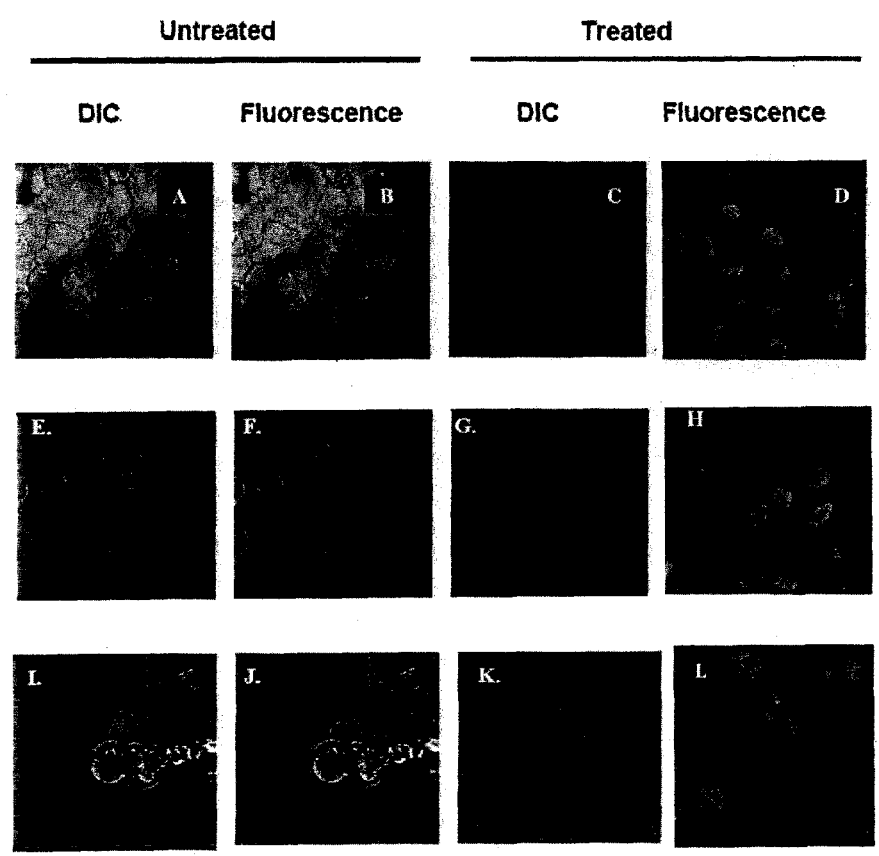
FIG. 9 shows analysis of caspase activity. DU145, PC3 and LNCaP cells were stained with carboxyfluorescein-labeled fluoromethyl ketone to detected caspase activity following treatment with PAX2 siRNA. Confocal microscopic analysis of untreated (Panels A, B, E, F, I, and J) and treated (Panels C, D, G, H, K, and L) cells show cells were visible with DIC. Analysis under fluorescence revealed no caspase staining in control DU145 (Panel B), PC3 cells (Panel F) and LNCaP cells (Panel J). However, cell treated with PAX2 siRNA induced caspase activity in DU145 (Panel D), PC3 (Panel H) and LNCaP (Panel L).

Pan-Caspase Detection: Caspase activity was detected by confocal laser microscopic analysis. DU145, PC3 and LNCaP cells were treated with PAX2 siRNA and activity was monitored based on the binding of FAM-labeled peptide to caspases in cells actively undergoing apoptosis which will be fluoresce green. Analysis of cells with media only under DIC shows the presence of viable DU145 (Panel A), PC3 (Panel E) and LNCaP (Panel I) cells at 0 hours (FIG. 9). Excitation by the confocal laser at 488 nm produced no detectable green staining which indicates no caspase activity in untreated DU145 (Panel B), PC3 (Panel F) or LNCaP (Panel J). Following four days of treatment with PAX2 siRNA, DU145 (Panel C), PC3 (Panel G) and LNCaP (Panel K) cells were again visible under DIC. Under fluorescence, the treated DU145 (Panel D), PC3 (Panel H) and LNCaP (Panel L) cells presented green staining indicating caspase activity.

Figure 10A:
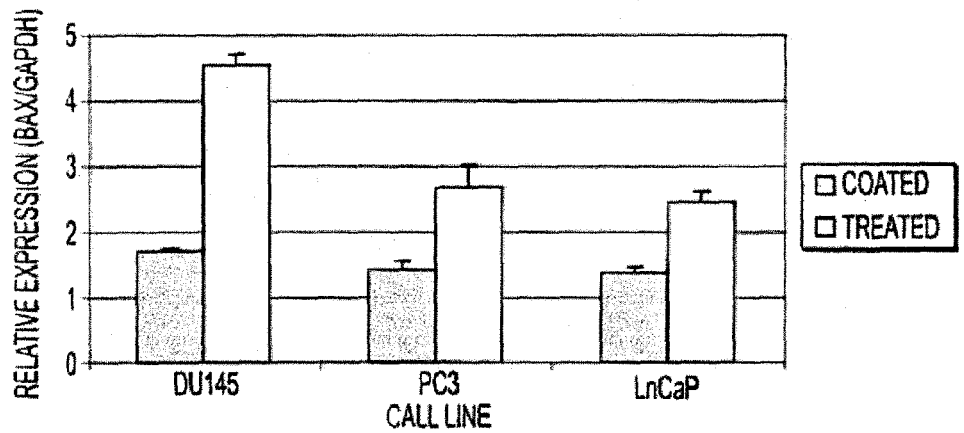
FIGS. 10A-10C show analysis of apoptotic factors following PAX2 siRNA treatment. Changes in expression of pro-apoptotic factors were compared in untreated control cells and in cells treated for six days with PAX2 siRNA.
Figure 10B:
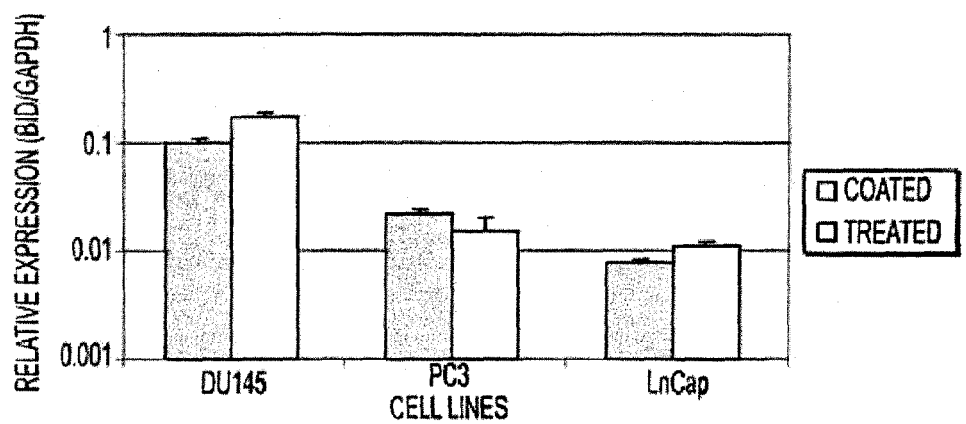
Figure 10C:
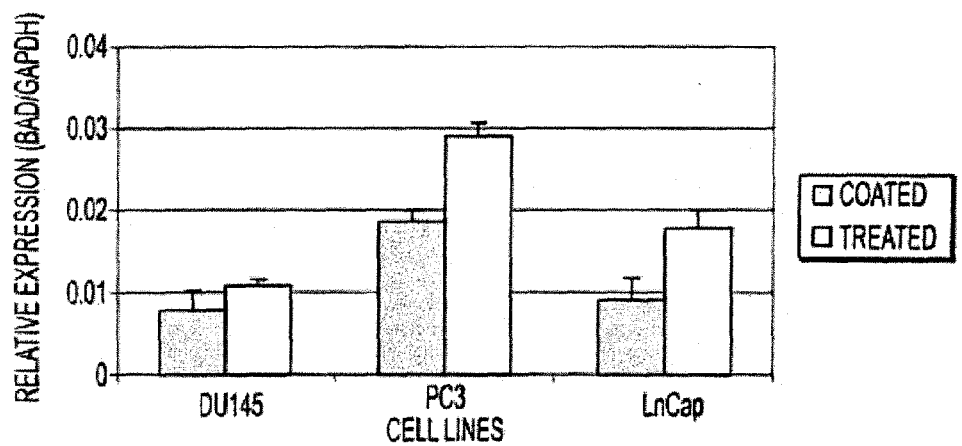
Figure 11:
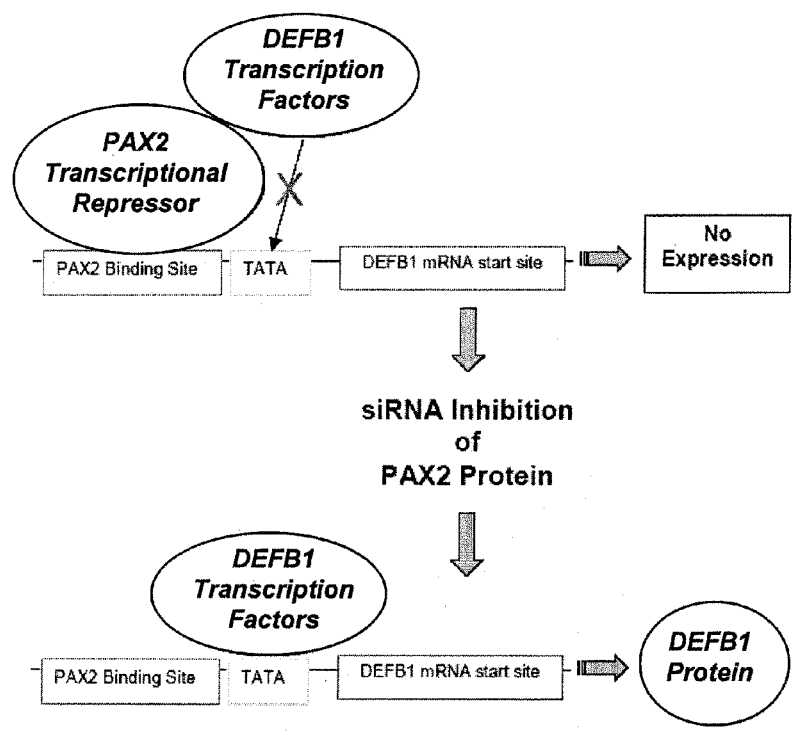
FIG. 11 shows model of PAX2 binding to DNA recognition sequence. The PAX2 transcriptional repressor binds to a CCTTG (SEQ ID NO: 1) recognition site immediately adjacent to the DEFB1 TATA box preventing transcription and DEFB1 protein expression. Inhibition of PAX2 protein expression allows normal DEFB1 expression.

Effect of PAX2 Inhibition on Pro-apoptotic Factors: DU145, PC3 and LNCaP cells were treated with siRNA against PAX2 for six days and expression of pro-apoptotic genes dependent and independent of p53 transcription regulation were measured to monitor cell death pathways. For BAX, there was a 1.81-fold increase in LNCaP, a 2.73-fold increase in DU145, and a 1.87-fold increase in PC3 (FIG. 10A). Expression levels of BID increased by 1.38-fold in LNCaP and 1.77-fold in DU145 (FIG. 10B). However, BID expression levels decreased by 1.44-fold in PC3 following treatment (FIG. 10C). Analysis of BAD revealed a 2.0-fold increase in expression in LNCaP, a 1.38-fold increase in DU145, and a 1.58-fold increase in PC3.

These results demonstrate dependency of prostate cancer cell survival on PAX2 expression. Following p53 activation as a result of PAX2 knock-down in the p53-expressing cell line LNCaP, the p53-mutated line DU145, and the p53-null line PC3, caspase activity was detected in all three lines, indicating of the initiation of programmed cell death. BAX expression was upregulated in all three cell lines independent of p53 status. The expression of pro-apoptotic factor BAD was also increased in all three lines following PAX2 inhibition. Following treatment with PAX2 siRNA, BID expression was increased in LNCaP and DU145, but actually decreased in PC3. These results indicate that cell death observed in prostate cancer is influenced by but is not dependent on p53 expression. The initiation of apoptosis in prostate cancer cells through different cell death pathways irrespective of p53 status indicates that PAX2 inhibits other tumor suppressors.

Besides SEQ ID NOS: 3-6, other examples of anti-PAX2 siRNAs include, but are not limited to, siRNAs having the sequences of (5' to 3' direction):

| | |
|---|---|
| ACCCGACTATGTTCGCCTGG, | (SEQ ID NO: 7) |
| AAGCTCTGGATCGAGTCTTTG, | (SEQ ID NO: 8) |
| ATGTGTCAGGCACACAGACG, | (SEQ ID NO: 9) |
| GUCGAGUCUAUCUGCAUCCUU, | (SEQ ID NO: 10) |
| GGAUGCAGAUAGACUCGACUU, | (SEQ ID NO: 11) |

PAX proteins are a family of transcription factors conserved during evolution and able to bind specific DNA sequences through a domains called a "paired domain (PD)" and a "homeodomain (HD)." The PD is a consensus sequence shared by certain PAX proteins (e.g., PAX2 and PAX6). The PD directs DNA binding of amino acids located in the α3-helix forming a DNA-Protein complex. For PAX2, the amino acids in the HD recognize and interact specifically with a CCTTG (SEQ ID NO:1) DNA core sequence. Oligonucleotides including this sequence or its complement are expected to be inhibitors of PAX 2 proteins.

In one embodiment, the oligonucleotide has the sequence of V-CCTTG-W (SEQ ID NO: 12), wherein V is from 1 to 35 contiguous flanking nucleotides of DEFB1 and W is from 1 to 35 nucleotides. The nucleotides can be contiguous nucleotides that normally flank the PAX2 DNA binding site of DEFB1. Alternatively, they can be unrelated to DEFB1, and selected routinely to avoid interference with the recognition sequence Other examples of oligonucleotides that inhibit PAX2 binding to the DEFB1 promoter include, but are not limited to, oligonucleotide having the sequences of (5' to 3' direction):

```
                                     (SEQ ID NO: 13)
CTCCCTTCAGTTCCGTCGAC (SEQ ID NO: 14)
CTCCCTTCACCTTGGTCGAC (SEQ ID NO: 15)
ACTGTGGCACCTCCCTTCAGTTCCGTCGACGAGGTTGTGC (SEQ ID NO: 16)
ACTGTGGCACCTCCCTTCACCTTGGTCGACGAGGTTGTGC
```

EXAMPLE 3

Inhibition of PAX2 Oncogene Results in DEFB1-Mediated Death of Prostate Cancer Cells The identification of tumor-specific molecules that serve as targets for the development of new cancer drugs is considered to be a major goal in cancer research. Example 1 demonstrated that there is a high frequency of DEFB1 expression loss in prostate cancer, and that induction of DEFB1 expression results in rapid apoptosis in androgen receptor negative-stage prostate cancer. These data show that DEFB1 plays a role in prostate tumor suppression. In addition, given that it is a naturally occurring component of the immune system of normal prostate epithelium, DEFB1 is expected to be a viable therapeutic agent with little to no side effects. Example 2 demonstrated that inhibition of PAX2 expression results in prostate cancer cell death independent of p53. These data indicate that there is an addition pro-apoptotic factor or tumor suppressor that is inhibited by PAX2. In addition, the data show that the oncogenic factor PAX2, which is over-expressed in prostate cancer, is a transcriptional repressor of DEFB1. The purpose of this study is to determine if DEFB1 loss of expression is due to aberrant expression of the PAX2 oncogene, and whether inhibiting PAX2 results in DEFB1-mediated cell death.

Materials and Methods

RNA Isolation and Quantitative RT-PCR were performed as described in Example 1. The primer pair for DEFB1 was generated from the published DEFB1 sequence (Accession No. U50930). Forty cycles of PCR were performed under standard conditions using an annealing temperature of 56° C. In addition, GAPDH was amplified as a housekeeping gene to normalize the initial content of total cDNA. DEFB1 expression was calculated as the relative expression ratio between DEFB1 and GAPDH and was compared in cells lines before and after siRNA knock-down of PAX2 expression. All reactions were run three times in triplicate.

Generation of the DEFB1 Reporter Construct: The pGL3 luciferase reporter plasmid was used to monitor DEFB1 reporter activity. Here, a region 160 bases upstream of the DEFB1 transcription initiation site and included the DEFB1 TATA box. The region also included the GTTCC (SEQ ID NO: 2) sequence which is necessary for PAX2 binding. The PCR primers were designed to contain Kpn1 and Nhe1 restriction sites. The DEFB1 promoter PCR products were restriction digested Kpn I and NheI and ligated into a similarly restriction digested pGL3 plasmid (FIG. 2). The constructs were transfected into E. coli and individual clones were selected and expanded. Plasmids were isolated and sequence integrity of the DEFB1/pGL3 construct was verified by automated sequencing.

Luciferase Reporter Assay: Here, 11 g of the DEFB1 reporter construct or the control pGL3 plasmid was transfected into $1 \times 10^6$ DU145 cells. Next, $0.5 \times 10^3$ cells were seeded onto each well of a 96-well plate and allowed to grow overnight. Then fresh medium was added containing PAX2 siRNA or media only and the cells were incubated for 48 hours. Luciferase was detected by the BrightGlo kit according to the manufacturer's protocol (Promega) and the plates were read on a Veritas automated 96-well luminometer. Promoter activity was expressed as relative luminescence.

Analysis of Membrane Permeability: Acridine orange (AO)/ethidium bromide (EtBr) dual staining was performed to identify changes in cell membrane integrity, as well as apoptotic cells by staining the condensed chromatin. AO stains viable cells as well as early apoptotic cells, whereas EtBr stains late stage apoptotic cells that have lost membrane permeability. Briefly, cells were seeded into 2 chamber culture slides (BD Falcon, USA). Cells transfected with empty pIND plasmid/pvgRXR or pIND DEFB1/pvgRXR were induced for 24 or 48 hour with media containing 10 μM Ponasterone A. Control cells were provided fresh media at 24 and 48 h. In order to determine the effect of PAX2 inhibition on membrane integrity, separate culture slides containing DU145, PC3 and LNCaP were treated with PAX2 siRNA and incubated for 4 days. Following this, cells were washed once with PBS and stained with 2 ml of a mixture (1:1) of AO (Sigma, USA) and EtBr (Promega, USA) (5 ug/ml) solution for 5 min. Following staining, the cells were again washed with PBS. Fluorescence was viewed by a Zeiss LSM 5 Pascal Vario 2 Laser Scanning Confocal Microscope (Carl Zeiss Jena, Germany). The excitation color wheel contain BS505-530 (green) and LP560 (red) filter blocks which allowed for the separation of emitted green light from AO into the green channel and red light from EtBr into the red channel. The laser power output and gain control settings within each individual experiment were identical between control and DEFB1 induced cells. The excitation was provided by a Kr/Ar mixed gas laser at wavelengths of 543 nm for AO and 488 nm for EtBr. Slides were analyzed under 40× magnification and digital images were stored as uncompressed TIFF files and exported into Photoshop CS software (Adobe Systems, San Jose, Calif.) for image processing and hard copy presentation.

Figure 13:
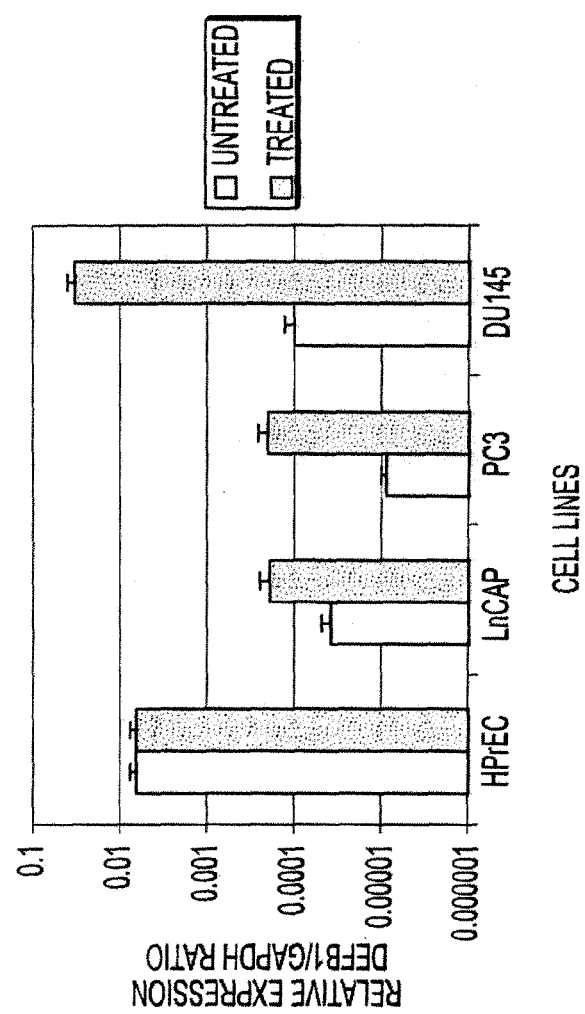
FIG. 13 shows inhibition of PAX2 results in DEFB1 Expression. DU145, PC3, LNCaP and HPrEC were treated for 48 hours with PAX2 siRNA. QRT-PCR analysis before treatment showed no DEFB1 expression in DU145, PC3 and LNCaP. However, DEFB1 expression was restored following treatment in all lines. There was no change in DEFB1 expression following siRNA treatment of PAX2-null HprEC.

ChIP Analysis of PAX2: Chromatin immunoprecipitation (ChIP) allows the identification of binding sites for DNA-binding proteins based upon in vivo occupancy of a promoter by a transcription factor and enrichment of transcription factor bound chromatin by immunoprecipitation. A modification of the protocol described by the Farnham laboratory was used; also on line at http://mcardle.oncology.wisc.edu/farnham/). The DU145 and PC3 cell lines over-expresses the PAX2 protein, but does not express DEFB1. Cells were incubated with PBS containing 1.0% formaldehyde for 10 minutes to crosslink proteins to DNA. Samples were then sonicated to yield DNA with an average length of 600 bp. Sonicated chromatin precleared with Protein A Dynabeads was incubated with PAX2-specific antibody or "no antibody" control [isotype-matched control antibodies]. Washed immunoprecipitates were then collected. After reversal of the crosslinks, DNA was analyzed by PCR using promoter-specific primers to determine whether DEFB1 is represented in the PAX2-immunoprecipitated samples. Primers were designed to amplify the 160 bp region immediately upstream of the DEFB1 mRNA start site which contained the DEFB1 TATA box and the functional GTTCC (SEQ ID NO: 2) PAX2 recognition site. For these studies, positive controls included PCR of an aliquot of the input chromatin (prior to immunoprecipitation, but crosslinks reversed). All steps were performed in the presence of protease inhibitors.

siRNA Inhibition of PAX2 Increases DEFB1 Expression: QRT-PCR analysis of DEFB1 expression before siRNA treatment revealed relative expression levels of 0.00097 in DU145, 0.00001 in PC3, and 0.00004 LNCaP (FIG. 13). Following siRNA knock-down of PAX2, relative expression was 0.03294 (338-fold increase) in DU145, 0.00020 (22.2-fold increase) in PC3 and 0.00019 (4.92-fold increase) in LNCaP. As a negative control, the human prostate epithelial cell line (hPrEC) which is PAX2 null, revealed expression levels at 0.00687 before treatment and 0.00661 following siRNA treatment confirming no statistical change in DEFB1 expression.

Figure 14:
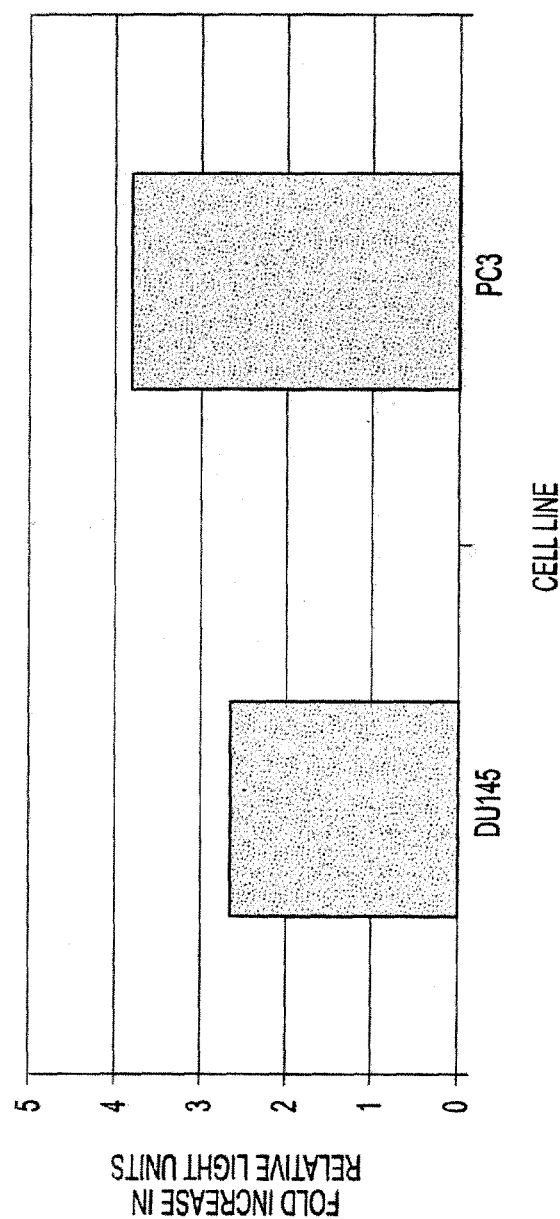
FIG. 14 shows inhibition of PAX2 results in increased DEFB1 promoter activity. PC3 promoter/pGL3 and DU145 promoter/pGL3 construct were generated and were transfected into PC3 and DU145 cells, respectively. Promoter activity was compared before and after PAX2 inhibition by siRNA treatment. DEFB1 promoter activity increased 2.65-fold in DU145 and 3.78 fold in PC3 following treatment.

DEFB1 Causes Cell Membrane Permeability: Membrane integrity was monitored by confocal analysis (FIG. 14). Here, intact cells stain green due to AO which is membrane permeable. In addition, cells with compromised plasma membranes would stain red by EtBr which is membrane impermeable. Here, uninduced DU145 (A) and PC3 (D) cells stained positively with AO and emitted green color, but did not stain with EtBr. However, DEFB1 induction in both DU145 (B) and PC3 (E) resulted in the accumulation of EtBr in the cytoplasm at 24 hours indicated by the red staining. By 48 hours, DU145 (C) and PC3 (F) possessed condensed nuclei and appeared yellow, which was due to the presence of both green and red staining resulting from the accumulation of AO and EtBr, respectively.

Inhibition of PAX2 Results in Membrane Permeability: Cells were treated with PAX2 siRNA for 4 days and membrane integrity was monitored again by confocal analysis. Here, both DU145 and PC3 possessed condensed nuclei and appeared yellow. However, LNCaP cells' cytoplasm and nuclei remained green following siRNA treatment. Also red staining at the cell periphery indicates the maintenance of cell membrane integrity. These findings indicate that the inhibition of PAX2 results in specifically DEFB1-mediated cell death in DU1145 and PC3, but not LNCaP cells. Death observed in LNCaP is due to the transactivation of the existing wild-type p53 in LNCaP following PAX2 inhibition.

siRNA Inhibition of PAX2 Increases DEFB1 Promoter Activity: Analysis of DEFB1 promoter activity in DU145 cells containing the DEFB1/pGL3 construct revealed a 2.65 fold increase in relative light units following 48 hours of treatment compared to untreated cells. In PC3 cells, there was a 3.78-fold increase in relative light units compared to untreated cells.

PAX2 Binds to the DEFB1 Promoter: ChIP analysis was performed on DU145 and PC3 cells to determine if the PAX2 transcriptional repressor is bound to the DEFB1 promoter. In FIG. 15A, lane 1 contains a 100 bp molecular weight marker. Lane 2 is a positive control representing 160 bp region of the DEFB1 promoter amplified from DU145 before cross-linking and immunoprecipitation. Lane 3 is a negative control representing PCR performed without DNA. Lanes 4 and 5 are negative controls representing PCR from immunoprecipitations performed with IgG from cross-linked DU145 and PC3, respectively. FIG. 15B shows PCR amplification of 25 pg of DNA (lane 6 and 8) and 50 pg of DNA (lane 7 and 9) immunoprecipitated with anti-PAX2 antibody after crosslinking show 160 bp promoter fragment in DU145 and PC3, respectively.

Figure 12:
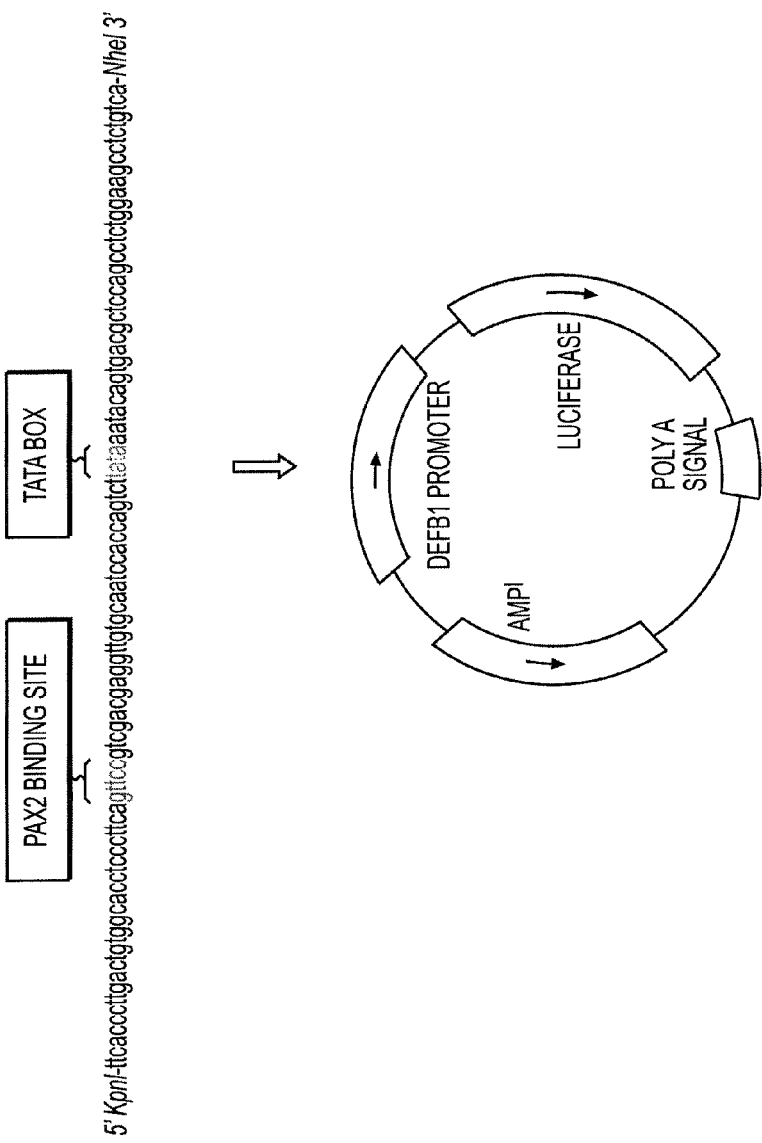
FIG. 12 illustrates the DEFB1 reporter construct. The DEFB1 promoter consisting of the first 160 bases upstream of the mRNA start site was PCR amplified from DU145 cell and ligated into the pGL3 luciferase reporter plasmid.

These results demonstrate that the oncogenic factor PAX2 suppresses DEFB1 expression. The suppression occurs at the transcriptional level. Furthermore, computational analysis of the DEFB1 promoter revealed the presence of a GTTCC (SEQ ID NO: 2) DNA binding site for the PAX2 transcriptional repressor next to the DEFB1 TATA box (FIG. 12). One of the hallmarks of defensin cytotoxicity is the disruption of membrane integrity. These results show that ectopic expression of DEFB1 in prostate cancer cells results in a loss of membrane potential due to compromised cell membranes. The same phenomenon is observed after inhibiting PAX2 protein expression. Therefore, suppression of PAX2 expression or function, results in the re-establishment of DEFB1 expression and subsequently DEFB1-mediated cell death. Also, the present results establish the utility of DEFB1 as a directed therapy for prostate cancer treatment, and potentially other cancer treatments, through innate immunity.

EXAMPLE 4

Effect of DEFB1 Expression in Implanted Tumor Cells

The anti-tumoral ability of DEFB1 is evaluated by injecting tumor cells that overexpress DEFB1 into nude mice. DEFB1 is cloned into pBI-EGFP vector, which has a bidirectional tetracycline responsible promoter. Tet-Off Cell lines are generated by transfecting pTet-Off into DU145, PC3 and LNCaP cells and selecting with G418. The pBI-EGFP-DEFB1 plasmid is co-transfected with pTK-Hyg into the Tet-off cell lines and selected with hygromycin. Only single-cell suspensions with a viability of >90% are used. Each animal receives approximately 500,000 cells administered subcutaneously into the right flank of female nude mice. There are two groups, a control group injected with vector only clones and a group injected with the DEFB1 over-expressing clones. 35 mice are in each group as determined by a statistician. Animals are weighed twice weekly, tumor growth monitored by calipers and tumor volumes determined using the following formula: volume=0.5×(width)2×length. All animals are sacrificed by CO2 overdose when tumor size reaches 2 mm3 or 6 months following implantation; tumors are excised, weighed and stored in neutral buffered formalin for pathological examination. Differences in tumor growth between the groups are descriptively characterized through summary statistics and graphical displays. Statistical significance is evaluated with either the t-test or non-parametric equivalent.

EXAMPLE 5

Effect of PAX2 siRNA on Implanted Tumor Cells

Hairpin PAX2 siRNA template oligonucleotides utilized in the in vitro studies are utilized to examine the effect of the up-regulation of DEFB1 expression in vivo. The sense and antisense strand (see Table 4) are annealed and cloned into pSilencer 2.1 U6 hygro siRNA expression vector (Ambion) under the control of the human U6 RNA pol III promoter. The cloned plasmid is sequenced, verified and transfected into PC3, Du145, and LNCap cell lines. Scrambled shRNA is cloned and used as a negative control in this study. Hygromycin resistant colonies are selected, cells are introduced into the mice subcutaneously and tumor growth is monitored as described above.

EXAMPLE 6

Effect of Small Molecule Inhibitors of PAX2 Binding on Implanted Tumor Cells The DNA recognition sequence for PAX2 binding resides in the DEFB1 promoter between nucleotides −75 and −71 [+1 refers to the transcriptional start site]. Short oligonucleotides complementary to the PAX2 DNA-binding domain are provided. Examples of such oligonucleotides include the 20-mer and 40-mer oligonucleotides containing the GTTCC (SEQ ID NO: 2) recognition sequence provided below. These lengths were randomly selected, and other lengths are expected to be effective as blockers of binding. As a negative control, oligonucleotides with a scrambled sequence (CTCTG)—(SEQ ID NO: 17) were designed to verify specificity. The oligonucleotides are transfected into the prostate cancer cells and the HPrEC cells with lipofectamine reagent or Codebreaker transfection reagent (Promega, Inc). In order to confirm DNA-protein interactions, double stranded oligonucleotides will be labeled with [$^{32}$P] dCTP and electrophoretic mobility shift assays are performed. In addition, DEFB1 expression is monitored by QRT-PCR and Western analysis following treatment with oligonucleotides. Finally, cell death is detected by MTT assay and flow cytometry as previously described.

```
Recognition Sequence #1:
                                      (SEQ ID NO: 13)
CTCCCTTCAGTTCCGTCGAC Recognition Sequence #2:
                                      (SEQ ID NO: 14)
CTCCCTTCACCTTGGTCGAC Scramble Sequence #1:
                                      (SEQ ID NO: 18)
CTCCCTTCACTCTGGTCGAC Recognition Sequence #3:
                                      (SEQ ID NO: 15)
ACTGTGGCACCTCCCTTCAGTTCCGTCGACGAGGTTGTGC Recognition Sequence #4:
                                      (SEQ ID NO: 16)
ACTGTGGCACCTCCCTTCACCTTGGTCGACGAGGTTGTGC Scramble Sequence #2:
                                      (SEQ ID NO: 19)
ACTGTGGCACCTCCCTTCACTCTGGTCGACGAGGTTGTGC
```

Further examples of oligonucleotides of the invention include:

```
Recognition Sequence #1:
                                      (SEQ ID NO: 20)
5'-AGAAGTTCACCCTTGACTGT-3'

Recognition Sequence #2:
                                      (SEQ ID NO: 21)
5'-AGAAGTTCACGTTCCACTGT-3'

Scramble Sequence #1:
                                      (SEQ ID NO: 22)
5'-AGAAGTTCACGCTCTACTGT-3'

Recognition Sequence #3:
                                      (SEQ ID NO: 23)
5'-TTAGCGATTAGAAGTTCACCCTTGACTGTGGCACCTCCC-3'

Recognition Sequence #4:
                                      (SEQ ID NO: 24)
5'-GTTAGCGATTAGAAGTTCACGTTCCACTGTGGCACCTCCC-3'

Scramble Sequence #2:
                                      (SEQ ID NO: 25)
5'-GTTAGCGATTAGAAGTTCACGCTCTACTGTGGCACCTCCC-3'
```

This set of alternative inhibitory oligonucleotides represents the recognition sequence (along with the CCTTG (SEQ ID NO: 1) core sequence) for the PAX2 binding domain and homeobox. These include actual sequences from the DEFB1 promoter.

The PAX2 gene is required for the growth and survival of various cancer cells including prostate. In addition, the inhibition of PAX2 expression results in cell death mediated by the innate immunity component DEFB1. Suppression of DEFB1 expression and activity is accomplished by binding of the PAX2 protein to a GTTCC (SEQ ID NO: 2) recognition site in the DEFB1 promoter. Therefore, this pathway provides a viable therapeutic target for the treatment of prostate cancer. In this method, the sequences bind to the PAX2 DNA binding site and block PAX2 binding to the DEFB1 promoter thus allowing DEFB1 expression and activity. The oligonucleotide sequences and experiment described above are examples of and demonstrate a model for the design of additional PAX2 inhibitor drugs.

Given that the GTTCC (SEQ ID NO: 2) sequence exists in interleukin-3, interleukin-4, the insulin receptor and others, PAX2 regulates their expression and activity as well. Therefore the PAX2 inhibitors disclosed herein have utility in a number of other diseases including those directed related to inflammation including prostatitis and benign prostatic hypertrophy (BPH).

EXAMPLE 7

Loss of DEFB1 Expression Results in Increased Tumorigenesis

Generation of Loss of Function Mice:

The Cre/loxP system has been useful in elucidating the molecular mechanisms underlying prostate carcinogenesis. Here a DEFB1 Cre conditional KO is used for inducible disruption within the prostate. The DEFB1 Cre conditional KO involves the generation of a targeting vector containing loxP sites flanking DEFB1 coding exons, targeted ES cells with this vector and the generation of germline chimeric mice from these targeted ES cells. Heterozygotes are mated to prostate-specific Cre transgenics and heterozygous intercross is used to generate prostate-specific DEFB1 KO mice. Four genotoxic chemical compounds have been found to induce prostate carcinomas in rodents: N-methyl-N-nitrosourea (MNU), N-nitrosobis 2-oxopropyl. amine (BOP), 3,2X-dimethyl-4-amino-biphenyl (MAB) and 2-amino-1-methyl-6-phenylimidazow 4,5-bxpyridine (PhIP). DEFB1-transgenic mice are treated with these carcinogenic compounds via intra-gastric administration or i.v. injection for prostate adenoma and adenocarcinoma induction studies. Prostate samples are studied for differences in tumor growth and changes gene expression though histological, immunohistological, mRNA and protein analyses.

Generation of GOF mice: For PAX2 inducible GOF mice, PAX2 GOF (bi-transgenic) and wild-type (mono-transgenic) littermates are administered doxycycline (Dox) from 5 weeks of age to induce prostate-specific PAX2 expression. Briefly, PROBASIN-rtTA mono-transgenic mice (prostate cell-specific expression of tet-dependent rtTA inducer) are crossed to our PAX2 transgenic responder lines. For induction, bi-transgenic mice are fed Dox via the drinking water (500 mg/L freshly prepared twice a week). Initial experiments verify low background levels, good inducibility and cell-type specific expression of PAX2 and the EGFP reporter using transgenic founder line in bi-transgenic mice. Regarding experimental group sizes, 5-7 age- and sex-matched individuals in each group (wild-type and GOF) allow for statistical significance. For all animals in this study, prostate tissues are collected initially at weekly intervals for analysis and comparison, to determine carcinogenic time parameters.

PCR Genotyping, RT-PCR and qPCR: PROBASIN-rtTA transgenic mice are genotyped using the following PCR primers and conditions:

```
PROBASIN5 (forward)
                            (SEQ ID NO: 26)
5'-ACTGCCCATTGCCCAAACAC-3';

RTTA3 (reverse)
                            (SEQ ID NO: 27)
5'-AAAATCTTGCCAGCTTTCCCC-3';
```

95° C. denaturation for 5 min, followed by 30 cycles of 95° C. for 30 see, 57° C. for 30 sec, 72° C. for 30 sec, followed by a 5 min extension at 72° C., yielding a 600 bp product.

PAX2 inducible transgenic mice are genotyped using the following PCR primers and conditions:

```
PAX2For
                            (SEQ ID NO: 28)
5'-GTCGGTTACGGAGCGGACCGGAG-3';

Rev5'IRES
                            (SEQ ID NO: 29)
5'-TAACATATAGACAAACGCACACCG-3';
```

95° C. denaturation for 5 min, followed by 34 cycles of 95° C. for 30 sec, 63° C. for 30 sec, 72° C. for 30 sec, followed by a 5 min extension at 72° C., yielding a 460 bp product.

Immortomouse hemizygotes are be genotyped using the following PCR primers and conditions:

```
Immol1,
                            (SEQ ID NO: 30)
5'-GCGCTTGTGTC GCCATTGTATTC-3';

Immol2,
                            (SEQ ID NO: 31)
5'-GTCACACCACAGAAGTAAGGTTCC-3';
```

94° C. 30 sec, 58° C. 1 min, 72° C. 1 min 30 sec, 30 cycles to yield a ~1 kb transgene band. For genotyping PAX2 knockout mice, the following PCR primers and conditions are used:

```
PAX2For
                            (SEQ ID NO: 32)
5'-GTCGGTTACGGAGCGGACCGGAG-3';

PAX2Rev
                            (SEQ ID NO: 33)
5'-CACAGAGCATTGGCGATCTCGATGC-3';
```

94° C. 1 min, 65° C. 1 min, 72° C. 30 sec, 36 cycles to yield a 280 bp band.

DEFB1 Peptide Animal Studies:

Six-week-old male athymic (nude) mice purchased from Charles River Laboratories are injected sub-cutaneously over the scapula with $10^6$ viable PC3 cells. One week after injection, the animals are randomly allocated to one of three groups-group I: control; group II: intraperitoneal injections of DEFB1,100 μg/day, 5 days a week, for weeks 2-14; group III: intraperitoneal injections of DEFB1, 100 mg/day, 5 days a week, for weeks 8-14. Animals are maintained in sterile housing, four animals to a cage, and observed on a daily basis. At 10-day intervals, the tumors are measured by using calipers, and the volumes of the tumors are calculated by using $V=(L \times W2)/2$.

EXAMPLE 8

Targeting PAX2 Expression for the Chemoprevention of Intraepithelial Neoplasia and Cancer Cancer chemoprevention is defined as the prevention of cancer or treatment at the pre-cancer state or even earlier. The long period of progression to invasive cancer is a major scientific opportunity but also an economic obstacle to showing the clinical benefit of candidate chemopreventive drugs. Therefore, an important component of chemopreventive agent development research in recent years has been to identify earlier (than cancer) end points or biomarkers that accurately predict an agent's clinical benefit or cancer incidence-reducing effect. In many cancers, IEN is an early end point such as in prostate cancer. Given that the PAX2/DEFB1 pathway is deregulated during IEN and perhaps at even an earlier histopathological state makes it a powerful predictive biomarker and an excellent target for chemoprevention of cancer. Shown are a number of compounds that suppress PAX2 and increases DEFB1 expression that may have utility as chemoprevention agents for prostate cancer.

As shown in Table 1, the PAX2 gene is expressed in a number of cancers. In addition, several cancers have been shown to have aberrant PAX2 expression (FIG. 18). Chemoprevention via target PAX2 expression may have a significant impact on cancer related deaths. Angiotensin II (AngII) is a major regulator of blood pressure and cardiovascular homeostasis and is recognized as a potent mitogen. AngII mediates its biological effects through binding to two subtypes of receptors, Angiotensin Type I receptor (AT1R) and Angiotensin Type II receptor (AT2R) which belong to the superfamily of G-protein-coupled receptors but have different tissue distribution and intracellular signaling pathways. In addition to its effects on blood pressure, AngII has been shown to play a role in various pathological situations involving tissue remodeling, such as wound healing, cardiac hypertrophy and development. In fact, recent studies have revealed local expression of several components of the Renin-Angiotensin System (RAS) in various cancer cells and tissues including the prostate. Upregulation of AT1R provides a considerable advantage to cancer cells that have learn to evade apoptosis and growth regulatory elements.

Materials and Methods

Reagents and Treatments: Cells were treated with 5 or 10 uM of AngII, 5 uM of the ATR1 antagonist Los, 5 uM of the ATR2 antagonist PD123319, 25 uM of the MEK inhibitor U0126, 20 uM of the MEK/ERK inhibitor PD98059 or 250 μM of the AMP kinase inducer AICAR.

Western Analysis was performed as described in Example 2. Blots were then probed with primary antibody (anti-PAX2, -phospho-PAX2, -JNK, -phospho-JNK, -ERK1/2, or -phospho-ERK1/2) (Zymed, San Francisco, Calif.) at 1:1000-2000 dilutions. After washing, the membranes were incubated with anti-rabbit antibody conjugated to horseradish peroxidase (HRP) (dilution 1:5000; Sigma), and signal detection was visualized using chemilluminescence reagents (Pierce) on an Alpha Innotech Fluorchem 8900. As a control, blots were stripped and re-probed with mouse anti-β-actin primary antibody (1:5000; Sigma-Aldrich) and HRP-conjugated anti-mouse secondary antibody (1:5000; Sigma-Aldrich), and signal detection was again visualized.

QRT-PCR Analysis was performed as described in Example 1. Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Relative expression was calculated as the ratio between each genes and GAPDH. All reactions were carried out in triplicate.

Thymidine Incorporation:

Proliferation of cells was determined by [$^3$H]thymidine ribotide ([$^3$H] TdR) incorporation into DNA. $0.5 \times 10^6$ cells/well of suspension DU145 cells were plated in their appropriate media. Cells were incubated for 72 hrs with or without the presence of AngII at the indicated concentrations. Cells were exposed to 37 kBq/ml [methyl-$^3$H]thymidine in the same medium for 6 hours. The adherent cells were fixed by 5% trichloroacetic acid and lysed in SDS/NaOH lysis buffer overnight. Radioactivity was measured by Beckman LS3801 liquid scintillation counter (Canada). Suspension cell culture was harvested by cell harvester (Packard instrument Co., Meriden, Conn.), and radioactivity was measured by 1450 microbeta liquid scintillation counter (PerkinElmer Life Sciences).

To investigate the effect of AngII on PAX2 expression in DU145 prostate cancer cells, PAX2 expression was examined following treatment with AngII over a 30 min to 48 hour period. As shown in FIG. 19, PAX2 expression progressively increased over time following AngII treatment. Blocking RAS signaling by treating DU145 with Los significantly reduced PAX2 expression (FIG. 20A). Here, PAX2 expression was 37% after 48 hours and was 50% after 72 hours of Los treatment compared to untreated control DU145 cells (FIG. 21). It is known that the AT2R receptor oppose the action of the AT1R. Therefore, the effect of blocking the AT2R receptor on PAX2 expression was examined. Treatment of DU145 with the AT2R blocker PD123319 resulted in a 7-fold increase in PAX2 expression after 48 hours and an 8-fold increase after 96 hours of treatment (FIG. 20B). Collectively, these findings demonstrate that PAX2 expression is regulated by the ATR1 receptor.

It is known that AngII directly affects the proliferation of prostate cancer cells through AT1R-mediated activation of MAPK and STAT3 phosphorylation. Treatment of DU145 with AngII resulted in a two- to three-fold increase in proliferation rate (FIG. 21). However, treatment with Los decreased proliferated rates by 50%. In addition, blocking the AT1R receptor by pre-treating with Los for 30 min suppressed the effect of AngII on proliferation.

To further examine the role of the AT1R signaling in the regulation of PAX2 expression and activation, the effect of blocking various components of the MAP kinase signaling pathway on PAX2 expression was examined. Here, DU145 cells treated with the MEK inhibitor U0126 resulted in a significant reduction of PAX2 expression (FIG. 22). Furthermore, treatment with MEK/ERK inhibitor PD98059 also resulted in decreased PAX2. Treatment of DU145 cells with Los had no effect on ERK protein levels, but reduced the amount of phospho-ERK (FIG. 23A). However, treatment of DU145 with Los resulted in a significant reduction of PAX2 expression. Similar results were observed with U0126 and PD98059. It is also known that PAX2 expression is regulated by STAT3 which is a down-stream target of ERK. Treatment of DU145 with Los, U0126, and PD98059 reduced phospho-STAT3 protein levels (FIG. 23C). These results demonstrate that PAX2 is regulated via AT1R in prostate cancer cells.

In addition, the effect of AT1R signaling on PAX2 activation by JNK was examined. Treatment of DU145 with Los, U0126, and PD98059 all resulted in a significant decrease or suppression of phospho-PAX2 protein levels (FIG. 24A). However, Los and U0126 did not decrease phospho-JNK protein levels (FIG. 24B). Therefore, the decrease in phospho-PAX2 appears to be due to decreased PAX2 levels, but not decreased phosphorylation.

5-Aminoimidazole-4-carboxamide-1-β-4-ribofuranoside (AICAR) is widely used as an AMP-kinase activator, which regulates energy homeostasis and response to metabolic stress. Recent reports have indicated anti-proliferative and pro-apoptotic action of activated AMPK using pharmacological agents or AMPK overexpression. AMPK activation has been shown to induce apoptosis in human gastric cancer cells, lung cancer cells, prostate cancer, pancreatic cells, and hepatic carcinoma cells and enhance oxidative stress induced apoptosis in mouse neuroblastoma cells, by various mechanisms that include inhibition of fatty acid synthase pathway and induction of stress kinases and caspase 3. In addition, treatment of PC3 prostate cancer cells increased expression of p21, p27, and p53 proteins and inhibition of PI3K-Akt pathway. All of these pathways are directly or indirectly regulated by PAX2. Treatment of prostate cancer cells with AICAR resulted in the suppression of PAX2 expression (FIG. 23B) as well as its activated form phosphor-PAX2 (FIG. 24A). In addition, phospho-STAT3 which regulated PAX2 expression was also suppressed (FIG. 23C).

Finally, it was hypothesized that aberrant RAS signaling which leads to upregulation and overexpression of PAX2 suppresses the expression of the DEFB1 tumor suppressor gene. To investigate this, the normal prostate epithelial primary culture hPrEC was treated with AngII and examined both PAX2 and DEFB1 expression levels. An inverse relationship between DEFB1 and PAX2 expression was discovered in normal prostate cells versus prostate cancer cells. Untreated hPrEC exhibited 10% relative PAX2 expression compared to expression in PC3 prostate cancer cells. Conversely, untreated PAX2 exhibited only 2% relative DEFB1 expression compared to expression in hPrEC. Following 72 hours of treatment with 10 uM of AngII, there was a 35% decrease in DEFB1 expression compared to untreated hPrEC, and by 96 hours there was a 50% decrease in DEFB1 expression compared to untreated hPrEC cells. However, there was 66% increase in PAX2 expression at 72 hours, and by 96 hours there was a 79% increase in PAX2 expression compared to untreated hPrEC cells. Furthermore, the increase in PAX2 expression in hPrEC after 72 hours was 77% of PAX2 levels observed in PC3 prostate cancer cells. After 96 hours of AngII treatment PAX2 expression was 89% of PAX2 expression in PC3. These results demonstrate that deregulated RAS signaling suppresses DEFB1 expression via the upregulation of PAX2 expression in prostate cells.

Inhibition of apoptosis is a critical pathophysiological factor that contributes to the development of cancer. Despite significant advances in cancer therapeutics, little progress has been made in the treatment of advanced disease. Given that carcinogenesis is a multiyear, multistep, multipath disease of progression, chemoprevention through the use of drug or other agents to inhibit, delay, or reverse this process has been recognized as a very promising area of cancer research. Successful drug treatment for the chemoprevention of prostate cancer requires the use of therapeutics with specific effects on target cells while maintaining minimal clinical effects on the host with the overall goal of suppressing cancer development. Therefore, understanding the mechanisms in early stage carcinogenesis is critical in determining the efficacy of a specific treatment. The significance of aberrant PAX2 expression and its abrogation of apoptosis, with subsequent contribution to tumor formation, suggest that it may be a suitable target for prostate cancer treatment. PAX2 was regulated by the AT1R in prostate cancer (FIG. 26). In this, deregulated RAS signaling resulted in increased PAX2 oncogene expression, and a decrease in the expression of DEFB1 tumor suppressor. Therefore, the use of AT1R antagonists decreases PAX2 expression and results in increased prostate cancer cell death via re-expression of DEFB1 (FIG. 27). These results offer a novel finding that targeting PAX2 expression via the Renin-Angiotensin signaling pathway, the AMP Kinase pathway, or other methods involving the inactivation of the PAX2 protein (i.e. anti-PAX2 antibody vaccination) may be a viable target for cancer prevention (Table 5).

TABLE 5

Compounds Utilized to Inhibit PAX2 Expression for Chemoprevention

|  | NAME | Drug Class |
|---|---|---|
| Drug 1 | Losartan | Angiotensin Type 1 Receptor blocker |
| Drug 2 | PD123319 | Angiotensin Type 2 Receptor blocker |
| Drug 3 | U0126 | MEK inhibitor |
| Drug 4 | PD98059 | MEK/ERK inhibitor |
| Drug 5 | AICAR | AMP kinase inducer |
|  | Target | Drug Function |
| Drug A | Anti-PAX2 Antibody | PAX2 Vaccine |
| Drug B | Angiotensinogen | Renin-AngII pathway inhibitor |
| Drug C | Angiotensin Converting Enzyme | Renin-AngII pathway inhibitor |

This study demonstrates that the upregulation of the PAX2 oncogene in prostate cancer is due to deregulated RAS signaling. PAX2 expression is regulated by the ERK 1/2 signaling pathway which is mediated by the Angiotensin type I receptor. In addition, blocking the AT1R with Losartan (Los) suppresses PAX2 expression. In addition, AICAR which is an AMPK activator has also shown promise as a potential PAX2 inhibitor. Collectively, these studies strongly implicate these classes of drugs as potential suppressors of PAX2 expression and may ultimately serve as novels chemoprevention agents.

EXAMPLE 9

PAX2-DEFB1 Expression Level as a Grading Tool for Prostate Tissue and Predictor of Prostate Cancer Development Materials and Methods
QRT-PCR Analysis:
Prostate sections were collected from patients that underwent radical prostatectomies. Following pathological examination, laser capture microdisection was performed to isolate areas of Normal, Proliferative Intraepithelial Neoplasia (PIN) and Cancerous tissue. QRT-PCR was performed as previously described to assess expression. DEFB1 and PAX2 expression in each region and GAPDH was used as an internal control.

Blood collection and RNA isolation: For QRT-PCR, blood (2.5 ml) from each individual was collected into a PAXgene™ Blood RNA tube (QIAGEN) following the manufacturer's protocol. Whole blood was thoroughly mixed with PAXgene stabilization reagent and stored at room temperature for 6 hours prior to RNA extraction. Total RNA was then extracted using the PAXgene™ Blood RNA kit according to the manufacturer's directions (QIAGEN). In order to remove contaminating genomic DNA, total RNA samples absorbed to the PAXgene™ Blood RNA System spin column was incubated with DNase I (QIAGEN) at 25° C. for 20 min to remove genomic DNA. Total RNA was eluted, quantitated, and QRT-PCR is performed as previously mentioned to compare PAX2 and DEFB1 expression ratios.

QRT-PCR analysis of LCM normal tissue demonstrated that patients with relative DEFB1 expression levels greater than 0.005 have a lower Gleason Score compared to those with expression levels lower than 0.005 (FIG. 28A). Thus, there is an inverse relationship between DEFB1 expression and Gleason score. Conversely, there was a positive correlation between PAX2 expression and Gleason score in malignant prostate tissue and PIN (FIG. 28B).

The PAX2 and DEFB1 expression levels in normal, PIN and cancerous tissues from separate patients were calculated and compared (FIGS. 29A and 29B). Overall, PAX2 expression levels relative to GAPDH internal control ranged between 0 and 0.2 in normal (benign) tissue, 0.2 and 0.3 in PIN, and between 0.3 and 0.5 in cancerous (malignant) tissue (FIG. 30). For DEFB1 there was an inverse relationship compared to PAX2. Here, DEFB1 expression levels relative to GAPDH internal control ranged between 0.06 and 0.005 in normal (benign) tissue, 0.005 and 0.003 in PIN, and between 0.003 and 0.001 in cancerous (malignant) tissue. Therefore, disclosed is a predictive scale (designated as the "Donald predictive factor" or "DPF") which utilizes the PAX2-DEFB1 expression ratio as a prognosticator of benign, precancerous (PIN) and malignant prostate tissue. Tissues with PAX2-DEFB1 ratios between 0 and 39 based on the DPF will represent normal (pathologically benign). Tissue with a PAX2-DEFB1 ratio between 40 and 99 will represent PIN (pre-cancerous) based on the DPF scale. Finally, tissue with a PAX2-DEFB1 ratio between 100 and 500 will be malignant (low to high grade cancer).

There currently is a critical need for predictive biomarkers for prostate cancer development. It is known that the onset of prostate cancer occurs long before the disease is detectable by current screening methods such as the PSA test or the digital rectal exam. It is thought that a reliable test which could monitor the progression and early onset of prostate cancer would greatly reduce the mortality rate through more effective disease management. Disclosed herein is a predictive index to allow physicians to know well in advance the pathological state of the prostate. The DPF measures the decrease in the PAX2-DEFB1 expression ratio associated with prostate disease progression. This powerful measure can not only predict the likelihood of a patient developing prostate cancer, but also may pinpoint the early onset of pre-malignant cancer. Ultimately, this tool can allow physicians to segregate which patients have more aggressive disease from those which do not.

The identification of cancer-specific markers has been utilized to help identify circulating tumor cells (CTCs). There is also emerging evidence which demonstrates that detection of tumor cells disseminated in peripheral blood can provide clinically important data for tumor staging, prognostication, and identification of surrogate markers for early assessment of the effectiveness of adjuvant therapy. Furthermore, by comparing gene expression profiling of all circulating cells, one can examine the expression of the DEFB1 and PAX2 genes which play a role in "immunosurveillance" and "cancer survival", respectively as a prognosticator for the early detection of prostate cancer.

EXAMPLE 10

Functional Analysis of the Host Defense Peptide Human Beta Defensin-1: New Insight into its Potential Role in Cancer Materials and Methods Tissue Samples and Laser Capture Microdissection:

Prostate tissues were obtained from patients who provided informed consent prior to undergoing radical prostatectomy. Samples were acquired through the Hollings Cancer Center tumor bank in accordance with an Institutional Review Board-approved protocol. This included guidelines for the processing, sectioning, histological characterization, RNA purification and PCR amplification of samples. Prostate specimens received from the surgeons and pathologists were immediately frozen in OCT compound. Each OCT block was cut to produce serial sections which were stained and examined. Areas containing benign cells, prostatic intraepithelial neoplasia (PIN), and cancer were identified and used to guide our selection of regions from unstained slides using the Arcturus PixCell II System (Sunnyvale, Calif.). Caps containing captured material were exposed to 20 μl of lysate from the Arcturus Pico Pure RNA Isolation Kit and processed immediately. RNA quantity and quality was evaluated using sets of primers that produce 5' amplicons. The sets include those for the ribosomal protein L32 (the 3' amplicon and the 5' amplicon are 298 bases apart), for the glucose phosphate isomerase (391 bases apart), and for the glucose phosphate isomerase (842 bases apart). Ratios of 0.95 to 0.80 were routinely obtained for these primer sets using samples from a variety of prepared tissues. Additional tumor and normal samples were grossly dissected by pathologists, snap frozen in liquid nitrogen and evaluated for hBD-1 and cMYC expression.

Cloning of hBD-1 Gene:

hBD-1 cDNA was generated from RNA by reverse transcription-PCR using primers generated from the published hBD-1 sequence (accession no. U50930) (Ganz, 2004). The PCR primers were designed to contain ClaI and KpnI restriction sites. hBD-1 PCR products were restriction digested with ClaI and KpnI and ligated into a TA cloning vector. The TA/hBD1 vector was then transfected into the XL-1 Blue strain of E. coli by heat shock and individual clones were selected and expanded. Plasmids were isolated by Cell Culture DNA Midiprep (Qiagen, Valencia, Calif.) and sequence integrity verified by automated sequencing. The hBD-1 gene fragment was then ligated into the pTRE2 digested with ClaI and KpnI, which served as an intermediate vector for orientation purposes. The pTRE2/hBD-1 construct was digested with ApaI and KpnI to excise the hBD-1 insert. The insert was ligated into pIND vector of the Ecdysone Inducible Expression System (Invitrogen, Carlsbad, Calif.) also double digested with ApaI and KpnI. The construct was transfected into E. coli and individual clones were selected and expanded. Plasmids were isolated and sequence integrity of pIND/hBD-1 was again verified by automated sequencing.

Transfection:

Cells ($1\times10^6$) were seeded onto 100-mm Petri dishes and grown overnight. Next, the cells were co-transfected using Lipofectamine 2000 (Invitrogen) with 1 μg of pvgRXR plasmid, which expresses the heterodimeric ecdysone receptor, and 1 μg of the pIND/hBD-1 vector construct or pIND/j-galactosidase (β-gal) control vector in Opti-MEM media (Life Technologies, Inc.). Transfection efficiency was determined by inducing β-gal expression with Ponasterone A (PonA) and staining cells with a β-galactosidase detection kit (Invitrogen). Assessment of transfection efficiency by counting positive staining (blue) colonies which demonstrated that 60-85% of cells expressed β-galactosidase for the cell lines.

Immunocytochemistry:

In order to verify hBD-1 protein expression, DU145 and hPrEC cells were seeded onto 2-chamber culture slides (BD Falcon, USA) at $1.5-2\times104$ cells per chamber. DU145 cells transfected with pvgRXR alone (control) or with the hBD-1 plasmid were induced for 18 hours with media containing 10 μM Pon A, while untransfected cells received fresh growth media. Following induction, cells were washed in 1×PBS and fixed for 1 hour at room temperature with 4% paraformaldehyde. Cells were then washed six times with 1×PBS and blocked in 1×PBS supplemented with 2% BSA, 0.8% normal goat serum (Vector Laboratories, Inc., Burlingame, Calif.) and 0.4% Triton-X 100 for 1 hour at room temperature. Next, cells were incubated overnight in primary rabbit anti-human BD-1 polyclonal antibody (PeproTech Inc., Rocky Hill, N.J.) diluted 1:1000 in blocking solution. Following this, cells were washed six times with blocking solution and incubated for 1 hour at room temperature in Alexa Fluor 488 goat anti-rabbit IgG (H+L) secondary antibody at a dilution of 1:1000 in blocking solution. After washing cells with blocking solution six times, coverslips were mounted with Gel Mount (Biomeda, Foster City, Calif.). Finally, cells were viewed under differential interference contrast (DIC) and under laser excitation at 488 nm. The fluorescent signal was analyzed by confocal microscopy (Zeiss LSM 5 Pascal) using a 63×DIC oil lens with a Vario 2 RGB Laser Scanning Module. The digital images were exported into Photoshop CS Software (Adobe Systems) for image processing and hard copy presentation.

RNA isolation and quantitative RT-PCR were performed as described in Example 1. The primer pairs for hBD-1 and c-MYC were generated from the published sequences (Table 6). Forty cycles of PCR were performed under standard conditions using an annealing temperature of 56.4° C. for hBD-1 and c-MYC and 55° C. for PAX2. In addition, β-actin (Table 6) was amplified as a housekeeping gene to normalize the initial content of total cDNA. Gene expression in benign prostate tissue samples was calculated as the expression ratio compared to β-actin. Levels of hBD-1 expression in malignant prostate tissue, hPREC prostate primary culture, and prostate cancer cell lines before and after induction were calculated relative to the average level of hBD-1 expression in hPrEC cells. As a negative control, QRT-PCR reactions without cDNA template were also performed. All reactions were run a minimum of three times.

MTT cell viability assay was performed as described in Example 1.

Analysis of membrane integrity was performed as described in Example 3. Cells transfected with empty plasmid or hBD-1 plasmid were induced for 24 or 48 hours with media containing 10 μM Pon A, while control cells received fresh growth media at each time point.

TABLE 6

Sequences of QRT-PCR primers

| | Sense (5'-3') | Antisense (5'-3') |
|---|---|---|
| β-Actin | CCTGGCACCCAGCACAAT (SEQ ID NO: 34) | GCCGATCCACACGGAGTACT (SEQ ID NO: 36) |
| hBD-1 | TCAGCAGTGGAGGGCAATG (SEQ ID NO: 50) | CCTCTGTAACAGGTGCCTTGAT (SEQ ID NO: 51) |
| cMYC | ACAGCAAACCTCCTCACAGCC (SEQ ID NO: 52) | TGGAGACGTGGCACCTCTTG (SEQ ID NO: 53) |

Nucleotide sequences of primers used to amplify hBD-1, cMyc, PAX2, and β-actin.

Flow cytometry and Caspase detection were performed as described in Example 1.

siRNA silencing of PAX2 was performed as described in Example 2. SiRNA molecules were coated with CodeBreaker transfection reagent (Promega, Inc.) according to manufacturer's directions prior to treatment.

Statistical Analysis:

Statistical analysis was performed by using the Student's t-test for unpaired values. P values were determined by a two-sided calculation, and a P value of less than 0.05 was considered statistically significant. Statistical differences are indicated by asterisks.

hBD-1 Expression in Prostate Tissue:

82% of prostate cancer frozen tissue sections analyzed exhibited little or no expression of hBD-1 (Donald et al., 2003). To compare hBD-1 expression levels, QRTPCR analysis was performed on normal prostate tissue obtained by gross dissection or LCM of normal prostate tissue adjacent to malignant regions which were randomly chosen. Here, hBD-1 was detected in all of the gross dissected normal clinical samples with a range of expression that represents approximately a 6.6-fold difference in expression levels (FIG. 31A). LCM captured normal tissue samples expressed hBD-1 at levels in a range that represents a 32-fold difference in expression (FIG. 31B). Matching sample numbers to corresponding patient profiles revealed that in most cases, the hBD-1 expression level was higher in patient samples with a Gleason score of 6 than in patient samples with a Gleason score of 7. In addition, a comparison of hBD-1 expression levels in tissue obtained by gross dissection and LCM from the same patient, #1343, demonstrated an 854-fold difference in expression between the two isolation techniques. Therefore, these results indicate that LCM provides a more sensitive technique to assess hBD-1 expression in prostate tissue.

hBD-1 Expression in Prostate Cell Lines:

To verify upregulation of hBD-1 in the prostate cancer cell lines after transfection with the hBD-1 expression system, QRTPCR was performed. In addition, no template negative controls were also performed, and amplification products were verified by gel electrophoresis. Here, hBD-1 expression was significantly lower in the prostate cancer cell lines compared to hPrEC cells. Following a 24 hours induction period, relative expression levels of hBD-1 significantly increased in DU145, PC3 and LNCaP as compared to the cell lines prior to hBD-1 induction (FIG. 32A).

Next, protein expression of hBD-1 in was verified DU145 cells transfected with the hBD-1 expression system after induction with Pon A by immunocytochemistry. As a positive control, hBD-1 expressing hPrEC prostate epithelial cells were also examined. Cells were stained with primary antibody against hBD-1 and protein expression was monitored based on the green fluorescence of the secondary antibody (FIG. 32B). Analysis of cells under DIC verify the presence of hPrEC cells and DU145 cells induced for hBD-1 expression at 18 hours. Excitation by the confocal laser at 488 nm produced revealed green fluorescence indicating the presence of hBD-1 protein in hPrEC as a positive control. However, there was no detectable green fluorescence in control DU145 cells and empty plasmid induced DU145 cells demonstrating no hBD-1 expression. Confocal analysis of DU145 cells induced for hBD-1 expression revealed green fluorescence indicating the presence of hBD-1 protein following induction with Pon A.

Expression of hBD-1 Results in Decreased Cell Viability:

MTT assay was performed to assess the effect of hBD-1 expression on relative cell viability in DU145, PC3, PC3/AR+ and LNCaP prostate cancer cell lines. MTT analysis with empty vector exhibited no statistical significant change in cell viability. Twenty-four hours following hBD-1 induction, relative cell viability was 72% in DU145 and 56% in PC3 cells, and after 48 hours cell viability was reduced to 49% in DU145 and 37% in PC3 cells (FIG. 33A). Following 72 hours of hBD-1 induction, relative cell viability decreased further to 44% in DU145 and 29% PC3 cells. Conversely, there was no significant effect on the viability of LNCaP cells. In order to assess whether the resistance to hBD-1 cytotoxicity observed in LNCaP was due to the presence of the androgen receptor (AR), the hBD-1 cytotoxicity in PC3 cells was examined with ectopic AR expression (PC3/AR+). Here, there was no difference between PC3/AR+ and PC3 cells. Therefore, the data indicates that that hBD-1 is cytotoxic specifically to late-stage prostate cancer cells.

In order to determine whether the effects of hBD-1 on PC3 and DU145 were cytostatic or cytotoxic, FACS analysis was performed to measure cell death. Under normal growth conditions, more than 90% of PC3 and DU145 cultures were viable and non-apoptotic (lower left quadrant) and did not stain with annexin V or PI (FIG. 4). After inducing hBD-1 expression in PC3 cells, the number of cells undergoing early apoptosis and late apoptosis/necrosis (lower and upper right quadrants, respectively) totaled 10% at 12 hours, 20% at 24 hours, and 44% at 48 hours. For DU145 cells, the number of cells undergoing early apoptosis and late apoptosis/necrosis totaled 12% after 12 hours, 34% at 24 hours, and 59% after 48 hours of induction. No increase in apoptosis was observed in cells containing empty plasmid following induction with Pon A. Annexin V and propidium iodide uptake studies have demonstrated that hBD-1 has cytotoxic activity against DU145 and PC3 prostate cancer cells and results indicate apoptosis as a mechanism of cell death.

hBD-1 causes alterations in membrane integrity and caspase activation: It was investigated whether the cell death observed in prostate cancer cells after hBD-1 induction is caspase-mediated apoptosis. To better understand the cellular mechanisms involved in hBD-1 expression, confocal laser microscopic analysis was performed (FIG. 5) on DU145 and LNCaP cells induced for hBD-1 expression. Pan-caspase activation was monitored based on the binding and cleavage of green fluorescing FAM-VAD-FMK to caspases in cells actively undergoing apoptosis. Analysis of cells under DIC showed the presence of viable control DU145 (FIG. 5A) and LNCaP (FIG. 5E) cells at 0h. Excitation by the confocal laser at 488 nm produced no detectable green staining which indicates no caspase activity in DU145 (FIG. 5B) or LNCaP (FIG. 5F) control cells. Following induction for 24 hours, DU145 (FIG. 5C) and LNCaP (FIG. 5G) cells were again visible under DIC. Confocal analysis under fluorescence revealed green staining in DU145 (FIG. 5D) cells indicating pan-caspase activity after the induction of hBD-1 expression. However, there was no green staining in LNCaP (FIG. 5H) cells induced for hBD-1 expression. Therefore, cell death observed following induction of hBD-1 is caspase-mediated apoptosis.

The proposed mechanism of antimicrobial activity of defensin peptides is the disruption of the microbial membrane due to pore formation (Papo and Shai, 2005). In order to determine if hBD-1 expression altered membrane integrity EtBr uptake was examined by confocal analysis. Intact cells were stained green due to AO which is membrane permeable, while only cells with compromised plasma membranes stained red due to incorporation of membrane impermeable EtBr. Control DU145 and PC3 cells stained positively with AO and emitted green color, but did not stain with EtBr. However, hBD-1 induction in both DU145 and PC3 resulted in the accumulation of EtBr in the cytoplasm at 24 as indicated by the red staining. By 48 hours, DU145 and PC3 possessed condensed nuclei and appeared yellow due to the colocalization of green and red staining from AO and EtBr, respectively. Conversely, there were no observable alterations to membrane integrity in LNCaP cells after 48 hours of induction as indicated by positive green fluorescence with AO, but lack of red EtBr fluorescence. This finding indicates that alterations to membrane integrity and permeablization in response to hBD-1 expression differ between early- and late-stage prostate cancer cells.

Comparison of hBD-1 and cMYC Expression Levels:

QRT-PCR analysis was performed on LCM prostate tissue sections from three patients (FIG. 34). In patient #1457, hBD-1 expression exhibited a 2.7-fold decrease from normal to PIN, a 3.5-fold decrease from PIN to tumor and a 9.3-fold decrease from normal to tumor (FIG. 34A). Likewise, cMYC expression followed a similar expression pattern in patient #1457 where expression decreased by 1.7-fold from normal to PIN, 1.7-fold from PIN to tumor and 2.8-fold from normal to tumor (FIG. 34B). In addition, there was a statistically significant decrease in cMYC expression in the other two patients. Patient #1569 had a 2.3-fold decrease from normal to PIN, while in patient #1586 there was a 1.8-fold decrease from normal to PIN, a 4.3-fold decrease from PIN to tumor and a 7.9-fold decrease from normal to tumor.

Induction of hBD-1 Expression Following PAX2 Inhibition:

To further examine the role of PAX2 in regulating hBD-1 expression, siRNA was utilized to knockdown PAX2 expression and QRT-PCR performed to monitor hBD-1 expression. Treatment of hPrEC cells with PAX2 siRNA exhibited no effect on hBD-1 expression (FIG. 35). However, PAX2 knockdown resulted in a 42-fold increase in LNCaP, a 37-fold increase in PC3 and a 1026-fold increase in DU145 expression of hBD-1 compared to untreated cells. As a negative control, cells were treated with non-specific siRNA which had no significant effect on hBD-1 expression.

EXAMPLE 11

Inhibition of PAX2 Expression Results in Alternate Cell Death Pathways in Prostate Cancer Cells Differing in P53 Status Materials and Methods Cell Lines:

The cancer cell lines PC3, DU145 and LNCaP, which all differ in p53 mutational status (Table 7) were cultured as described in Example 1.

siRNA silencing of PAX2 and Western analysis were performed as described in Example 2. Blots were then probed with rabbit anti-PAX2 primary antibody (Zymed, San Francisco, Calif.) at a 1:1000 dilution. After washing, the membranes were incubated with anti-rabbit antibody conjugated to horseradish peroxidase (HRP) (dilution 1:5000; Sigma), and signal detection was visualized using chemiluminescence reagents (Pierce) on an Alpha Innotech Fluorchem 8900. As a control, blots were stripped and reprobed with mouse anti-β-actin primary antibody (1:5000; Sigma-Aldrich) and HRP-conjugated anti-mouse secondary antibody (1:5000; Sigma-Aldrich), and signal detection was again visualized.

TABLE 7 p53 gene mutation in prostate cancer cell lines

| Cell line | Nucleotide change | Amino acid change | Gene status | Reference |
|---|---|---|---|---|
| DU145 | CCT-CTT | Pro-Leu | Gain/loss-of-function | Tepper et al. 2005; Bodhoven et al. 2003 |
| | GTT-TTT | Val-Phe | | |
| PC3 | Deleted a C, GCC-GC | Frame-shift | No activity | Isaacs et al. 1991 |
| LNCaP | No deletion, wild-type | — | Normal function | Carroll et al. 1993 |

Phase contrast microscopy and MTT cytotoxicity assay were performed as described in Example 2.

Pan-caspase detection and Quantitative real-time RT-PCR were performed as described in Example 1. The primer pairs for BAX, BID, BCL-2, AKT and BAD were generated from the published sequences (Table 8). Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Relative expression was calculated as the ratio between each genes and GAPDH. All reactions were carried out in triplicate.

TABLE 8

Quantitative RT-PCR primers

| | Sense (5'-3') | Antisense (5'-3') |
|---|---|---|
| GAPDH | CCACCCATGGCAAATTCCAT GGCA (SEQ ID NO: 42) | TCTAGACGGCAGGTCAGGTC AACC (SEQ ID NO: 46) |
| BAD | CTCAGGCCTATGCAAAAAGA GGA (SEQ ID NO: 43) | GCCCTCCCTCCAAAGGAGAC (SEQ ID NO: 47) |

TABLE 8-continued

Quantitative RT-PCR primers

| | Sense (5'-3') | Antisense (5'-3') |
|---|---|---|
| BID | AACCTACGCACCTACGTGAG GAG (SEQ ID NO: 44) | CGTTCAGTCCATCCCATTTC TG (SEQ ID NO: 48) |
| BAX | GACACCTGAGCTGACCTTGG (SEQ ID NO: 45) | GAGGAAGTCCAGTGTCCAGC (SEQ ID NO: 49) |
| BCL-2 | TATGATACCCGGGAGATCGT GATC (SEQ ID NO: 54) | GTGCAGATGCCGGTTCAGGTA CTC (SEQ ID NO: 55) |
| AKT | TCAGCCCTGGACTACCTGCA (SEQ ID NO: 56) | GAGGTCCCGGTACACCACGT (SEQ ID NO: 57) |

Membrane permeability assay was performed as described in Example 3. PC3 and LNCaP cells were transfected with PAX2 siRNA, non-specific siRNA or media only.

Analysis of PAX2 Protein Expression in Prostate Cells:

PAX2 protein expression was examined by Western analysis in HPrEC prostate primary culture and in LNCaP, DU145 and PC3 prostate cancer cell lines. Here, PAX2 protein was detected in all of the prostate cancer cell lines (FIG. 36A). However, no PAX2 protein was detectable in HPrEC. Blots were stripped and re-probed for β-actin as internal control to ensure equal loading. PAX2 protein expression was also monitored after selective targeting and inhibition by PAX2 specific siRNA in DU145, PC3 and LNCaP prostate cancer cell lines. Cells were given a single round of transfection with the pool of PAX2 siRNA over a 6-day treatment period. PAX2 protein was expressed in control cells treated with media only. Specific targeting of PAX2 mRNA was confirmed by observing knockdown of PAX2 protein in all three cell lines (FIG. 36B).

Effect of PAX2 Knockdown on Prostate Cancer Cell Growth:

The effect of PAX2 siRNA on cell number and cell viability was analyzed using light microscopy and MTT analysis. To examine the effect of PAX2 siRNA on cell number, PC3, DU145 and LNCaP cell lines were transfected with media only, non-specific siRNA or PAX2 siRNA over a period of 6 days. Each of the cell lines reached a confluency of 80-90% in 60 mm culture dishes containing media only. Treatment of HPrEC, DU145, PC3 and LNCaP cells with non-specific siRNA appeared to have little to no effect on cell growth compared to cell treated with media only (FIGS. 38A, 38C and 38E, respectively). Treatment of the PAX2-null cell line HPrEC with PAX2 siRNA appeared to have no significant effect on cell growth (FIG. 37B). However, treatment of the prostate cancer cell lines DU145, PC3 and LNCaP with PAX2 siRNA resulted in a significant decrease in cell number (FIGS. 38D, 38F and 38H, respectively).

Effect of PAX2 Knockdown on Prostate Cancer Cell Viability:

Cell viability was measured after 2-, 4-, and 6-day exposure times. Percent viability was calculated as the ratio of the 570-630 nm absorbance of cell treated with PAX2 siRNA divided by untreated control cells. As negative controls, cell viability was measured after each treatment period with negative control non-specific siRNA or transfection with reagent alone. Relative cell viability was calculated by dividing percent viability following PAX2 siRNA treatment by percent viability following treatment with non-specific shRNA (FIG. 38). After 2 days of treatment, relative viability was 116% in DU145, 81% in PC3 and 98% in LNCaP. After 4 days of treatment, relative cell viability decreased to 69% in DU145, 79% in PC3, and 80% in LNCaP. Finally, by 6 days relative viability was 63% in DU145, 43% in PC3 and 44% in LNCaP. In addition, cell viability was also measured following treatment with transfection reagent alone. Here, each cell line exhibited no significant decrease in cell viability.

Detection of Pan-Caspase Activity:

Caspase activity was detected by confocal laser microscopic analysis. LNCaP, DU145 and PC3 cells were treated with PAX2 siRNA and activity was monitored based on the binding of FAM-labeled peptide to caspases in cells actively undergoing apoptosis which will be fluoresce green. Analysis of cells with media only shows the presence of viable LNCaP, DU145 and PC3 cells, respectively. Excitation by the confocal laser at 488 nm produced no detectable green staining which indicates no caspase activity in the untreated cells (FIGS. 39A, 39C and 39E, respectively). Following 4 days of treatment with PAX2 siRNA, LNCaP, DU145 and PC3 cells under fluorescence presented green staining indicating caspase activity (FIGS. 39B, 39D and 39F, respectively).

Effect of PAX2 Inhibition on Apoptotic Factors:

LNCaP, DU145 and PC3 cells were treated with siRNA against PAX2 for 4 days and expression of both pro- and anti-apoptotic factors were measured by QRTPCR. Following PAX2 knockdown, analysis of BAD revealed a 2-fold in LNCaP, 1.58-fold in DU145 and 1.375 in PC3 (FIG. 40A). Expression levels of BID increased by 1.38-fold in LNCaP and a 1.78-fold increase in DU145, but there was no statistically significant difference in BID observed in PC3 after suppressing PAX2 expression (FIG. 40B). Analysis of the anti-apoptotic factor AKT revealed a 1.25-fold decrease in expression in LNCaP and a 1.28-fold decrease in DU145 following treatment, but no change was observed in PC3 (FIG. 40C).

Analysis of Membrane Integrity and Necrosis:

Membrane integrity was monitored by confocal analysis in LNCaP, DU145 and PC3 cells. Here, intact cells stained green due to AO which is membrane permeable, while cells with compromised plasma membranes would stained red due to incorporation of membrane impermeable EtBr into the cytoplasm, and yellow due to co-localization of AO and EtBr in the nuclei. Untreated LNCaP, DU145 and PC3 cells stained positively with AO and emitted green color, but did not stain with EtBr. Following PAX2 knockdown, there were no observable alterations to membrane integrity in LNCaP cells as indicated by positive green fluorescence with AO and absence of red EtBr fluorescence. These finding further indicate that LNCaP cells can be undergoing apoptotic, but not necrotic cell death following PAX2 knockdown. Conversely, PAX2 knockdown in DU145 and PC3 resulted in the accumulation of EtBr in the cytoplasm as indicated by the red staining. In addition, both DU145 and PC3 possessed condensed nuclei which appeared yellow due to the co-localization of green and red staining from AO and EtBr, respectively. These results indicate that DU145 and PC3 are undergoing an alternate cell death pathway involving necrotic cell death compared to LNCaP.

EXAMPLE 12

PAX2 and DEFB-1 Expression in Breast Cancer Cell Lines And Mammary Tissues with Ductal or Lobular Intraepithelial Neoplasia PAX2 and DEFB-1 expression will be determined in breast biopsy samples of ductal or lobular intraepithelial neoplasia, and in the following breast cancer cell lines: BT-20: Isolated from a primary invasive ductal carcinoma; cell express E-cadherin, ER, EGFR and uPA.

BT-474: Isolated from a primary invasive ductal carcinoma; cell express E-cadherin, ER, PR, and have amplified HER2/neu.

Hs578T: Isolated from a primary invasive ductal carcinoma; a cell line was also established from normal adjacent tissue, termed Hs578Bst.

MCF-7: Established from a pleural effusion. The cells express ER and are the most common example of estrogen-responsive breast cancer cells.

MDA-MB-231: Established from a pleural effusion. The cells are ER-negative, E-cadherin negative and highly invasive in in vitro assays.

MDA-MB-361: Established from a brain metastasis. The cells express ER, PR, EGFR and HER2/neu.

MDA-MB-435: Established from a pleural effusion. The cells are ER-negative, E-cadherin negative, and are highly invasive and metastatic in immunodeficient mice.

MDA-MB-468: Established from a pleural effusion. The cells have amplified EGFR and are ER-negative.

SK-BR-3: Established from a pleural effusion. The cells have amplified HER/2/neu, express EGFR and are ER-negative.

T-47D: established from a pleural effusion. The cells retain expression of E-cadherin, ER and PR.

ZR-75-1: Established from ascites fluid. The cells express ER, E-cadherin, HER2/neu and VEGF.

The PAX2-to-DEFB-1 expression ratio will be determined using the methods described in Example 9.

EXAMPLE 13

Expression of DEFB1 in Breast Cancer Cells

DEFB1 will be expressed in breast cancer cells using methods described in Example 1. The cell viability and caspase activity will be determined as described in Example 1.

EXAMPLE 14

Inhibition of PAX2 Expression in Breast Cancer Cells

PAX2 expression in breast cancer cells will be inhibited using the siRNA described in Example 2. The expression levels of pro-apoptotic genes such as BAX, BID and BAD, the cell viability and caspase activity will be determined as described in Example 2.

EXAMPLE 15

Effect of DEFB1 Expression on Tumor Growth In Vivo

The anti-tumoral ability of DEFB1 will be evaluated by injecting breast cancer cells that overexpress DEFB1 into nude mice. Breast cancer cells will be transfected with an expression vector carrying the DEFB1 gene. Cells expressing the exogenous DEFB1 gene will be selected and cloned. Only single-cell suspensions with a viability of >90% are used. Each animal receives approximately 500,000 cells administered subcutaneously into the right flank of female nude mice. There are two groups, a control group injected with vector only clones and a group injected with the DEFB1 over-expressing clones. 35 mice are in each group as determined by a statistician. Animals are weighed twice weekly, tumor growth monitored by calipers and tumor volumes determined using the following formula: volume=0.5×(width)2×length. All animals are sacrificed by CO2 overdose when tumor size reaches 2 mm3 or 6 months following implantation; tumors are excised, weighed and stored in neutral buffered formalin for pathological examination. Differences in tumor growth between the groups are descriptively characterized through summary statistics and graphical displays. Statistical significance is evaluated with either the t-test or non-parametric equivalent.

EXAMPLE 16

Effect of PAX2 siRNA on Tumor Growth In Vivo

Hairpin PAX2 siRNA template oligonucleotides utilized in the in vitro studies are utilized to examine the effect of the up-regulation of DEFB1 expression in vivo. The sense and antisense strand (see Table 3) are annealed and cloned into pSilencer 2.1 U6 hygro siRNA expression vector (Ambion) under the control of the human U6 RNA pol III promoter. The cloned plasmid is sequenced, verified and transfected into breast cancer cell lines. Scrambled shRNA is cloned and used as a negative control in this study. Hygromycin resistant colonies are selected, cells are introduced into the mice subcutaneously and tumor growth is monitored as described above.

EXAMPLE 17

Effect of Small Molecule Inhibitors of PAX2 Binding on Breast Cancer Cells

The alternative inhibitory oligonucleotides described in Example 6 will be transfected into the breast cancer cells with lipofectamine reagent or Codebreaker transfection reagent (Promega, Inc). In order to confirm DNA-protein interactions, double stranded oligonucleotides will be labeled with [$^{32}$P] dCTP and electrophoretic mobility shift assays are performed DEFB1 expression will be monitored by QRT-PCR and Western analysis following treatment with oligonucleotides. Finally, cell death will be detected by MTT assay and flow cytometry as previously described.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for monitoring breast conditions in a subject, comprising:
   extracting cells obtained from a breast of the subject and preparing one or more cell lysates therefrom;
   performing an assay to determine an expression level of a Paired Box 2 (PAX2) gene relative to an expression level of a control gene in said one or more cell lysates;
   performing an assay to determine an expression level of a beta defensin-1 (DEFB1) gene relative to the expression level of the control gene in said one or more cell lysates; and
   correlating the PAX2-to-DEFB1 expression ratio with a breast condition, wherein a PAX2-to-DEFB1 expression ratio of 100:1 or higher is indicative of the presence of breast cancer in the subject, and a PAX2-to-DEFB1 expression ratio of less than 100:1 is indicative of the presence of non-cancerous or pre-cancerous breast condition in the subject.

2. The method of claim 1, wherein the pre-cancerous breast condition is mammary intraepithelial neoplasia.

3. The method of claim 1, wherein the expression levels of PAX2, DEFB1 and the control genes are determined by quantitative real-time RT-PCR.

4. The method of claim 1, wherein the expression levels of PAX2, DEFB1 and the control genes are determined by expression microarray.

5. The method of claim 1, wherein the control gene is the glyceraldehyde 3-phosphate dehydrogenase (GAPDH) gene.

6. The method of claim 1, further comprising determining an oestrogen receptor/progesterone receptor/human epidermal growth factor receptor 2 (ER/PR/HER2) status in the cells obtained from the breast tissue, wherein an ER+/PR+ or ER+/PR− status is further indicative of the presence of breast cancer in the subject.

7. A method for monitoring breast conditions in a subject, comprising:
   extracting RNA from cells obtained from a breast of a subject to produce one or more extracted RNA samples;
   performing an assay to determine an expression level of a Paired Box 2 (PAX2) gene from an extracted RNA sample relative to an expression level of a control gene from an extracted RNA sample;
   performing an assay to determine an expression level of a beta defensin-1 (DEFB1) gene from an extracted RNA sample relative to the expression level of the control gene from an extracted RNA sample; and
   determining a PAX2-to-DEFB1 expression ratio based on the expression levels of PAX2 and DEFB1 in the extracted RNA sample(s);
   correlating the PAX2-to-DEFB1 expression ratio with a breast condition, wherein a PAX 2-to-DEFB1 expression ratio of 100:1 or higher is indicative of the presence of breast cancer in the subject.

8. The method of claim 7, wherein the pre-cancerous breast condition is mammary intraepithelial neoplasia.

9. The method of claim 7, wherein the expression levels of PAX2, DEFB1 and the control genes are determined by quantitative real-time RT-PCR.

10. The method of claim 7, wherein the expression levels of PAX2, DEFB1 and the control genes are determined by expression microarray.

11. The method of claim 7, wherein the control gene is the glyceraldehyde 3-phosphate dehydrogenase (GAPDH) gene.

12. The method of claim 7, further comprising determining an oestrogen receptor/progesterone receptor/human epidermal growth factor receptor 2 (ER/PR/HER2) status in the cells obtained from the breast of the subject, wherein an ER+/PR+ or ER+/PR− status is further indicative of the presence of breast cancer in the subject.

13. A method for monitoring breast conditions in a subject, comprising:
   extracting proteins from cells obtained from a breast of a subject to produce an extracted protein sample;
   performing an assay to determine an expression level of a Paired Box 2 (PAX2) protein relative to an expression level of a control protein in the extracted protein sample;
   performing an assay to determine an expression level of a beta defensin-1 (DEFB1) protein relative to the expression level of the control protein in the protein sample; and
   determining a PAX2-to-DEFB1 expression ratio based on the expression levels of PAX2 and DEFB1 in the extracted protein sample;
   correlating the PAX2-to-DEFB1 expression ratio with a breast condition, wherein a PAX 2-to-DEFB1 expression ratio of 100:1 or higher is indicative of the presence of breast cancer in the subject.

14. The method of claim 13, wherein the pre-cancerous breast condition is mammary intraepithelial neoplasia.

15. The method of claim 13, wherein the expression levels of the PAX2, DEFB1 and control proteins are determined by immunoassays.

16. The method of claim 13, wherein the expression levels of the PAX2, DEFB1 and control proteins are determined by radioimmune precipitation assay (RIPA).

17. The method of claim 13, wherein the expression levels of the PAX2, DEFB1 and control proteins are determined by one or more immunoassays wherein antibodies specific for PAX2, DEFB1 and the control proteins are bound to a solid support.

18. The method of claim 13, wherein the control protein is the glyceraldehyde 3-phosphate dehydrogenase (GAPDH) protein.

19. The method of claim 13, further comprising determining an oestrogen receptor/progesterone receptor/human epidermal growth factor receptor 2 (ER/PR/HER2) status in the cells obtained from the breast of the subject, wherein an ER+/PR+ or ER+/PR− status is further indicative of the presence of breast cancer in the subject.

* * * * *